(12) United States Patent
Bowers et al.

(10) Patent No.: US 10,430,557 B2
(45) Date of Patent: Oct. 1, 2019

(54) MONITORING TREATMENT COMPLIANCE USING PATIENT ACTIVITY PATTERNS

(71) Applicant: Elwha LLC, Bellevue, WA (US)

(72) Inventors: Jeffrey A. Bowers, Bellevue, WA (US); Paul Duesterhoft, Grapevine, TX (US); Daniel Hawkins, Pleasanton, CA (US); Roderick A. Hyde, Redmond, WA (US); Edward K. Y. Jung, Bellevue, WA (US); Jordin T. Kare, San Jose, CA (US); Eric C. Leuthardt, St. Louis, MO (US); Nathan P. Myhrvold, Medina, WA (US); Michael A. Smith, Phoenix, AZ (US); Elizabeth A. Sweeney, Seattle, WA (US); Clarence T. Tegreene, Mercer Island, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 327 days.

(21) Appl. No.: 15/400,462

(22) Filed: Jan. 6, 2017

(65) Prior Publication Data

US 2017/0169191 A1    Jun. 15, 2017

Related U.S. Application Data

(63) Continuation-in-part of application No. 14/938,940, filed on Nov. 12, 2015, now abandoned, which is a
(Continued)

(51) Int. Cl.
*G10L 15/00* (2013.01)
*G06F 19/00* (2018.01)
(Continued)

(52) U.S. Cl.
CPC .......... *G06F 19/3481* (2013.01); *A61B 3/113* (2013.01); *A61B 5/0022* (2013.01);
(Continued)

(58) Field of Classification Search
USPC .................................. 704/231–257, 270–275
See application file for complete search history.

(56) References Cited

U.S. PATENT DOCUMENTS 4,360,708 A    11/1982 Taguchi et al.
4,455,676 A    6/1984  Kaneda
(Continued)

FOREIGN PATENT DOCUMENTS

WO    WO 2006/109268 A1    10/2006
WO    WO 2008/143908 A2    11/2008

OTHER PUBLICATIONS

U.S. Appl. No. 14/939,143, Bowers et al.
(Continued)

*Primary Examiner* — Jesse S Pullias

(57) ABSTRACT

Methods and systems for monitoring compliance of a patient with a prescribed treatment regimen are described. Patient activity is detected unobtrusively with an activity sensor at the patient location, and activity data is transmitted to a monitoring location. Patient speech detected during use of a communication system such as a mobile telephone by the patient may also be used as an activity signal. Patient activity and/or speech is processed at the patient location or monitoring location to identify activity parameters or patterns that indicate whether the patient has complied with the prescribed treatment regimen. The activity sensor and other components at the patient location may be incorporated into, or associated with, a cell phone, computing system, game system, or vehicle system, for example. The system may provide a report to an interested party, for example a medical
(Continued)

care provider or insurance company, regarding patient compliance with the prescribed treatment regimen.

14 Claims, 52 Drawing Sheets

Related U.S. Application Data continuation-in-part of application No. 14/729,322, filed on Jun. 3, 2015, now abandoned, and a continuation-in-part of application No. 14/729,278, filed on Jun. 3, 2015, now abandoned, application No. 15/400,462, which is a continuation-in-part of application No. 14/543,030, filed on Nov. 17, 2014, now Pat. No. 9,589,107, and a continuation-in-part of application No. 14/543,066, filed on Nov. 17, 2014, now Pat. No. 9,585,616.

(51) Int. Cl.
| | |
|---|---|
| *H04L 29/08* | (2006.01) |
| *G10L 25/66* | (2013.01) |
| *G10L 25/78* | (2013.01) |
| *G16H 10/60* | (2018.01) |
| *A61B 3/113* | (2006.01) |
| *A61B 5/00* | (2006.01) |
| *G06Q 50/24* | (2012.01) |
| *G16H 10/20* | (2018.01) |
| *G16H 15/00* | (2018.01) |
| *A61B 5/024* | (2006.01) |
| *A61B 5/0476* | (2006.01) |
| *A61B 5/117* | (2016.01) |
| *A61B 5/16* | (2006.01) |

(52) U.S. Cl.
CPC .......... *A61B 5/4064* (2013.01); *A61B 5/4803* (2013.01); *A61B 5/4833* (2013.01); *G06F 19/325* (2013.01); *G06Q 50/24* (2013.01); *G10L 25/66* (2013.01); *G10L 25/78* (2013.01); *G16H 10/20* (2018.01); *G16H 10/60* (2018.01); *G16H 15/00* (2018.01); *H04L 67/18* (2013.01); *A61B 5/024* (2013.01); *A61B 5/0476* (2013.01); *A61B 5/117* (2013.01); *A61B 5/16* (2013.01); *A61B 5/4082* (2013.01); *A61B 5/4088* (2013.01)

(56) References Cited

U.S. PATENT DOCUMENTS

| | | | |
|---|---|---|---|
| 4,641,349 | A | 2/1987 | Flom et al. |
| 5,572,596 | A | 11/1996 | Wildes et al. |
| 5,913,310 | A | 6/1999 | Brown |
| 6,006,188 | A | 12/1999 | Bogdashevsky et al. |
| 6,014,626 | A | 1/2000 | Cohen |
| 6,162,186 | A | 12/2000 | Scinto et al. |
| 6,186,145 | B1 | 2/2001 | Brown |
| 6,231,344 | B1 | 5/2001 | Merzenich et al. |
| 6,558,321 | B1 | 5/2003 | Burd et al. |
| 7,315,725 | B2 | 1/2008 | Sachs et al. |
| 7,330,566 | B2 | 2/2008 | Cutler |
| 7,378,954 | B2 | 5/2008 | Wendt |
| 7,451,079 | B2 | 11/2008 | Oudeyer |
| 7,616,779 | B2 | 11/2009 | Liao et al. |
| 7,728,839 | B2 | 6/2010 | Yang et al. |
| 7,794,934 | B2 | 9/2010 | Martucci et al. |
| 7,843,356 | B2 | 11/2010 | Webb |
| 8,032,399 | B2 | 10/2011 | Brown |
| 8,229,178 | B2 | 7/2012 | Zhang et al. |
| 8,396,283 | B2 | 3/2013 | Iihoshi et al. |
| 8,494,857 | B2 | 7/2013 | Pakhomov |
| 8,631,063 | B2 | 1/2014 | Helal et al. |
| 8,667,112 | B2 | 3/2014 | Roth et al. |
| 8,808,195 | B2 | 8/2014 | Tseng et al. |
| 8,996,392 | B2 | 3/2015 | Cashman et al. |
| 9,113,795 | B2 | 8/2015 | Hong et al. |
| 9,135,403 | B1 | 9/2015 | Tolmosoff |
| 9,585,616 | B2 * | 3/2017 | Bowers ................ A61B 5/4833 |
| 9,589,107 | B2 * | 3/2017 | Bowers ................ A61B 5/4803 |
| 2002/0138302 | A1 | 9/2002 | Bodnick |
| 2002/0169635 | A1 | 11/2002 | Shillingburg |
| 2002/0193990 | A1 | 12/2002 | Komatsu |
| 2003/0125610 | A1 | 7/2003 | Sachs et al. |
| 2004/0054266 | A1 | 3/2004 | Covington |
| 2004/0167774 | A1 | 8/2004 | Shrivastav |
| 2004/0197750 | A1 | 10/2004 | Donaher et al. |
| 2005/0084832 | A1 | 4/2005 | Janssen et al. |
| 2005/0273017 | A1 | 12/2005 | Gordon |
| 2006/0028556 | A1 | 2/2006 | Bunn et al. |
| 2006/0190419 | A1 | 8/2006 | Bunn et al. |
| 2007/0017136 | A1 | 1/2007 | Mosher, Jr. et al. |
| 2007/0241261 | A1 | 10/2007 | Wendt |
| 2008/0039698 | A1 | 2/2008 | Burton |
| 2008/0242949 | A1 | 10/2008 | Jung et al. |
| 2008/0287821 | A1 | 11/2008 | Jung et al. |
| 2008/0294019 | A1 | 11/2008 | Tran |
| 2008/0312958 | A1 | 12/2008 | Sachs et al. |
| 2009/0005653 | A1 | 1/2009 | Jung et al. |
| 2009/0099848 | A1 | 4/2009 | Lerner et al. |
| 2009/0149769 | A1 | 6/2009 | Pettigrew |
| 2009/0149898 | A1 | 6/2009 | Hulvershorn et al. |
| 2009/0202966 | A1 | 8/2009 | Teicher et al. |
| 2009/0264789 | A1 | 10/2009 | Molnar et al. |
| 2009/0270786 | A1 | 10/2009 | Hyde et al. |
| 2009/0271008 | A1 | 10/2009 | Hyde et al. |
| 2010/0076249 | A1 | 3/2010 | Leuthardt et al. |
| 2010/0174533 | A1 | 7/2010 | Pakhomov |
| 2010/0211005 | A1 | 8/2010 | Edwards et al. |
| 2010/0217100 | A1 | 8/2010 | LeBoeuf et al. |
| 2010/0274577 | A1 | 10/2010 | Firminger et al. |
| 2010/0312579 | A1 | 12/2010 | Firminger et al. |
| 2011/0224912 | A1 | 9/2011 | Bhavaraju et al. |
| 2012/0116186 | A1 | 5/2012 | Shrivastav et al. |
| 2013/0046477 | A1 | 2/2013 | Hyde et al. |
| 2013/0085758 | A1 | 4/2013 | Csoma et al. |
| 2013/0110511 | A1 | 5/2013 | Spiegel et al. |
| 2013/0179188 | A1 | 7/2013 | Hyde et al. |
| 2013/0253291 | A1 | 9/2013 | Dixon et al. |
| 2013/0254287 | A1 | 9/2013 | Biswas et al. |

OTHER PUBLICATIONS

U.S. Appl. No. 14/939,013, Bowers et al.
U.S. Appl. No. 14/938,973, Bowers et al.
U.S. Appl. No. 14/938,940, Bowers et al.
Aleksic et al.; "Audio-Visual Biometrics"; Proceedings of the IEEE; Nov. 2006; pp. 2025-2044; vol. 94, No. 11; IEEE.
Biospace.com; "Measuring 'Moodtraces': New App Helps Monitor Depression"; Biospace.com; Feb. 27, 2015; pp. 1-2; located at http://www.biospace.com/news_print.aspx?NewsEntityId=366575.
Bleichner et al.; "Exploring miniaturized EEG electrodes for brain-computer interfaces. An EEG you do not see?"; Physiological Reports; 2015; pp. 1-9; vol. 3, Iss. 4, e12362; Wiley Periodicals, Inc.
Chandra et al.; "A review on Speech and Speaker Authentication System using Voice Signal feature selection and extraction"; 2009 IEEE International Advance Computing Conference (IACC 2009); Mar. 6-7, 2009; pp. 1341-1346; IEEE.
U.S. Appl. No. 14/729,322, Bowers et al.
U.S. Appl. No. 14/729,278, Bowers et al.
U.S. Appl. No. 14/543,066, Bowers et al.
U.S. Appl. No. 14/543,030, Bowers et al.
Covington et al.; "Schizophrenia and the structure of language: The linguist's view"; Schizophrenia Research; bearing dates of Dec. 10, 2004 and 2005; pp. 85-98; vol. 77; Elsevier B.V.
Coxworth, Ben; "Bipolar disorder app predicts mood swings by eavesdropping on phone conversations"; Gizmag; May 12, 2014; pp. 1-5; located at http://www.gizmag.com/priori-bipolar-disorder-voice-app/32023/.

(56) References Cited

OTHER PUBLICATIONS

Delorme et al.; "EEGLAB: an open source toolbox for analysis of single-trial EEG dynamics including independent component analysis"; Journal of Neuroscience Methods; 2004; pp. 1-14; vol. 134.
Essig, Todd; "How Is Your Mood Today? Hey, There's an App for That"; Forbes; May 15, 2014; pp. 1-4; located at http://www.forbes.com/sites/toddessig/2014/05/15/how-is-your-mood-today-hey-theres-an-app-for-that/.
"faceLAB 5 Specifications"; Seeing Machines; 2012; pp. 1.
Fotiou et al.; "Pupil reaction to light in Alzheimer's disease: evaluation of pupil size changes and mobility"; Aging Clin Exp Res; Oct. 2007; pp. 364-371; vol. 19, No. 5 (abstract only).
Gaba et al.; "Biometric Identification on the Basis of BPNN Classifier with Other Novel Techniques Used for Gait Analysis"; International Journal of Recent Technology and Engineering (IJRTE); Sep. 2013; pp. 137-142; vol. 2, Issue 4.
Gibin, Thomas; "Analysis of Gait of a Person for Individual Authentication"; European Journal of Academic Essays; 2014; pp. 33-38; vol. 1, No. 3.
Hancock et al.; "Hungry like the wolf: A word-pattern analysis of the language of psychopaths"; Legal and Criminological Psychology; 2011; pp. 1-13; The British Psychological Society.
Hansenne, Michel; "Event-Related Brain Potentials in Psychopathology: Clinical and Cognitive Perspectives"; Psychologica Belgica; 2006; pp. 5-36, vol. 46, Iss. 1-2.
Hollmer, Mark; "Smartphone app shows promise monitoring voice patterns to predict bipolar episodes"; Fierce Diagnostics; May 8, 2014; pp. 1-2; located at http://www.fiercediagnostics.com/node/2206/print.
Karam et al.; "Ecologically Valid Long-Term Mood Monitoring of Individuals With Bipolar Disorder Using Speech"; ICASSP; 2014; pp. 1-5; located at http://web.eecs.umich.edu/~emilykmp/EmilyPapers/Karam2014_ICASSP.pdf.
Kataria et al.; "A Survey of Automated Biometric Authentication Techniques"; 2013 Nirma University International Conference on Engineering (NUiCONE); 2013; pp. 1-6; IEEE.
Kuperberg et al.; "Language Dysfunction in Schizophrenia"; Chapter 19; Schiffer-7243F; Mar. 17, 2003; pp. 444-466; located at http://www.nmr.mgh.harvard.edu/kuperberglab/publications/chapters/Kuperberg&Caplan_Neuropsych_2003.pdf.
Levy et al.; "The Genetic Basis of Thought Disorder and Language and Communication Disturbances in Schizophrenia"; J Neurolinguistics; May 1, 2010; pp. 1-23; vol. 23, No. 3; Elsevier Ltd.
Liao et al.; "Biosensor Technologies for Augmented Brain-Computer Interfaces in the Next Decades"; Proceedings of the IEEE; May 13, 2012; pp. 1553-1566; vol. 100; IEEE.
Lin et al.; "Assessing the feasibility of online SSVEP decoding in human walking using a consumer EEG headset"; Journal of NeuroEngineering and Rehabilitation; 2014; pp. 1-8; vol. 11.
McCowan et al.; "The Delta-Phase Spectrum With Application to Voice Activity Detection and Speaker Recognition"; IEEE Transactions on Audio, Speech, and Language Processing; Sep. 2011; pp. 2026-2038; vol. 19, No. 7; IEEE.
Nicholl et al.; "Neuropsychiatric Sequelae of Traumatic Brain Injury"; Semin Neurol.; 2009; pp. 247-255; vol. 29, No. 3.
Nixon et al.; "On Use of Biometrics in Forensics: Gait and Ear"; 18th European Signal Processing Conference (EUSIPCO-2010); Aug. 23-27, 2010; pp. 1655-1659; EURASIP.
PCT International Search Report; International App. No. PCT/US2015/060803; dated Feb. 24, 2016; pp. 1-3.
Pell et al.; "On the Time Course of Vocal Emotion Recognition"; PLoS ONE; Nov. 2011; pp. 1-16; vol. 6, Issue 11, e27256.
Physorg.com; "Speech monitoring could track Parkinson's"; Phys.org; Nov. 17, 2010; pp. 1-2; located at http://phys.org/news/2010-11-speech-track-parkinson.html.
Singer, Emily; "An App that Looks for Signs of Sickness"; MIT Technology Review; Jun. 21, 2011; pp. 1-2; located at http://www.technologyreview.com/news/424422/an-app-that-looks-for-signs-of-sickness/.
Strickland, Eliza; "Smartphone App Keeps Watch Over Schizophrenic Patients"; Spectrum.IEEE.org North American; Jul. 2014; pp. 1-2.
Sumiyoshi et al.; "Neural basis for the ability of atypical antipsychotic drugs to improve cognition in schizophrenia"; Frontiers in Behavioral Neuroscience; Oct. 2013; pp. 1-8; vol. 7, Article 140.
Tausczik et al.; "The Psychological Meaning of Words: LIWC and Computerized Text Analysis Methods"; Journal of Language and Social Psychology; 2010; pp. 24-54; vol. 29(I); Sage Publications.
Wheeler et al.; "Face Recognition at a Distance System for Surveillance Applications"; 2010 Fourth IEEE International Conference on Biometrics Compendium; Sep. 27-29, 2010; pp. 1-8; IEEE.
Whissell, Cynthia; "A comparison of two lists providing emotional norms for English words (ANEW and the DAL)"; Psychological Reports; 2008; pp. 597-600; vol. 102.
Wise et al.; "Event-related potential and autonomic signs of maladaptive information processing during an auditory oddball task in panic disorder"; International Journal of Psychophysiology; 2009; pp. 34-44; vol. 74; Elsevier B.V.
Woodman, Geoffrey F.; "A Brief Introduction to the Use of Event-Related Potentials (ERPs) in Studies of Perception and Attention"; Nov. 2010; pp. 1-28 plus five pages; located at http://www.ncbi.nlm.nih.gov/pmc/articles/PMC3816929/.
Yap et al.; "A Short Review of Methods for Face Detection and Multifractal Analysis"; 2009 International Conference on CyberWorlds; 2009; pp. 231-236; IEEE.
Zander et al.; "A dry EEG-system for scientific research and brain-computer interfaces"; Frontiers in Neuroscience; May 2011; pp. 1-10; vol. 5, Article 53.
European Patent Office, Extended European Search Report, Pursuant to Rule 62 EPC; App. No. EP 15861246.5; Apr. 18, 2018 (received by our agent on Apr. 26, 2018); pp. 1-11.

\* cited by examiner

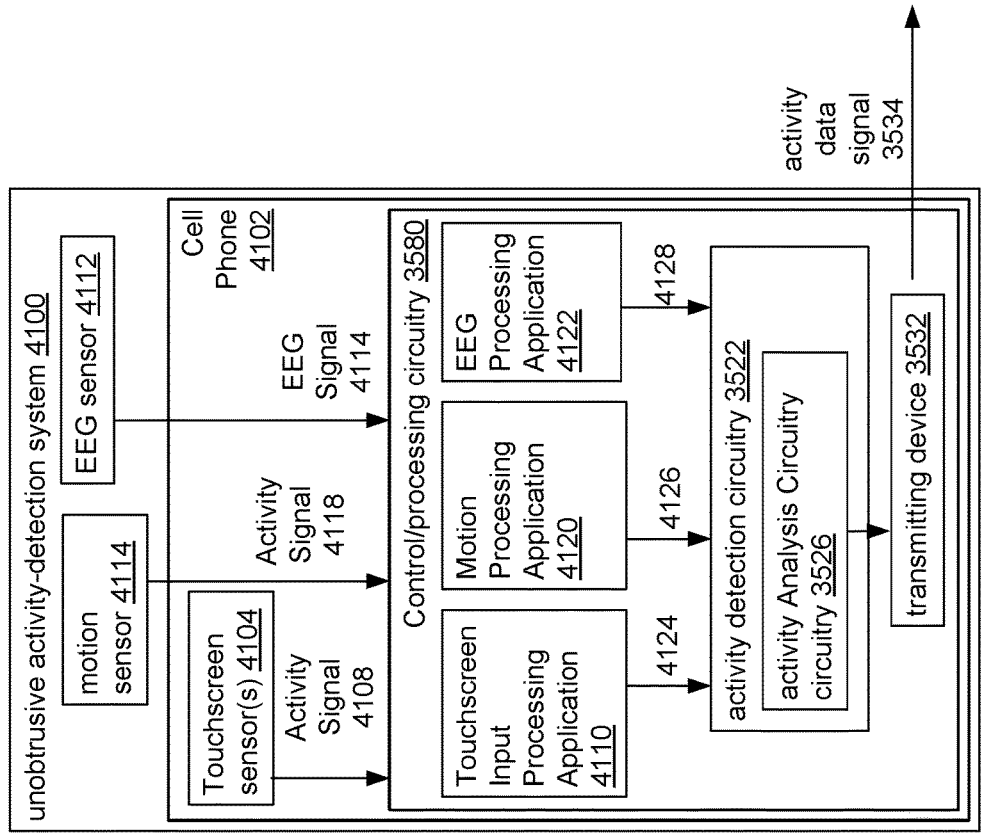
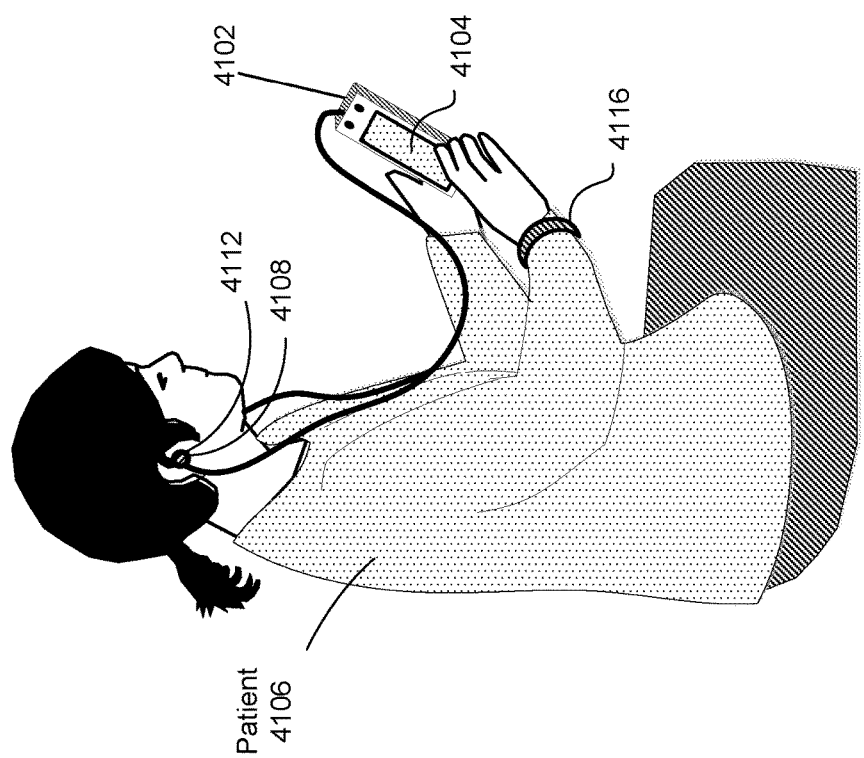
FIG. 41

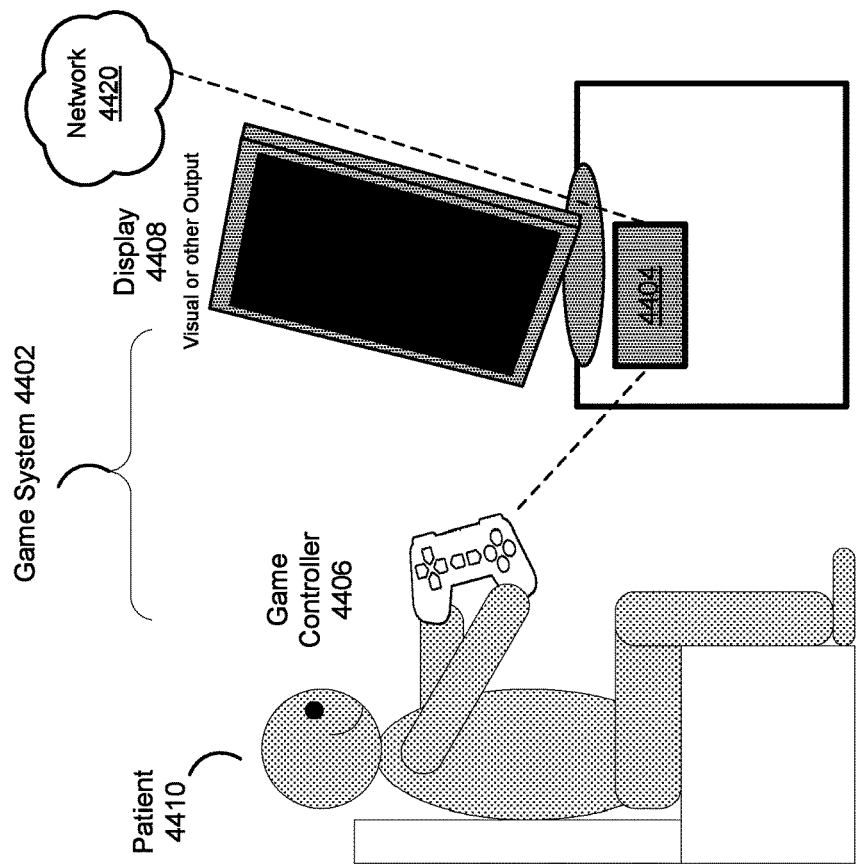
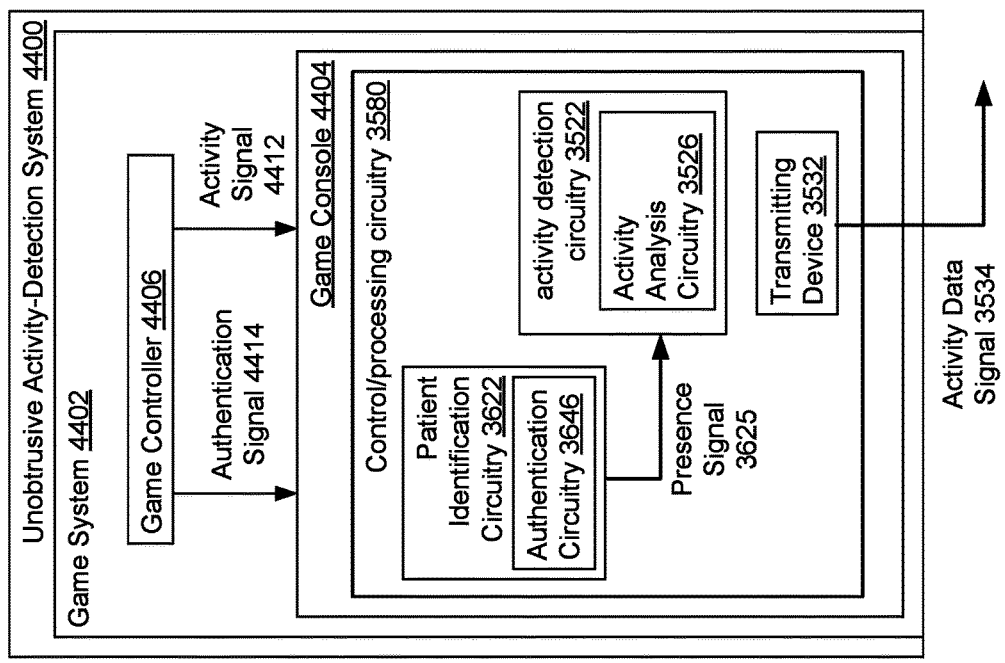
FIG. 44

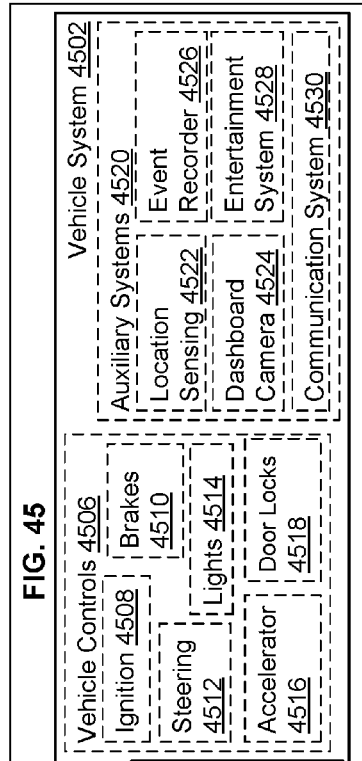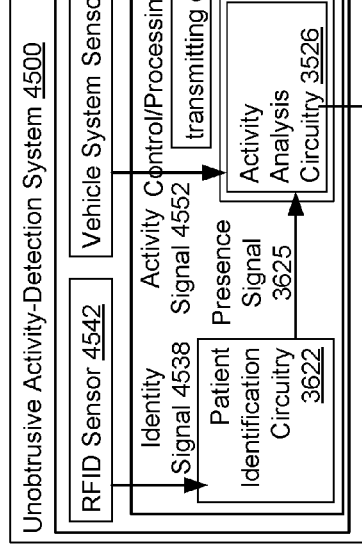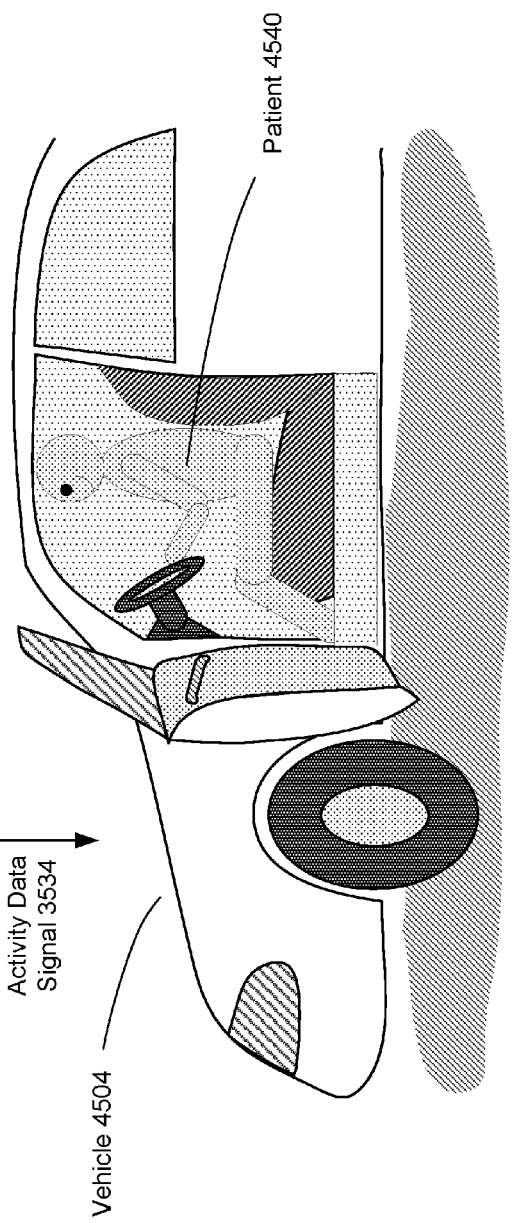
FIG. 45

FIG. 48
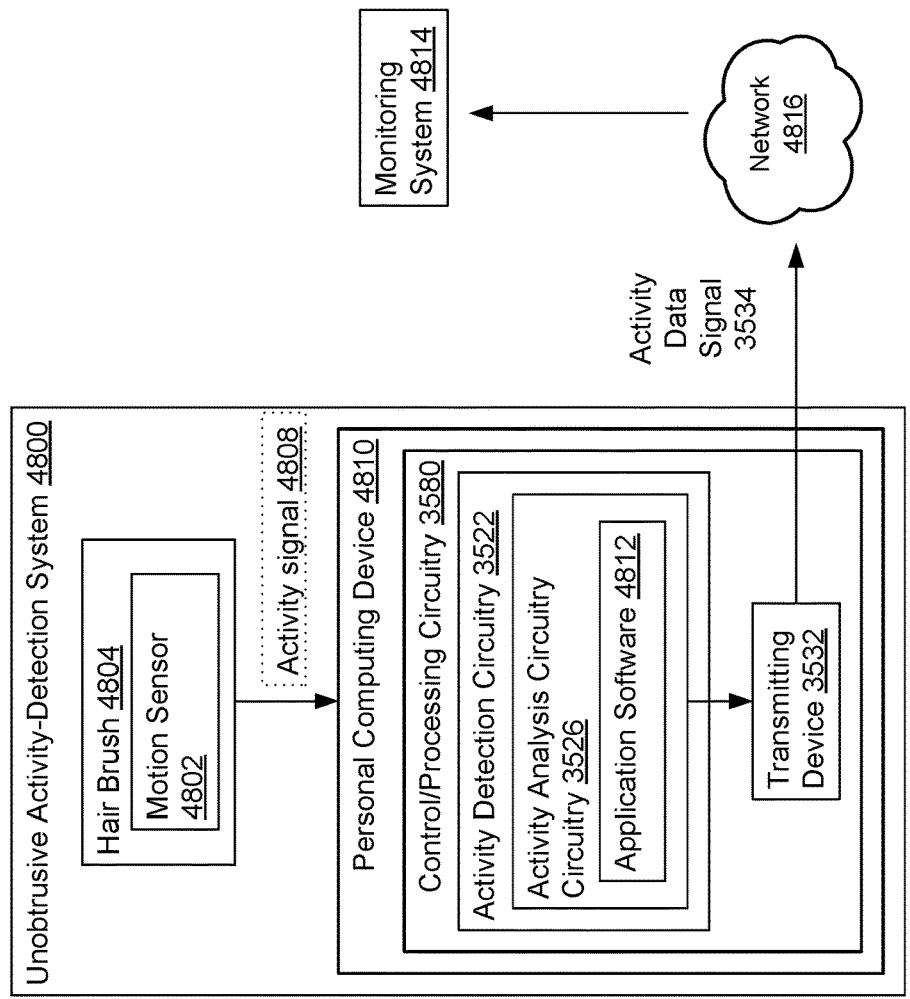
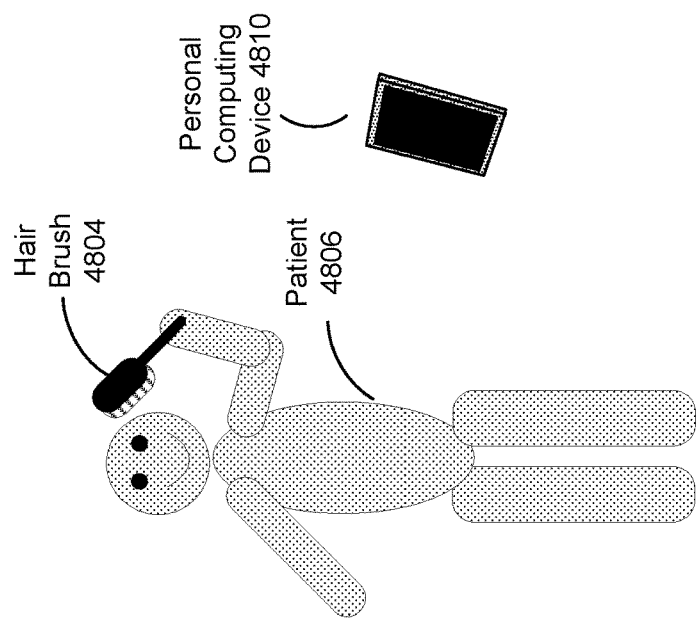

MONITORING TREATMENT COMPLIANCE USING PATIENT ACTIVITY PATTERNS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation-in-part of U.S. patent application Ser. No. 14/543,030, entitled MONITORING TREATMENT COMPLIANCE USING SPEECH PATTERNS PASSIVELY CAPTURED FROM A PATIENT ENVIRONMENT, naming Jeffrey A. Bowers, Paul Duesterhoft, Daniel Hawkins, Roderick A. Hyde, Edward K. Y. Jung, Jordin T. Kare, Eric C. Leuthardt, Nathan P. Myhrvold, Michael A. Smith, Elizabeth A. Sweeney, Clarence T. Tegreene, and Lowell L. Wood, Jr. as inventors, filed 17 Nov. 2014, which is currently co-pending or is an application of which a currently co-pending application is entitled to the benefit of the filing date.

The present application constitutes a continuation-in-part of U.S. patent application Ser. No. 14/543,066, entitled DETERMINING TREATMENT COMPLIANCE USING SPEECH PATTERNS PASSIVELY CAPTURED FROM A PATIENT ENVIRONMENT, naming Jeffrey A. Bowers, Paul Duesterhoft, Daniel Hawkins, Roderick A. Hyde, Edward K. Y. Jung, Jordin T. Kare, Eric C. Leuthardt, Nathan P. Myhrvold, Michael A. Smith, Elizabeth A. Sweeney, Clarence T. Tegreene, and Lowell L. Wood, Jr. as inventors, filed 17 Nov. 2014, which is currently co-pending or is an application of which a currently co-pending application is entitled to the benefit of the filing date.

The present application constitutes a continuation-in-part of U.S. patent application Ser. No. 14/938,940, entitled MONITORING TREATMENT COMPLIANCE USING PASSIVELY CAPTURED TASK PERFORMANCE PATTERNS, naming Jeffrey A. Bowers, Paul Duesterhoft, Daniel Hawkins, Roderick A. Hyde, Edward K. Y. Jung, Jordin T. Kare, Eric C. Leuthardt, Nathan P. Myhrvold, Michael A. Smith, Elizabeth A. Sweeney, Clarence T. Tegreene, and Lowell L. Wood, Jr. as inventors, filed 12 Nov. 2015, which is currently co-pending or is an application of which a currently co-pending application is entitled to the benefit of the filing date, and which is a continuation-in-part of U.S. patent application Ser. No. 14/729,278, entitled MONITORING TREATMENT COMPLIANCE USING SPEECH PATTERNS CAPTURED DURING USE OF A COMMUNICATION SYSTEM, naming Jeffrey A. Bowers, Paul Duesterhoft, Daniel Hawkins, Roderick A. Hyde, Edward K. Y. Jung, Jordin T. Kare, Eric C. Leuthardt, Nathan P. Myhrvold, Michael A. Smith, Elizabeth A. Sweeney, Clarence T. Tegreene, and Lowell L. Wood, Jr. as inventors, filed 3 Jun. 2015; and is also a continuation-in-part of U.S. patent application Ser. No. 14/729,322, entitled DETERMINING TREATMENT COMPLIANCE USING SPEECH PATTERNS CAPTURED DURING USE OF A COMMUNICATION SYSTEM, naming Jeffrey A. Bowers, Paul Duesterhoft, Daniel Hawkins, Roderick A. Hyde, Edward K. Y. Jung, Jordin T. Kare, Eric C. Leuthardt, Nathan P. Myhrvold, Michael A. Smith, Elizabeth A. Sweeney, Clarence T. Tegreene, and Lowell L. Wood, Jr. as inventors, filed 3 Jun. 2015.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a system for monitoring compliance of a patient with a prescribed treatment regimen includes, but is not limited to, at least one receiving device for use at a monitoring location for receiving a speech data signal transmitted to the monitoring location from a patient location, the speech data signal containing speech data, the speech data including patient speech data representing spontaneous speech sensed from a patient with at least one audio sensor at the patient location, and the patient having a brain-related disorder and a prescribed treatment regimen for treating at least one aspect of the brain-related disorder; speech identification circuitry configured to identify the patient speech data corresponding to speech from the patient in the speech data, the patient speech data including data indicative of at least one patient speech pattern; compliance determination circuitry configured to determine compliance of the patient with the prescribed treatment regimen based on whether the patient speech data includes data indicative of the at least one patient speech pattern matching at least one characteristic speech pattern; and reporting circuitry configured to report a conclusion based on the determination of whether the patient has complied with the prescribed treatment regimen. In addition to the foregoing, other system aspects are described in the claims, drawings, and text forming a part of the disclosure set forth herein.

In an aspect, a method of monitoring compliance of a patient with a prescribed treatment regimen includes, but is not limited to, receiving a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at the patient location, and the patient having a brain-related disorder and a prescribed treatment regimen for treating at least one aspect of the brain-related disorder, identifying with speech identification circuitry patient speech data corresponding to speech from the patient in the speech data, the patient speech data including data indicative of at least one patient speech pattern, determining with compliance determination circuitry whether the patient has complied with the prescribed treatment regimen based on whether the patient speech data includes data indicative of the at least one patient speech pattern matching at least one characteristic speech pattern, and reporting with reporting circuitry a conclusion based on the determination of whether the patient has complied with the prescribed treatment regimen. In addition to the foregoing, other method aspects are described in the claims, drawings, and text forming a part of the disclosure set forth herein.

In an aspect, a computer program product includes, but is not limited to, a non-transitory signal-bearing medium bearing one or more instructions for one or more instructions for receiving a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at a patient location, and the patient having a brain-related disorder and a prescribed treatment regimen for treating at least one aspect of the brain-related disorder; one or more instructions for identifying with speech identification circuitry patient speech data corresponding to speech from the patient in the speech data, the patient speech data including data indicative of at least one patient speech pattern; one or more instructions for determining with compliance determination circuitry whether the patient has complied with the prescribed treatment regimen based on whether the patient speech data includes data indicative of the at least one patient speech pattern matching at least one characteristic speech pattern; and one or more instructions for reporting with reporting circuitry a conclusion based on the determination of whether the patient has complied with the prescribed treatment regimen. In addition to the foregoing, other aspects of a computer program product including one or more non-transitory machine-readable data storage media bearing one or more instructions are described in the claims, drawings, and text forming a part of the disclosure set forth herein.

In an aspect, a system includes, but is not limited to, a computing device and instructions that when executed on the computing device cause the computing device to receive a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at a patient location, and the patient having a brain-related disorder and a prescribed treatment regimen for treating at least one aspect of the brain-related disorder; identify with speech identification circuitry patient speech data corresponding to speech from the patient in the speech data, the patient speech data including data indicative of at least one patient speech pattern; determine with compliance determination circuitry whether the patient has complied with the prescribed treatment regimen based on whether the patient speech data includes data indicative of the at least one patient speech pattern matching at least one characteristic speech pattern; and report with reporting circuitry a conclusion based on the determination of whether the patient has complied with the prescribed treatment regimen. In addition to the foregoing, other aspects of a computing device are described in the claims, drawings, and text forming a part of the disclosure set forth herein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 41 is an illustration of an unobtrusive activity detection system implemented in a cell phone.

FIG. 44 is an illustration of an unobtrusive activity detection system implemented in a game system.

FIG. 45 is an illustration of an unobtrusive activity detection system implemented in a vehicle system.

FIG. 48 is an illustration of an unobtrusive activity detection system implemented in connection with a hair brush.

DETAILED DESCRIPTION

Figure 1:
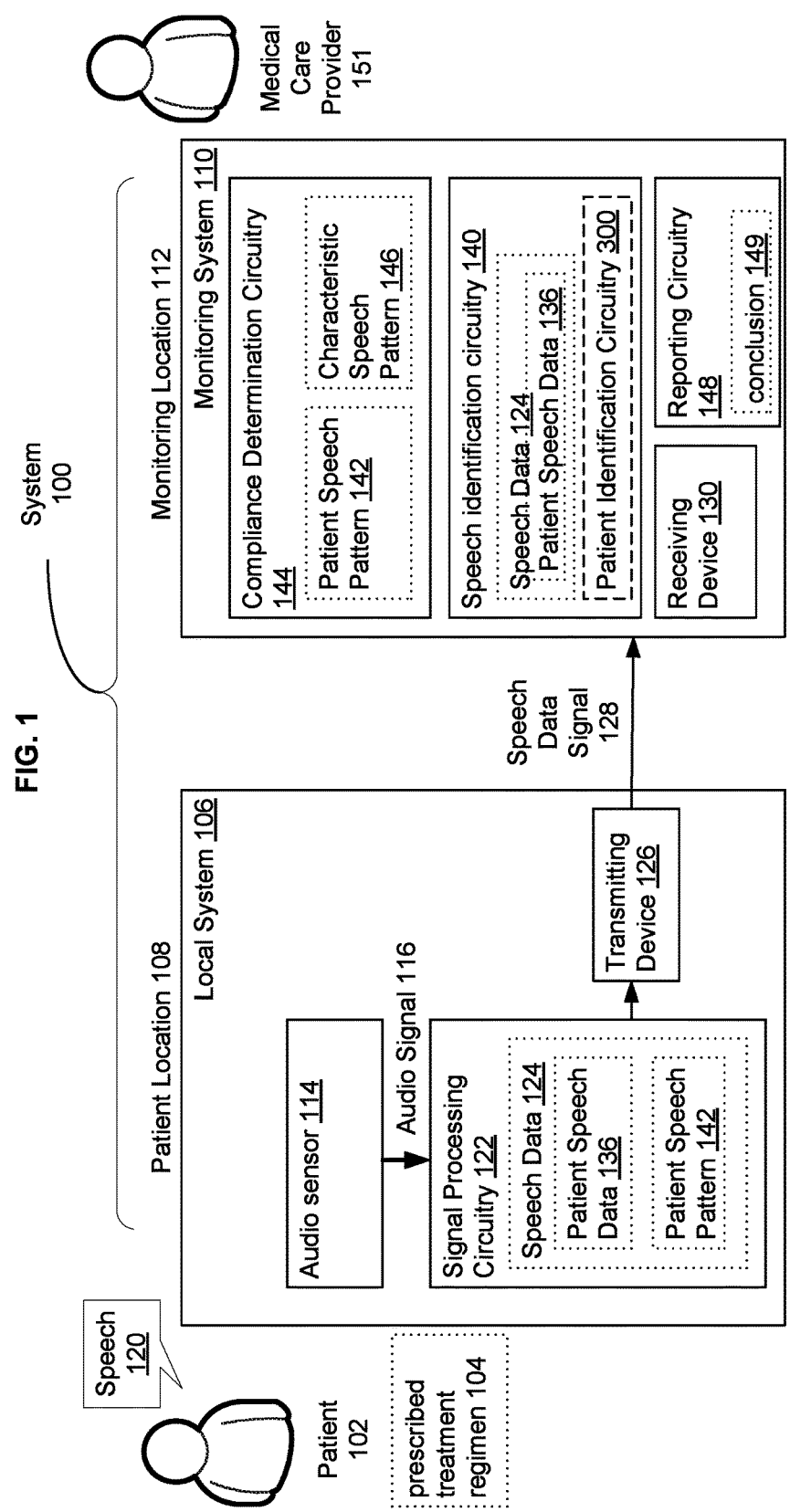
FIG. 1 is a block diagram of a system for monitoring compliance of a patient with a prescribed treatment regimen.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates a system 100 for monitoring compliance of a patient 102 with a prescribed treatment regimen 104. In an aspect, patient 102 has a brain-related disorder, and prescribed treatment regimen 104 is a treatment regimen prescribed to patient 102 for treating at least one aspect of the brain-related disorder. Brain-related disorders include, for example, mental disorders, psychological disorders, psychiatric disorder, traumatic disorders, lesion-related disorders, and/or neurological disorders, as discussed in greater detail herein below. Prescribed treatment regimen 104 may include a prescription for one or more therapeutic treatments, including medications, pharmaceuticals, nutraceuticals, therapeutic activities, diet, sleep, exercise, counseling, etc., to be used individually or in combination. In various aspects, prescribed treatment regimen 104 specifies type, quantity, and time course of any or all such therapeutic treatments. System 100 monitors compliance of patient 102 with a prescribed treatment regimen 104 by detecting and analyzing speech 120 from patient 102. In an aspect, speech 120 is processed by local system 106, and speech data signal 128 is transmitted to monitoring location 112, and a conclusion 149 (e.g., regarding patient's compliance or lack thereof) reported to medical care provider 151. Systems as described herein can be used, for example, to monitor patient compliance with a prescribed treatment regimen at the request of or with the cooperation and/or authorization of the patient, e.g., in the situation that the patient and/or the patient's caregiver wish to track the patient's compliance with the prescribed treatment regimen. In some cases, monitoring of patient compliance with a prescribed treatment regimen can be implemented at the request or requirement of a caregiver, insurance company, or other individual or entity, for example, as a condition of living in a group home, mental health care facility, or other institution. In some cases, monitoring of compliance can be implemented without knowledge and/or authorization of the patient, e.g., in situations in which the patient is not capable of making decisions for his or her self or to fulfill a legal requirement.

System 100 includes local system 106 at patient location 108, and monitoring system 110 at monitoring location 112. In various aspects, patient location 108 includes, but is not limited, to the patient's home, workplace, school, medical care facility, or group home, or the vicinity of a mobile or stationary device used by the patient, e.g., a cell phone or computer.

Local system 106 includes at least one audio sensor 114 for sensing at least one audio signal 116 including spontaneous speech 120 from patient 102 at patient location 108. Local system 106 also includes signal processing circuitry 122 for detecting spontaneous speech 120 in the at least one audio signal 116 and generating speech data 124 indicative of whether the patient has complied with the prescribed treatment regimen based upon the detected spontaneous speech 120. Spontaneous speech refers to speech that is produced independent of any prompt by system 100, and includes, for example, free-flowing or natural speech. Such speech can be considered "passively captured" from the patient environment in that capture of the spontaneous speech is not predicated on the delivery of a prompt to the patient from system 100. It should be noted, however, that, as used herein, spontaneous speech in some cases includes speech produced by the patient in response to prompts or queries by another person, e.g., in the course of interaction with one or more other person. In addition, speech produced by the patient that is not dependent on prior interaction with another person is also considered "spontaneous speech." In various aspects, speech includes coherent speech, incoherent speech, singing, shouting, whispering, crying, chanting, or other verbal or non-verbal vocalizations. Local system 106 also includes at least one transmitting device 126 for transmitting speech data signal 128 containing speech data 124, which includes indicative of whether patient 102 has complied with the prescribed treatment regimen from patient location 108 to receiving device 130 at a monitoring location 112. Local system 106 may include or be implemented on or in connection with a cell phone, personal computer, or stand-alone microprocessor-based device.

System 100 includes monitoring system 110, which is used at monitoring location 112 for monitoring compliance of patient 102 with prescribed treatment regimen 104. Monitoring system 110 allows medical care provider 151 to remotely monitor compliance of patient 102 with prescribed treatment regimen 104. Monitoring location 112 may be, for example, a hospital, clinic, data center, or doctor's office. Monitoring location 112 may be a short distance away from patient location 108 (e.g., in another room of the same building, or even within the same room as patient location 108) or it may be in a separate building, a few miles away, or many miles away. Monitoring system 110 includes at least one receiving device 130 for use at monitoring location 112 for receiving speech data signal 128 transmitted to monitoring location 112 from patient location 108. Speech data signal 128 contains speech data 124, which may include patient speech data 136. For example, patient speech data 136 represents spontaneous speech sensed from patient 102 with at least one audio sensor 114 at patient location 108. Monitoring system 110 includes speech identification circuitry 140 configured to identify patient speech data 136 corresponding to speech from the patient in speech data 124, where patient speech data 136 is indicative of at least one patient speech pattern 142. Monitoring system 110 also includes compliance determination circuitry 144, which is configured to determine compliance of patient 102 with prescribed treatment regimen 104 based on whether patient speech data 124 is indicative of at least one patient speech pattern 142 matching at least one characteristic speech pattern 146. Monitoring system 110 also includes reporting circuitry 148 configured to report a conclusion 149 based on the determination of whether patient 102 has complied with prescribed treatment regimen 104. In an aspect, conclusion 149 is reported to medical care provider 151 or other appropriate party.

Figure 2:
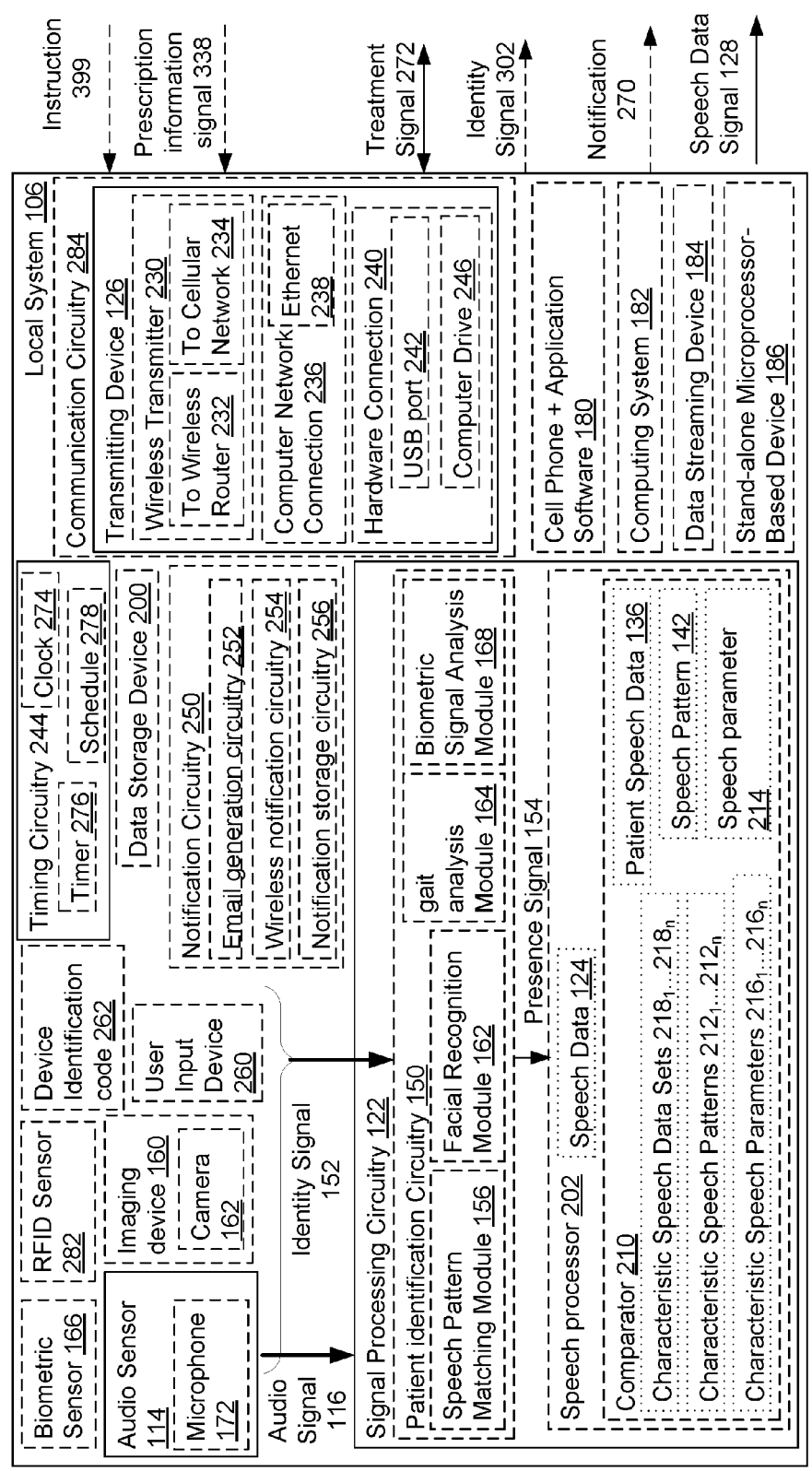
FIG. 2 is a block diagram of components of a system for monitoring compliance of a patient with a prescribed treatment regimen at a patient location.

FIG. 2 provides greater detail regarding local system 106 at patient location 108. Local system 106 can be constructed and implemented in a variety of embodiments in which different devices and/or device components provide the functionality described herein. For example, in various aspects, audio sensor 114, signal processing circuitry 122, and transmitting device 126 may be components of a cell phone configured with application software, as indicated at 180; a computing system or device 182; a data streaming device 184; or a stand-alone microprocessor-based device 186; examples of which are shown in FIGS. 4-7.

In an aspect audio sensor 114 includes microphone 172. Local system 106 may include one or multiple audio sensors 114, which may be of the same or different types, without limitation, and one or more transmitting device 126. Audio sensor 114 may include built-in components (e.g., of cell phone 180, or stand-alone microprocessor-based device 186) or separate components connected to, e.g., a computing system 182 or cell phone 180 via a wired or wireless connection. In an aspect, local system 106 includes one or more data storage device 200, which may be any of various types of data storage and/or memory devices. Local system 106 may include one or more power source (not shown), e.g., a battery, a plug for connecting to an electrical outlet or USB port, or any of various other types of power sources.

Local system 106 includes transmitting device 126, which in various aspects includes a wireless transmitter 230, which may be configured to transmit to a wireless router 232 or cellular network 234, for example. In an aspect, transmitting device 126 includes a computer network connection 236, e.g., an Ethernet connection 238, or a hardware connection 240, for example a USB port 242 or computer drive 246. Transmitting device 126 functions to transmit speech data signal 128, but may also be used to transmit notification 270 generated by notification circuitry 250, identity signal 302, and other data, instructions, or information, for example as discussed elsewhere herein. In some aspects, transmitting device 126 forms a part of communication circuitry 284, which provides for two-way communication between local system 106 and the monitoring system (e.g., monitoring system 110 as shown in FIG. 1), and one-way or two-way communication between local system 106 and other systems or devices located remotely from local system 106.

In an aspect, local system 106 includes notification circuitry 250 for generating a notification. A notification includes any messages or alerts provided to patient 102, medical care provider 151, or other interested parties (e.g., family of patient 102), including but not limited to messages regarding operation of local system 106 or patient compliance, for example. Notifications may take the form of standard messages, a number of which may be stored in data storage device 200. For example, a notification could be a message to patient 102 stating "Reminder: Take your medication" or a message to a medical care provider stating "Alert: Patient xxx speech pattern indicates non-compliance with treatment regimen." Generation of a notification includes retrieval of all or a portion of a message from data storage device 200. In the foregoing example, "xxx" would be replaced by a patient name or identification number, stored separately than the main text of the message and inserted into the message text prior to transmission of the notification to the medical care provider. In various aspects, notification circuitry 250 includes at least one of email generation circuitry 252 for generating an email notification, wireless notification circuitry 254 for generating a notification to be transmitted via a wireless transmitter (e.g., wireless transmitter 230), and notification storage circuitry 256 for storing a notification in a data storage device (e.g., data storage device 200). In some cases, notifications may be stored for later retrieval or transmittal to a monitoring location. Notification 270 generated by notification circuitry 250 can be transmitted by signal processing circuitry 122.

In an aspect, speech data signal 128 transmitted to monitoring system 110 contains processed data. In some cases a determination of whether patient 102 has complied with prescribed treatment regimen 104 is made by local system 106. In some cases speech data signal 128 transmitted to monitoring location 112 includes speech data that has not been subjected to significant processing, and speech processing and detection of patient compliance is performed at monitoring location 112. In an aspect, speech data is stored for later processing, e.g., in data storage device 200 in local system 106, or is subjected to processing but also stored for later transfer to monitoring location 112.

Signal processing circuitry 122 is used for detecting spontaneous speech 120 in the at least one audio signal 116 and generating speech data 124 including data indicative of whether the patient has complied with the prescribed treatment regimen based upon the detected spontaneous speech 120. As used herein, "speech data including data indicative of whether the patient has complied with the prescribed treatment regimen" means speech data that includes informative speech data, i.e., speech data from which it may be determined that the patient complied with the prescribed treatment regimen. "Speech data including data indicative of whether the patient has complied with the prescribed treatment regimen" may, in addition to informative speech data, include non-informative speech data, i.e., speech data that does not provide any information regarding, and from which it cannot be determined, whether the patient complied with the prescribed treatment regimen. As used herein, "speech data" may refer to any or all of a digitized audio signal containing one or more speech-containing portions and one or more non-speech-containing portions, a digitized audio signal from which non-speech-containing portions have been removed to leave one or more speech-containing portions, speech pattern data derived or computed from a digitized audio signal containing speech, or speech parameter data derived or computed from a digitized audio signal containing speech, for example. "Speech data" may include several types of data, e.g., one or more digitized audio signal, one or more speech pattern, and/or one or more speech parameter.

In an aspect, signal processing circuitry 122 includes speech processor 202. In an aspect, speech processor 202 is configured to process the at least one audio signal 116 to identify at least one portion of the at least one audio signal 116 containing spontaneous speech of the patient. In an aspect, speech processor 202 is configured to process at least one audio signal 116 to exclude at least one portion of at least one audio signal 116 that does not contain spontaneous speech of the patient. In an aspect, speech data 124 includes the at least one section of the at least one audio signal 116 containing spontaneous speech of the patient.

In an aspect, speech processor 202 is configured to process at least one audio signal 116 to determine at least one speech pattern 142 of the patient. In an aspect, speech data 124 includes the at least one speech pattern 142 of the patient.

A speech pattern can be defined as a consistent, characteristic form, style, or method of speech comprising a distribution or arrangement of repeated or corresponding parts composed of qualities, acts, or tendencies. In an embodiment a speech pattern can include one or more qualities of diction, elocution, inflection, and/or intonation. In an embodiment a speech pattern can include aspects of language at the lexical level, sentential level, or discourse level. In an embodiment, a speech pattern may conform to the Thought, Language, and Communication Scale and/or Thought and Language Index. Reviews describing speech patterns and linguistic levels and the tools used to study them include Covington M. A., et al. "Schizophrenia and the structure of language: The linguist's view," Schizophrenia Research 77: 85-98, 2005, and Kuperberg and Caplan (2003 Book Chapter: Language Dysfunction in Schizophrenia), which are both incorporated herein by reference.

In an embodiment, a speech pattern includes a linguistic pattern determined at the lexical level. A speech pattern may include a frequency of, for example, pauses, words, or phrases. For example, a speech pattern may include a frequency of pauses. A higher frequency of pauses or reduced verbal fluency can be indicative of alogia associated with a brain disorder, e.g., bipolar disorder, depression, or schizophrenia. For example, a speech pattern may include a frequency of dysfluencies ("uhs" and "ums"). A higher than average frequency of dysfluencies may indicate a slowed speech, the inability to think clearly, or a deliberate attempt to appear unaffected by illness, all of which have been associated with psychological pathologies. For example, a speech pattern may include a distribution of pauses and dysfluencies. A high frequency and particular distribution of pauses and dysfluencies may be indicative of anomia associated with schizophrenia or with an aphasia due to brain injury. For example, a speech pattern may include a frequency of neologisms and/or word approximations, or glossomania. Higher than average frequencies of neologisms and/or word approximations, or glossomania, have been associated with disorders such as schizophrenia, schizoaffective disorder, or mania. For example, a speech pattern may include a frequency of word production. A frequency of word production lower than the norm may be indicative of a brain disorder such as schizophrenia. An excessive speed during speech, as in pressured speech, may be indicative of a brain disorder such as the mania of bipolar disorder, while reduced speed may be indicative of depression or a depressive episode. For example, a pattern may include a type:token ratio (i.e., number of different words (types) in relation to the total number of words spoken (tokens)). A type:token ratio that is generally lower than the norm can be indicative of schizophrenia. For example, a speech pattern may include a frequency of specific words. Quantitative word counts have been used as a tool in the identification and examination of abnormal psychological processes including major depression, paranoia, and somatization disorder. A high frequency of negative emotion words or death-related words may be indicative of depression. Psychologically relevant words can include those listed in one or more dictionaries of the Linguistic Inquiry and Word Count (LIWC) program (see Tausczik and Pennebaker, "The Psychological Meaning of Words: LIWC and Computerized Text Analysis Methods," Journal of Language and Social Psychology 29(1): 24-54, 2010, which is incorporated herein by reference). Words interpreted as carrying normative emotional qualities are found in dictionaries of two programs, *Affective Norms for English Words* (*ANEW*) and *Dictionary of Affect in Language* (*DAL*) (see Whissell C., "A comparison of two lists providing emotional norms for English words (ANEW and the DAL)," Psychol Rep., 102(2):597-600, 2008, which is incorporated herein by reference).

In an embodiment a speech pattern includes a linguistic pattern determined at the lexical level. A speech pattern may include a frequency of, for example, pauses, words, or phrases. For example a speech pattern may include a frequency of pauses. A higher frequency of pauses or reduced verbal fluency can be indicative of alogia associated with a brain disorder, e.g., bipolar disorder, depression, or schizophrenia. For example, a speech pattern may include a frequency of dysfluencies ("uhs" and "ums"). A higher than average frequency of dysfluencies may indicate a slowed speech, the inability to think clearly, or a deliberate attempt to appear unaffected by illness, all of which have been associated with psychological pathologies. For example, a speech pattern may include a distribution of pauses and dysfluencies. A high frequency and particular distribution of pauses and dysfluencies may be indicative of anomia associated with schizophrenia or with an aphasia due to brain injury. For example, a speech pattern may include a frequency of neologisms and/or word approximations, or glossomania. Higher than average frequencies of neologisms and/or word approximations, or glossomania, have been associated with disorders such as schizophrenia, schizoaffective disorder, or mania. For example a speech pattern may include a frequency of word production. A frequency of word production lower than the norm may be indicative of a brain disorder such as schizophrenia. An excessive speed during speech, as in pressured speech, may be indicative of a brain disorder such as the mania of bipolar disorder, while reduced speed may be indicative of depression or a depressive episode. For example, a pattern may include a type:token ratio (i.e., number of different words (types) in relation to the total number of words spoken (tokens)). A type:token ratio that is generally lower than the norm can be indicative of schizophrenia. For example, a speech pattern may include a frequency of specific words. Quantitative word counts have been used as a tool in the identification and examination of abnormal psychological processes including major depression, paranoia, and somatization disorder. A high frequency of negative emotion words or death-related words may be indicative of depression. Psychologically relevant words can include those listed in one or more dictionaries of the Linguistic Inquiry and Word Count (LIWC) program (see Tausczik and Pennebaker, "The Psychological Meaning of Words: LIWC and Computerized Text Analysis Methods," Journal of Language and Social Psychology 29(1): 24-54, 2010, which is incorporated herein by reference). Words interpreted as carrying normative emotional qualities are found in dictionaries of two programs, *Affective Norms for English Words* (*ANEW*) and *Dictionary of Affect in Language* (*DAL*) (see Whissell C., "A comparison of two lists providing emotional norms for English words (ANEW and the DAL)," Psychol Rep., 102(2):597-600, 2008, which is incorporated herein by reference).

In an embodiment a speech pattern includes a linguistic pattern determined at the sentential level or discourse level. For example, a speech pattern can include a consistent grammatical style. A pattern comprising a style that is grammatically deviant from the norm might include the overuse of the past tense, indicating detachment from the subject being discussed. A pattern comprising a style that is grammatically deviant from the norm, e.g., as reflected by a higher percentage of simple sentences and, in compound sentences, fewer dependent clauses may be indicative of schizophrenia. For example, a speech pattern may include a ratio of syntactic complexity (number of clauses and proportion of relative:total clauses). An abnormal ratio may indicate a brain disorder. For example, a speech pattern may include a frequency of subordinate clauses. An increase in subordinate clauses has been observed in the speech of psychopaths (see, e.g., Hancock et al., "Hungry like the wolf: A word-pattern analysis of the language of psychopaths," Legal and Criminological Psychology, 2011; DOI: 10.1111/j.2044-8333.2011.02025.x, which is incorporated herein by reference). For example, a speech pattern may include a relatedness of lexical content such as semantic or sentential priming. A speech pattern of abnormal priming may indicate a brain disorder such as schizophrenia. For example, a speech pattern may include a frequency of one or more use of cohesive ties, e.g., as demonstrated by references, conjunctions, or lexical cohesion. A low frequency of reference ties has been observed in patients suffering from schizophrenia. For example, a speech pattern may include an hierarchical structure within a discourse, e.g., a systematic structure in which propositions branch out from a central proposition. A speech pattern lacking a systematic structure may be indicative of schizophrenia.

For example, a speech pattern including a linguistic pattern determined at the sentential level or discourse level may include a representation of content of thought (what the patient is talking about). For example, a speech pattern may include a representation of form of thought (the way ideas, sentences, and words are put together). A speech pattern containing representations of content or form of thought that differ from those expected (e.g., as determined from population patterns) may indicate a psychological disorder such as schizophrenia. Examples of representations of content or form of thought observed in schizophrenia include derailment, loss of goal, perseveration, and tangentiality. For example, a speech pattern may include aspects of linguistic pragmatics (e.g., cohesion or coherence). Abnormal patterns in pragmatics may be indicative of a brain disorder such as schizophrenia or mania. Examples of speech patterns and content of thought are discussed by Covington, et al., idem, and by Kuperberg and Caplan idem. A program for classifying parts of speech (e.g., noun, verb, adjective, etc.) based on the surrounding context and analysis of semantic content has been developed and is available under the Wmatrix interface (http://ucrel.lancs.ac.uk/wmatrix/) and has been used to analyze the speech of psychopaths (see Hancock, idem).

In an embodiment, a speech pattern includes an acoustic quality. In an embodiment a speech pattern includes volume. For example, excessive or reduced volume may be indicative of a symptom of a brain disorder. In an embodiment a speech pattern includes prosody (the rhythm, stress, and intonation of speech). For example, aprosody or flattened intonation can be indicative of schizophrenia. In an embodiment a speech pattern includes a voice quality of phonation. In an embodiment a speech pattern includes pitch or timbre. For example, abnormalities in pitch have been observed in schizophrenics. For example, a strained quality, choking voice, or creaking voice (laryngealisation) may be indicative of a psychological disorder. Voice qualities and volume in linguistics are discussed by Covington, idem.

For example, the at least one speech pattern 142 may be represented in speech data 124 in numerical or categorical form. For example, a speech pattern represented in numerical form may include one or more numerical values representing one or more speech parameters. Particular speech parameters represented in a speech pattern may be selected for the purpose of evaluating/monitoring particular brain-related disorders. For example, in an aspect a speech pattern for evaluating/monitoring depression includes values representing the following parameters: speech volume, frequency of word production, frequency of pauses, and frequency of negative value words. In another aspect, a speech pattern for evaluating/monitoring schizophrenia includes values representing frequency of word production, frequency of pauses, frequency of disfluencies, type:token ratio, and speech volume. A speech parameter or pattern may be represented in speech data 124 in categorical form; for example, frequency of word production may be categorized as low, medium, or high rather than represented by a specific numerical value.

In an aspect, signal processing circuitry 122 includes comparator 210 for comparing at least one speech pattern 142 of patient 102 with at least one characteristic speech pattern 212 to determine whether the patient has complied with the prescribed treatment regimen. In an aspect, comparator 210 is configured to compare at least one speech pattern 142 of the patient with a plurality of characteristic speech patterns $212_1 \ldots 212_n$ to determine whether the patient has complied with the prescribed treatment regimen. For example, in an aspect, the result of such a comparison is either "patient has complied" or "patient has not complied." In an aspect, signal processing circuitry 122 is configured to determine that patient 102 has failed to comply with the prescribed treatment regimen. In an aspect, signal processing circuitry 122 is configured to determine that patient 102 has complied with prescribed treatment regimen 104. Determination of compliance may be accomplished by a thresholding, windowing, or distance computation of one or multiple parameters relative to characteristic threshold or range values for the parameter. For example, for a given parameter, a patient parameter value higher than a characteristic threshold value may indicate compliance of the patient with the prescribed treatment regimen, while a patient parameter value equal to or lower than the threshold value may indicate non-compliance. As another example, a patient parameter value that lies within a range of characteristic values for the parameter may indicate compliance, while a patient parameter value outside the range of characteristic values indicates non-compliance. Comparator 210 may utilize various types of distance computations to determine whether patient parameter values are within a threshold distance or distance range from characteristic values. Distance computations based on one or more parameters or data values are known (including, but not limited to, least-squares calculations). In an aspect, signal processing circuitry 122 is configured to determine whether the patient has complied with the prescribed treatment regimen based upon a determination of whether the speech corresponds to at least one of a plurality of characteristic speech patterns. For example, the plurality of characteristic speech patterns can include multiple characteristic speech patterns, each corresponding to a patient speech pattern obtained at a different treatment regimen, for example different doses of a drug. By identifying which characteristic speech pattern the patient speech pattern matches or is closest to, the drug dose taken by the patient can be determined. For example, the patient may have taken the drug, but at a lesser dose or less often than was prescribed. Accordingly, the patient's speech pattern matches the characteristic speech pattern associated with the lesser dose of drug, indicating partial, but not full, compliance of the patient with the prescribed treatment regimen.

In an aspect, speech processor 202 is configured to process at least one audio signal 116 to determine at least one speech parameter 214 indicative of whether the patient has complied with the prescribed treatment regimen. Speech parameters include, but are not limited to, measures of prosody, rhythm, stress, intonation, variance, intensity/volume, pitch, length of phonemic syllabic segments, and length of rising segments, for example. In an aspect, speech data 124 includes at least one speech parameter 214, which may include, for example, one or more of prosody, rhythm, stress, intonation, variance, intensity/volume, pitch, length of phonemic syllabic segments, and length of rising segments. In an aspect, signal processing circuitry 122 includes comparator 210 for comparing at least one speech parameter 214 of the patient with at least one characteristic speech parameter 216 to determine whether the patient has complied with the prescribed treatment regimen. In an aspect, comparator 210 is configured to compare at least one speech parameter 214 of the patient with a plurality of characteristic speech parameters $216_1 \ldots 216_n$ to determine whether the patient has complied with the prescribed treatment regimen. For example, in an aspect, the result of such a comparison is either "patient has complied" or "patient has not complied." In an aspect, comparator 210 is configured to compare at least one speech parameter 214 of the patient with a plurality of characteristic speech parameters $216_1 \ldots 216_n$ to determine a level of compliance of the patient with the prescribed treatment regimen. Determination of compliance, non-compliance, or level of compliance may be performed with comparator 210 using thresholding, windowing, or distance measurements, for example, as described herein above. Similarly, determination of compliance or non-compliance of patient 102 with a prescribed treatment regimen maybe be accomplished with the use of comparator 210 for various types of speech data by comparing patient speech data 136 with one or more characteristic speech data set $218_1 \ldots 218_n$, using approaches as described herein above.

In some aspects, signal processing circuitry 122 separates patient speech data 136 originating from patient 102 from speech originating from other individuals and/or from other sounds present in audio signal 116. In an aspect, signal processing circuitry 122 includes patient identification circuitry 150, which is configured to determine the presence of the patient from at least one identity signal 152 sensed at patient location 108. Signal processing circuitry 122 is configured to detect spontaneous speech 120 from patient 102 based at least in part on the determination of the presence of the patient by the patient identification circuitry 150, as indicated by presence signal 154. Identifying speech 120 originating from patient 102 may be of significance, for example, if more than one individual is present, or expected to be present, at patient location 108, such that audio signal 116 may contain speech from individuals other than, or in addition to, patient 102. In various aspects, determining the identity and/or presence of patient 102 may aid in distinguishing speech from patient 102 from speech from other people or non-speech sounds from any other sources, and may assure that conclusions based on analysis patient speech data are reflective of the compliance of patient 102 with the prescribed treatment regimen.

Various types of identity signal 152 can provide information regarding the presence and identity of patient 102. In an aspect, identity signal 152 includes at least a portion of audio signal 116, wherein patient identification circuitry 150 is configured to analyze audio signal 116 to determine the presence of patient 102 by identifying at least a portion of audio signal 116 that resembles known speech of the patient (e.g., with speech pattern matching module 156), and wherein signal processing circuitry 122 is configured to detect spontaneous speech from patient 102 by identifying speech data 124 corresponding to presence of the patient detected from the audio signal, to obtain patient speech data 136. For example, a continuous speech system may be used for identifying the speaker, as described in Chandra, E. and Sunitha, C., "A review on Speech and Speaker Authentication System using Voice Signal feature selection and extraction," IEEE International Advance Computing Conference, 2009. IACC 2009, Page(s): 1341-1346, 2009 (DOI: 10.1109/IADCC.2009.4809211), which is incorporated herein by reference. In an aspect, patient identification circuitry 150 is configured to analyze speech data signal 128 to determine the presence of the patient based on frequency analysis of the speech data signal. Magnitude or phase spectral analysis may be used, as described in McCowan, I.; Dean, D.; McLaren, M.; Vogt, R.; and Sridharan, S.; "The Delta-Phase Spectrum With Application to Voice Activity Detection and Speaker Recognition," IEEE Transactions on Audio, Speech, and Language Processing, 2011, Volume: 19, Issue: 7, Page(s): 2026-2038 (DOI: 10.1109/TASL.2011.2109379), which is incorporated herein by reference.

In another aspect, identity signal 152 includes an image signal received from an imaging device 160 at patient location 108, wherein the patient identification circuitry 150 is configured to analyze the image signal to determine the presence of the patient and to generate presence signal 154, and wherein signal processing circuitry 122 is configured to detect spontaneous speech from the patient by identifying speech data corresponding to presence of the patient detected from the image signal, as indicated by presence signal 154, to obtain patient speech data 136. Imaging device 160 may include a camera 162 or other type of imaging device known to those of skill in the art. In an aspect, the patient identification circuitry 150 is configured to analyze the image signal to determine the presence of the patient through facial recognition, with facial recognition module 162, e.g., using approaches as described in Wheeler, Frederick W.; Weiss, R. L.; and Tu, Peter H., "Face recognition at a distance system for surveillance applications," Fourth IEEE International Conference on Biometrics: Theory Applications and Systems (BTAS), 2010 Page(s): 1-8 (DOI: 10.1109/BTAS.2010.5634523), and Moi Hoon Yap; Ugail, H.; Zwiggelaar, R.; Rajoub, B.; Doherty, V.; Appleyard, S.; and Hurdy, G., "A Short Review of Methods for Face Detection and Multifractal Analysis," International Conference on CyberWorlds, 2009. CW '09, Page(s): 231-236 (DOI: 10.1109/CW.2009.47), both of which are incorporated herein by reference. In an aspect, patient identification circuitry 150 is configured to analyze the image signal to determine the presence of the patient through gait analysis, with gait analysis module 164. Identification of the patient based on gait analysis can be performed for example by methods as described in U.S. Pat. No. 7,330,566, issued Feb. 12, 2008 to Cutler, and Gaba, I. and Kaur P., "Biometric Identification on The Basis of BPNN Classifier with Other Novel Techniques Used For Gait Analysis," Intl. J. of Recent Technology and Engineering (IJRTE) ISSN: 2277-3878, Vol. 2, issue 4, September 2013, pp. 137-142, both of which are incorporated herein by reference.

In an aspect, identity signal 152 includes a biometric signal from at least one biometric sensor 166 at patient location 108, wherein the patient identification circuitry 150 is configured analyze the biometric signal to determine the presence of patient 102, and wherein signal processing circuitry 122 is configured to detect spontaneous speech from the patient by identifying speech data corresponding to presence of the patient as determined from the biometric signal, with biometric signal analysis module 168. Biometric identification can include face and gait recognition, as described elsewhere herein, and recognition based on a variety of other physiological or behavioral characteristics, such as fingerprints, voice, iris, retina, hand geometry, handwriting, keystroke pattern, e.g., as described in Kataria, A. N.; Adhyaru, D. M.; Sharma, A. K.; and Zaveri, T. H., "A survey of automated biometric authentication techniques" Nirma University International Conference on Engineering (NUiCONE), 2013, Page(s): 1-6 (DOI: 10.1109/NUiCONE.2013.6780190), which is incorporated herein by reference. U.S. Pat. No. 8,229,178 issued Jul. 24, 2012 to Zhang et al., which is incorporated herein by reference, describes a method for acquiring a palm vein image with visible and infrared light and extracting features from the image for authentication of individual identity. Biometric identification can be based on imaging of the retina or iris, as described in U.S. Pat. No. 5,572,596 issued to Wildes et al. on Nov. 5, 1996 and U.S. Pat. No. 4,641,349 issued to Flom et al. on Feb. 3, 1987, each of which is incorporated herein by reference. Combinations of several types of identity signals can also be used (e.g., speech and video, as described in Aleksic, P. S. and Katsaggelos, A. K. "Audio-Visual Biometrics," Proceedings of the IEEE Volume: 94, Issue: 11, Page(s): 2025-2044, 2006 (DOI: 10.1109/JPROC.2006.886017), which is incorporated herein by reference).

In an aspect, identity signal 152 includes at least one authentication factor, for example, a security token, a password, a digital signature, or a cryptographic key, entered by patient 102 via user input device 260. User input device 260 can include various types of user input devices or controls as are well known to those of ordinary skill in the art, including but not limited to keyboards, touchpads, touchscreen, mouse, joystick, microphone or other voice input, buttons, or switches. One or more user input device 260 in local system 106 can be used to receive various types of user inputs relating to operation of local system 106, not limited to entry of an authentication factor.

In another aspect, identity signal 152 includes a device identification code 262, which identifies a device or component of local system 106. Device identification code 262 may be, for example, a cell phone identification code, such as an electronic serial number, a mobile identification number, or a system identification code. In various aspects, device identification code 262 identifies a cell phone 180, a computing system 182, or a stand-alone microprocessor-based device 186, or a component thereof. Device identification code 262 can serve to identify patient 102 providing the identified device, for example a personal computer or cell phone, is consistently used only by patient 102.

In an aspect, identity signal 152 includes a radio frequency identification (RFID) signal, e.g., from an RFID device 170, which may be carried, worn by, or otherwise associated with patient 102 and sensed by RFID sensor 282. RFID device 170 can be a passive RFID in a tag or chip associated with the patient, and RFID sensor 282 can be a sensed with an active RFID reader may be used.

In an aspect, presence signal 154 is provided as an input to signal processing circuitry 122. Presence of patient 102 may be indicated by a value of presence signal 154. For example, in some aspects, presence signal 154 is a binary signal; e.g., presence signal 154 has a high value if the patient is present or a low value if the patient is not present (or vice versa). In an aspect, patient speech data 124 is acquired from audio signal 116 only when the value of presence signal 154 indicates that patient 102 is present. Alternatively, in some aspects presence signal 154 is a continuous valued signal that indicates the probability that the patient is present. For example, presence signal 154 has a value of 100 if there is 100 percent probability that the patient is present, a value of zero if there is zero percent probability that the patient is present, or an intermediate value if there is an intermediate probability that the patient is present. It will be appreciated that in some contexts, the determination of whether the patient is present or absent will be relatively straightforward, in which case a binary presence signal may be appropriate, whereas in others (e.g., in cases where the presence of the patient must be distinguished from the presence of other individuals) there is some likelihood of error in identifying the presence of the patient (with the likelihood of error potentially dependent upon the number and identity of the other individuals present), such that an indication of the probability that the patient is present may be more appropriate.

Figure 3:
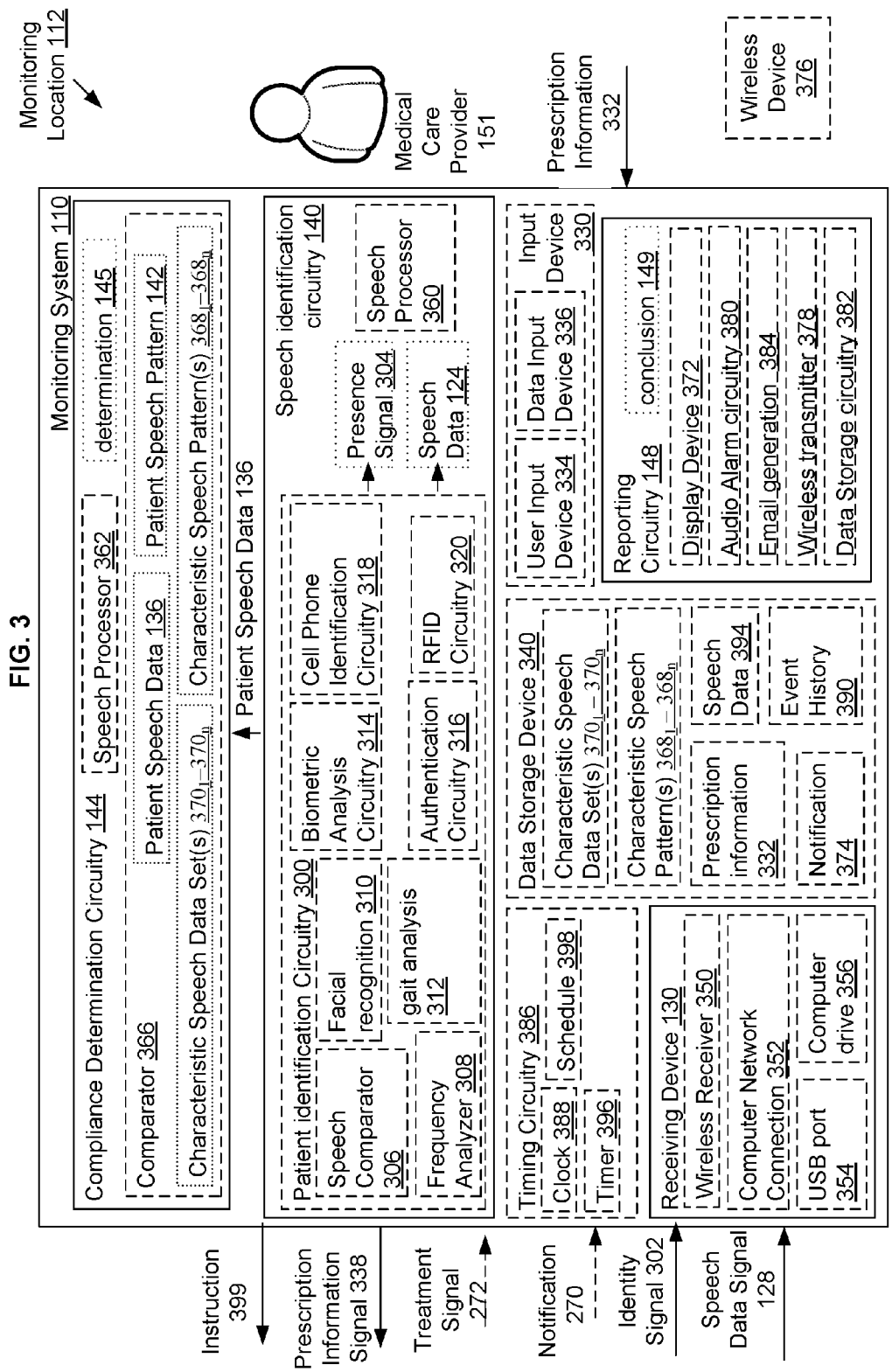
FIG. 3 is a block diagram of components a system for monitoring compliance of a patient with a prescribed treatment regimen at a monitoring location.

FIG. 3 provides greater detail regarding monitoring system 110 at monitoring location 112. In an aspect, speech identification circuitry 140 in monitoring system 110 includes patient identification circuitry 300 configured to determine a presence of the patient from at least one identity signal 302 received at monitoring location 112 from the patient location, wherein speech identification circuitry 140 is configured to identify patient speech data 136 corresponding to speech from the patient in the speech data 124 based at least in part on the determination of the presence of the patient by patient identification circuitry 300.

Presence of the patient is indicated by a value of presence signal 304. In some aspects, presence signal 304 is a binary signal; e.g., presence signal 304 has a high value if the patient is present or a low value if patient is not present (or vice versa). Alternatively, presence signal 304 is a continuous valued signal that indicates the probability that the patient is present. For example, presence signal 304 has a value of 100 if there is 100 percent probability that the patient is present, a value of zero if there is zero percent probability that the patient is present, or an intermediate value if there is an intermediate probability that the patient is present. As discussed herein above, in some contexts, the determination of whether the patient is present or absent will be relatively straightforward, and a binary presence signal may be appropriate, whereas in others (e.g., in cases where the presence of the patient must be distinguished from the presence of other individuals) there is some likelihood of error in identifying the presence of the patient (with the likelihood of error potentially dependent upon the number and identity of the other individuals present), such that an indication of the probability that the patient is present may be more appropriate.

In an aspect, identity signal 302 includes at least a portion of speech data signal 128, and patient identification circuitry 300 is configured to analyze speech data signal 128 to determine the presence of the patient based on speech data signal 128, by identifying at least a portion of speech data signal 128 that resembles a known speech data signal of the patient, with speech comparator 306. Accordingly, speech identification circuitry 140 is configured to identify patient speech data 136 by identifying speech data 124 corresponding to presence of the patient detected from the speech data signal 128. For example, a continuous speech system may be used for identifying the speaker, as described in Chandra, E. and Sunitha, C., "A review on Speech and Speaker Authentication System using Voice Signal feature selection and extraction," IEEE International Advance Computing Conference, 2009. IACC 2009, Page(s): 1341-1346, 2009 (DOI: 10.1109/IADCC.2009.4809211), which is incorporated herein by reference. In an aspect, patient identification circuitry 300 is configured to analyze speech data signal 128 to determine the presence of the patient based on frequency analysis of the speech data signal, with frequency analyzer 308. Magnitude or phase spectral analysis may be used, as described in McCowan, I.; Dean, D.; McLaren, M.; Vogt, R.; and Sridharan, S.; "The Delta-Phase Spectrum With Application to Voice Activity Detection and Speaker Recognition," IEEE Transactions on Audio, Speech, and Language Processing, 2011, Volume: 19, Issue: 7, Page(s): 2026-2038 (DOI: 10.1109/TASL.2011.2109379), which is incorporated herein by reference.

In an aspect, identity signal 302 includes an image signal received from an imaging device at the patient location (e.g., imaging device 160 as shown in FIG. 2), wherein patient identification circuitry 300 is configured to analyze the image signal to determine the presence of the patient, and wherein speech identification circuitry 140 is configured to identify patient speech data 136 by identifying speech data 124 corresponding to presence of the patient detected from the image signal. For example, patient identification circuitry 300 may be configured to analyze the image signal to determine the presence of the patient through facial recognition, with facial recognition circuitry 310, for example using approaches as described in Wheeler, Frederick W.; Weiss, R. L.; and Tu, Peter H., "Face recognition at a distance system for surveillance applications," Fourth IEEE International Conference on Biometrics: Theory Applications and Systems (BTAS), 2010 Page(s): 1-8 (DOI: 10.1109/BTAS.2010.5634523), and Moi Hoon Yap; Ugail, H.; Zwiggelaar, R.; Rajoub, B.; Doherty, V.; Appleyard, S.; and Hurdy, G., "A Short Review of Methods for Face Detection and Multifractal Analysis," International Conference on CyberWorlds, 2009. CW '09, Page(s): 231-236 (DOI: 10.1109/CW.2009.47), both of which are incorporated herein by reference. Alternatively, or in addition, patient identification circuitry 300 may be configured to analyze the image signal to determine the presence of the patient through gait analysis, with gait analysis circuitry 312. Identification of the patient based on gait analysis can be performed, for example by methods as described in U.S. Pat. No. 7,330,566, issued Feb. 12, 2008 to Cutler, and Gaba, I. and Kaur P., "Biometric Identification on The Basis of BPNN Classifier with Other Novel Techniques Used For Gait Analysis," Intl. J. of Recent Technology and Engineering (IJRTE) ISSN: 2277-3878, Vol. 2, issue 4, September 2013, pp. 137-142, both of which are incorporated herein by reference.

In an aspect, the identity signal includes a biometric signal from at least one biometric sensor 166 at the patient location 108 (as shown in FIG. 2), wherein patient identification circuitry 300 in FIG. 3 is configured to analyze the biometric signal to determine the presence of the patient, with the use of biometric analysis circuitry 314, and wherein speech identification circuitry 140 is configured to identify patient speech data 136 by identifying speech data 124 corresponding to presence of the patient detected from the biometric signal. Biometric signal analysis can be performed as described elsewhere herein.

In an aspect, identity signal 302 includes at least one authentication factor, which may be, for example, a security token, a password, a digital signature, or a cryptographic key. In an aspect, an authentication factor is entered by the patient via a user input device, e.g., user input device 260 in FIG. 2. User input device 260 can include various types of user input devices or controls as are well known to those of ordinary skill in the art, including but not limited to a keyboard, touchpad, touchscreen, mouse, joystick, or microphone or other voice input.

In an aspect, patient identification circuitry 300 includes authentication circuitry 316 for determining the identity of the patient based upon the authentication factor. In some aspects, identity signal 302 includes a cell phone identification code, which may be, for example, an electronic serial number, a mobile identification number, or a system identification code, and patient identification circuitry 300 include cell phone identification circuitry 318. Combinations of several types of identity signals can also be used (e.g., speech and video, as described in Aleksic, P. S. and Katsaggelos, A. K. "Audio-Visual Biometrics," Proceedings of the IEEE Volume: 94, Issue: 11, Page(s): 2025-2044, 2006 (DOI: 10.1109/JPROC.2006.886017), which is incorporated herein by reference).

It will be appreciated that identity signal 302 may conveniently be a cell phone identification code when local system 106 is embodied as a cell phone configured with application software, as indicated at 180 in FIG. 2. In connection therewith, patient identification circuitry 300 includes cell phone identification circuitry 318. In another aspect, identity signal 302 includes an RFID signal, e.g., from RFID device 170 associated with patient 102 at patient location 108, as depicted and described in connection with FIG. 2, and patient identification circuitry 300 includes RFID circuitry 320.

In an aspect, monitoring system 110 includes input device 330 for receiving prescription information 332 indicative of the treatment regimen prescribed to the patient. Input device 330 may be a user input device 334 (e.g., a keyboard, touchpad, touchscreen, mouse, joystick, microphone or other voice input, etc.) adapted for receiving prescription information from, e.g., medical care provider 151, or data input device 336 adapted to receive data from another device (e.g., a computer system, a networked system, a cell phone, a barcode reader, a flash drive, a disk drive, etc. via a wired or wireless connection as is well known in the relevant arts).

In an aspect, monitoring system 110 includes at least one data storage device 340 for storing prescription information indicative of the treatment regimen prescribed to the patient. Data stored in data storage device 340 may include, but is not limited to speech data 124, prescription information 332 (including details of the prescribed treatment regimen), stored messages regarding device status, device settings, instructions, or conclusions, for example. Data storage device 340 is a data storage device or system that forms a part of monitoring system 110, or is accessible by monitoring system 110, e.g., on a server and/or cloud-based data storage system. In an aspect, data storage device 340 includes one or more database containing electronic medical records, for example.

In various aspects, the at least one receiving device 130, which receives speech data signal 128 transmitted to monitoring location 112 from patient location 108, includes a wireless receiver 350, a computer network connection 352, a USB port 354, or a computer drive 356. Transmission of data or information to receiving device 130 thus encompasses wireless or wired transmission, and also device-based transmission involving transfer of a data from local system 106 at patient location 108, via a data storage device (e.g., a flash drive or DVD), to a data reading device (USB port 354 or computer drive 356) in monitoring system 110 that reads data from the data storage device. Monitoring system 110 in some aspects includes more than one receiving device, and multiple receiving devices may be of the same or different types. In some aspects, receiving device 130 receives various types of data and/or information from local system 106 at patient location 108, not limited to speech data signal 128. Furthermore, in some aspects receiving device 130 receives data or information from devices and systems other than local system 106. For example, in some aspects, receiving device 130 may also serve as data input device 336.

In an aspect, at least one of speech identification circuitry 140 and compliance determination circuitry 144 includes a speech processor, (see, e.g., speech processor 360 in speech identification circuitry 140 and speech processor 362 in compliance determination circuitry 144.) In an aspect a single speech processor may be shared by speech identification and compliance determination circuitry.

In an aspect, compliance determination circuitry 144 includes speech processor 362 for analyzing the patient speech data 136 to determine the at least one patient speech pattern 142 and a comparator 366 for comparing the at least one patient speech pattern 142 with one or multiple characteristic speech patterns $368_1$-$368_n$. One or more characteristic speech patterns $368_1$-$368_n$ may be stored in data storage device 340. In some aspects, operation of comparator 366 may be substantially similar to that of comparator 210; however, it will be appreciated that the same speech processing functions need not be performed at both patient location 108 and monitoring location 112. Thus, in some aspects system 100 includes either comparator 210 in local system 106 or comparator 366 in monitoring system 110, but not both. In other aspects, system 100 includes some degree of redundancy, such that local system 106 includes comparator 210 and monitoring system 110 includes comparator 366.

Various aspects of system functionality can be distributed between local system 106 and monitoring system 110. With regard to processing of speech signals, if the majority of speech processing takes place in monitoring system 110, speech data transmitted in speech data signal 128 may be minimally processed. On the other hand, if the majority of speech processing is performed in local system 106, speech data signal 128 may contain processed speech data (e.g., speech patterns and/or parameters). However, even if speech processing is performed in local system 106, both processed and unprocessed speech data (e.g., raw speech data as well as speech parameters and or speech patterns) may be included in speech data signal 128.

In some aspects, patient speech data 136 may be compared directly with characteristic speech data sets, rather than being processed first by speech processor 362 to determine patient speech pattern 142, such that the comparison is performed between patient speech pattern 142 and characteristic speech patterns $368_1$-$368_n$, as described above. In an aspect, comparator 366 in compliance determination circuitry 144 compares patient speech data 136 with one or multiple characteristic speech data sets $370_1$-$370_n$ indicative of the characteristic speech pattern, where each said characteristic speech data set is indicative of a characteristic speech pattern.

In the above scenarios, the result of the comparison performed by comparator 366 is a determination that the patient speech data (or patient speech pattern derived therefrom) either does, or does not, match one or more characteristic speech data sets or speech patterns. As discussed above, if there is a match, conclusion 149 is generated regarding whether the patient has complied with the prescribed treatment regimen. In practice, the comparison performed by comparator 366 (which may include thresholding, windowing, distance computation, for example, as discussed herein above) will result in production of a signal by compliance determination circuitry that indicates at least whether the patient has complied with the prescribed treatment regimen, and alternatively, or in addition, a level of compliance with the prescribed treatment regimen.

In an aspect, the compliance determination circuitry 144 is configured to determine that the patient has failed to comply with the prescribed treatment regimen. In some cases, medical care provider 151 (or another party concerned with the patient's health and well-being, such as a parent, family member, caretaker, healthcare provider) is notified only if the patient has failed to comply with the prescribed treatment regimen. Notification can be provided by reporting conclusion 149 with reporting circuitry 148. Alternatively, or in addition, in some aspects, compliance determination circuitry 144 is configured to determine that the patient has complied with the prescribed treatment regimen, e.g. by generating determination 145. In some aspects, monitoring system 110 reports conclusion 149 with reporting circuitry 148 when the patient is in compliance with the prescribed treatment regimen, as indicated by determination 145. It will be appreciated that in various aspects, compliance determination circuitry can be configured to determine both compliance and non-compliance, and additionally, or alternatively, level of compliance (either at specific levels or simply partial compliance), as indicated by a value of determination 145. Compliance or lack thereof can be represented by appropriate text or numerical value in a displayed report or email e.g., reported by reporting circuitry 148, or represented by a binary value in data stored by data storage circuitry 382. Alternatively, or in addition, level of compliance can be represented by a continuous value (e.g., percent compliance) or a text descriptor selected from a number of text descriptors corresponding to different levels of compliance (e.g., non-compliance, low compliance, intermediate compliance, near-full compliance, full compliance). Reporting circuitry 148 provides for formatting determination 145 appropriately (e.g., by including appropriate messages to accompany the value of the determination) and for deciding whether and how to report the conclusion, based upon user preferences. For example, who is notified (medical care provider versus family member) or how notification is provided (stored in an event record, via email, or via a text message to a cell phone) may depend on the patient's level of compliance and the specifics of the patient. That is reporting circuitry 148 can generate different levels of notifications depending on how serious a problem non-compliance is likely to be for the patient.

In various aspects, reporting circuitry 148 is used to report a conclusion 149 to medical care provider 151 or another party. In an aspect, reporting circuitry 148 includes display device 372. Reporting circuitry 148 may include circuitry for generating a notification. For example, a notification may be displayed on display device 372. Generating a notification may include retrieving a stored notification 374 from data storage device 340, e.g., selected from among one or more notifications stored in data storage device 340, as discussed above in connection with notification circuitry 250 in local system 106. Notifications may take the form of text or numerical codes, for example.

In another aspect, reporting circuitry 148 includes circuitry (e.g., wireless transmitter 378) for transmitting a notification to a wireless device 376. Wireless device 376 may be, for example, a pager, cell phone, or other wireless device used by a medical care provider or family member interested in tracking the status of the patient.

In another aspect, reporting circuitry 148 includes audio alarm circuitry 380 for generating an audio alarm, e.g., a tone or voice alert be delivered via a speaker, or activating a bell, buzzer, beeper, or the like to inform medical care provider 151 of the status of the patient.

In another aspect, reporting circuitry 148 includes data storage circuitry 382 for storing a notification in a data storage device, e.g., in event history 390. For example, data storage circuitry 382 may provide for storage of a notification in event history 390 in conjunction with information regarding the time at which the notification was generated, obtained, for example from timing circuitry 386. In an aspect, timing circuitry 386 includes a clock 388 and/or timer 396. Event history 390 may be a part of the subject's electronic medical records, and may be stored locally in monitoring system 110, or elsewhere.

Systems and system components as illustrated generally in FIGS. 1-3 may be better understood by reference to the examples shown in FIG. 4-7.

Figure 4:
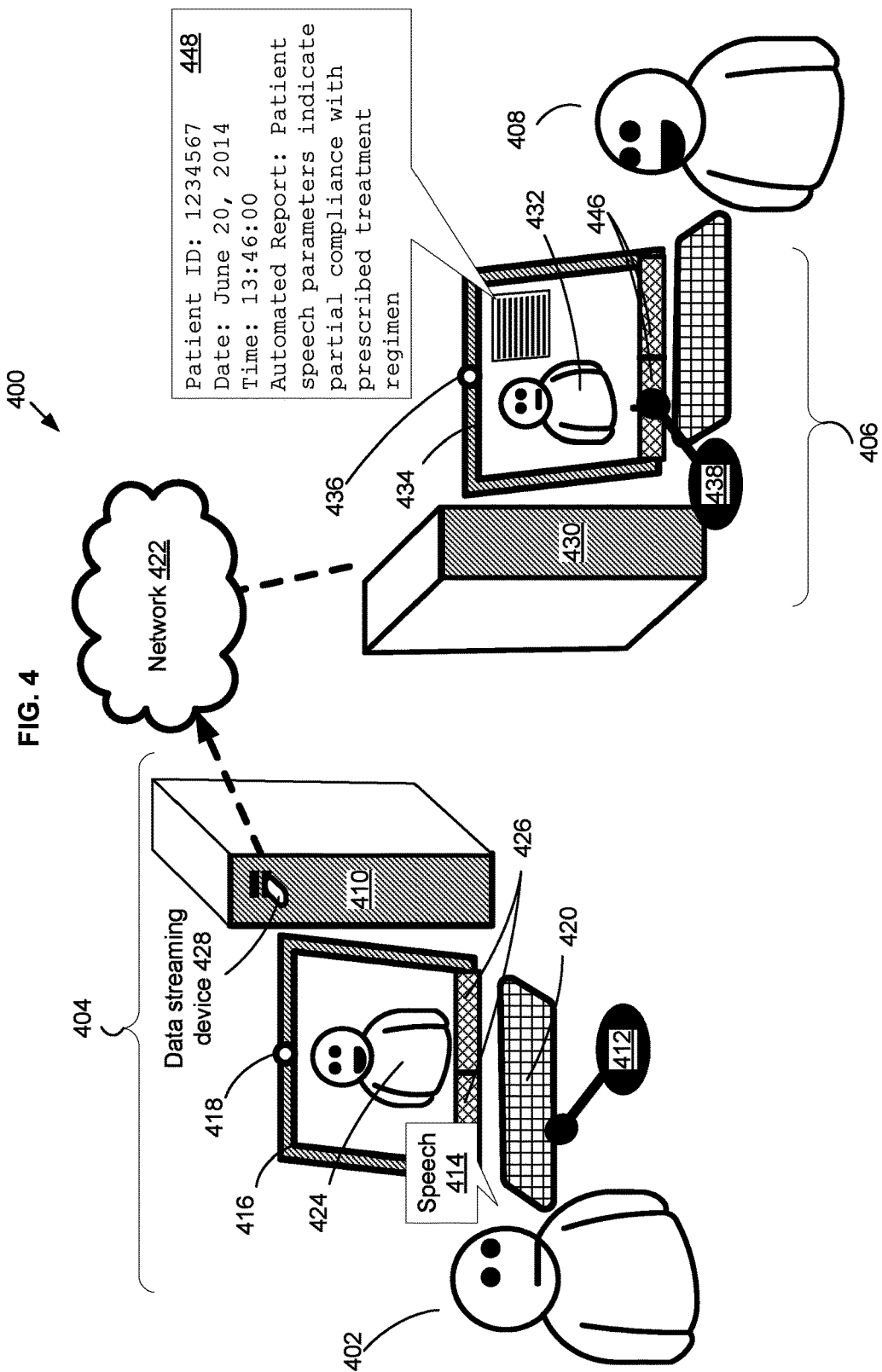
FIG. 4 illustrates an embodiment of a system for monitoring compliance of a patient with a prescribed treatment regimen.

FIG. 4 depicts an embodiment of a system 400 for monitoring compliance of a patient 402 with a prescribed treatment regimen, implemented in connection with the patient's personal computer 410. In an aspect, system 400 is used for monitoring compliance of patient 402 while patient 402 participates in a video consultation with medical care provider 408. In another aspect, system 400 can in addition (or alternatively) be used to monitor compliance of patient 402 during routing activities with data streaming device 428, which is powered by a USB port of computer 410.

System 400 includes system 404 at a patient location and monitoring system 406 used at a monitoring location by a medical care provider 408. System 404 includes a personal computer system including computer 410, microphone 412 for detecting patient speech 414, display 416, camera 418 (which is shown here as being built into display 416, but could also be packaged separately), and keyboard 420.

In the example of FIG. 4, in a first monitoring mode, patient 402 participates in a video consultation with medical care provider 408, with patient voice data being captured by microphone 412, patient image data being captured by camera 418, and both voice and image data being transmitted to computer 430 of monitoring system 406 via network 422. An image 432 of patient 402 is displayed on display 434 for viewing by medical care provider 408. Camera 436 captures an image 424 of medical care provider 408, which is transmitted to system 404 via network 422, where it is displayed on display 416. Microphone 438 captures voice data from medical care provider 408, which is also sent to system 404 and may be delivered to patient 402 via speakers 426. Similar, patient voice data can be presented to medical care provider 408 via speakers 446. In addition to patient image 432, a report 448 containing a conclusion regarding compliance of patient 402 with a prescribed treatment regimen is displayed on display 434. In the example of FIG. 4, report 448 includes a listing of a patient ID number, a date, a time, and a statement regarding patient compliance, e.g., "Patient speech parameters indicate partial compliance with prescribed treatment regimen." Patient identity is determined by entry of an authentication factor (e.g., login and password) by patient 402 when logging in for video conference.

In a second monitoring mode, which is used as the patient is working on computer 410 or in the vicinity, but is not necessarily engaged in a video conference with medical care provider 408, data streaming device 428 captures speech from patient 402 with a built-in microphone and provides for transmission of speech data to network 422. Patient identity is determined by voice recognition. Patient speech data is transmitted from data streaming device 428 to monitoring system 406 via network 422, for processing and reporting to medical care provider 408.

Figure 5:
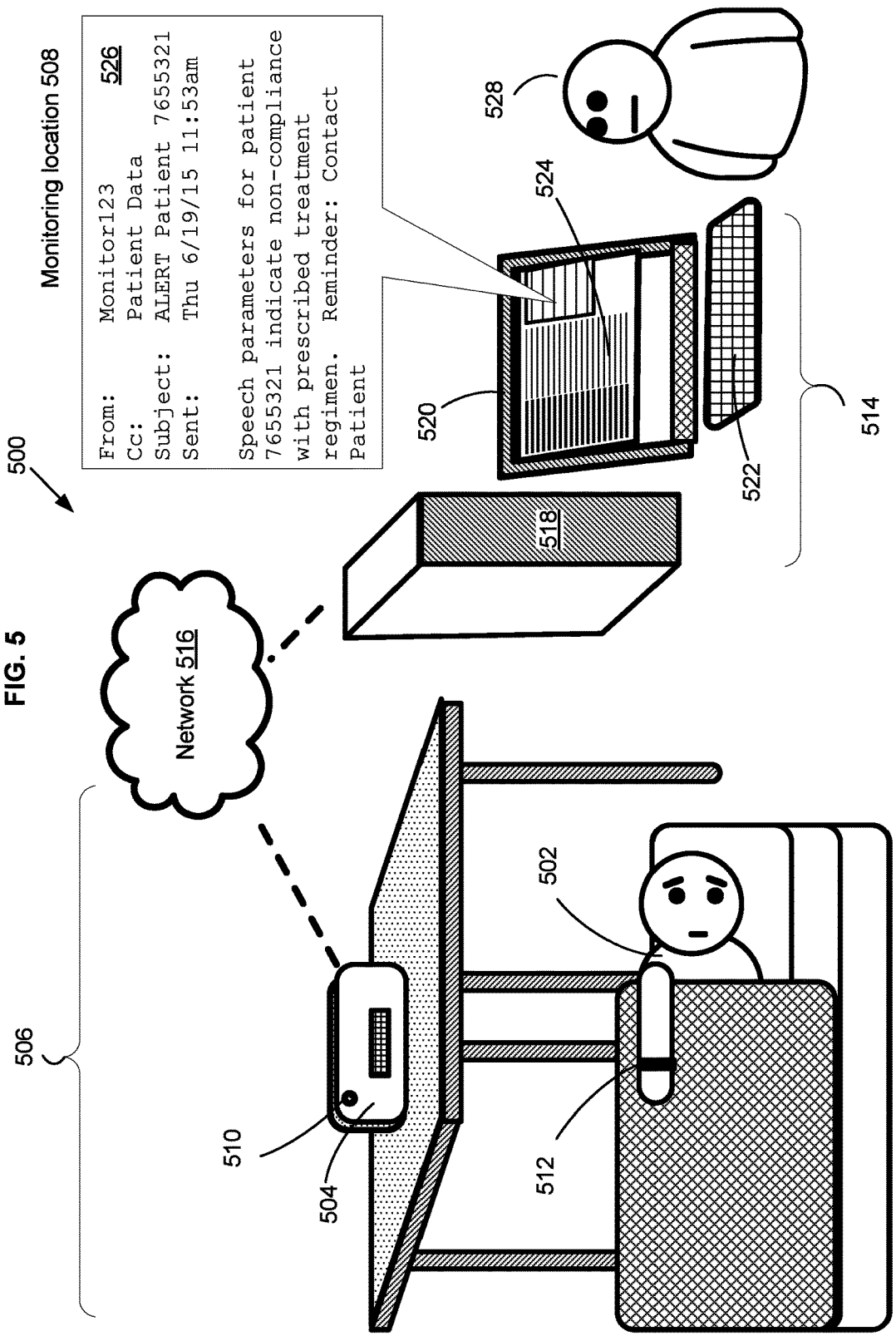
FIG. 5 illustrates another embodiment of a system for monitoring compliance of a patient with a prescribed treatment regimen.

In another example, FIG. 5 depicts a system 500 for monitoring compliance of a patient 502 with a prescribed treatment regimen that includes a stand-alone microprocessor-based device 504 at patient location 506. In an aspect, stand-alone device 504 is configured for easy operation, with minimal user controls. Stand-alone device 504 includes dedicated hardware, firmware and/or software designed to perform the functions described herein. Device 504 is a stand-alone microprocessor-based device in that computing capability at patient location 506 is provided by a dedicated special purpose device and the system does not utilize the computing capability of, e.g., a personal computer or cell phone at the patient location; however, stand-alone device 504 may operate in combination with other system components at the patient location as well as at monitoring location 508. Stand-alone device 504 includes a microphone 510 for sensing patient speech, as well as background sounds. In the example of FIG. 5, patient 502 suffers from depression in which the patient is less active and/or talkative than usual during an episode of the disorder. The content of the patient's speech may also change before or during an episode. Both quantity and content of patient speech may be indicative of the patient's mental state, and hence of the patient's compliance with a prescribed treatment regimen. If patient 502 is present, and microphone 510 detects an audio signal that contains little or no speech or sounds of physical activity of the patient at a time of day when speech or activity would be expected, device 504 generates a report indicating non-compliance of patient 502 with the prescribed treatment regimen. Presence of the patient in the vicinity of device 504, as well as the identity of the patient, can be detected by sensing the presence of an RFID armband 512 worn by patient 502 with an RFID sensor in device 504. Device 504 includes a clock/timing device for tracking the time of day. If non-compliance of the patient with the prescribed treatment regimen is detected, device 504 sends information to computing system 514 at monitoring location 508, via network 516. Computing system 514 includes computer 518, display 520, and keyboard 522. Computer 518 presents information 524, including report 526 concerning patient 502 on display 520, for viewing by medical care provider 528.

Figure 6:
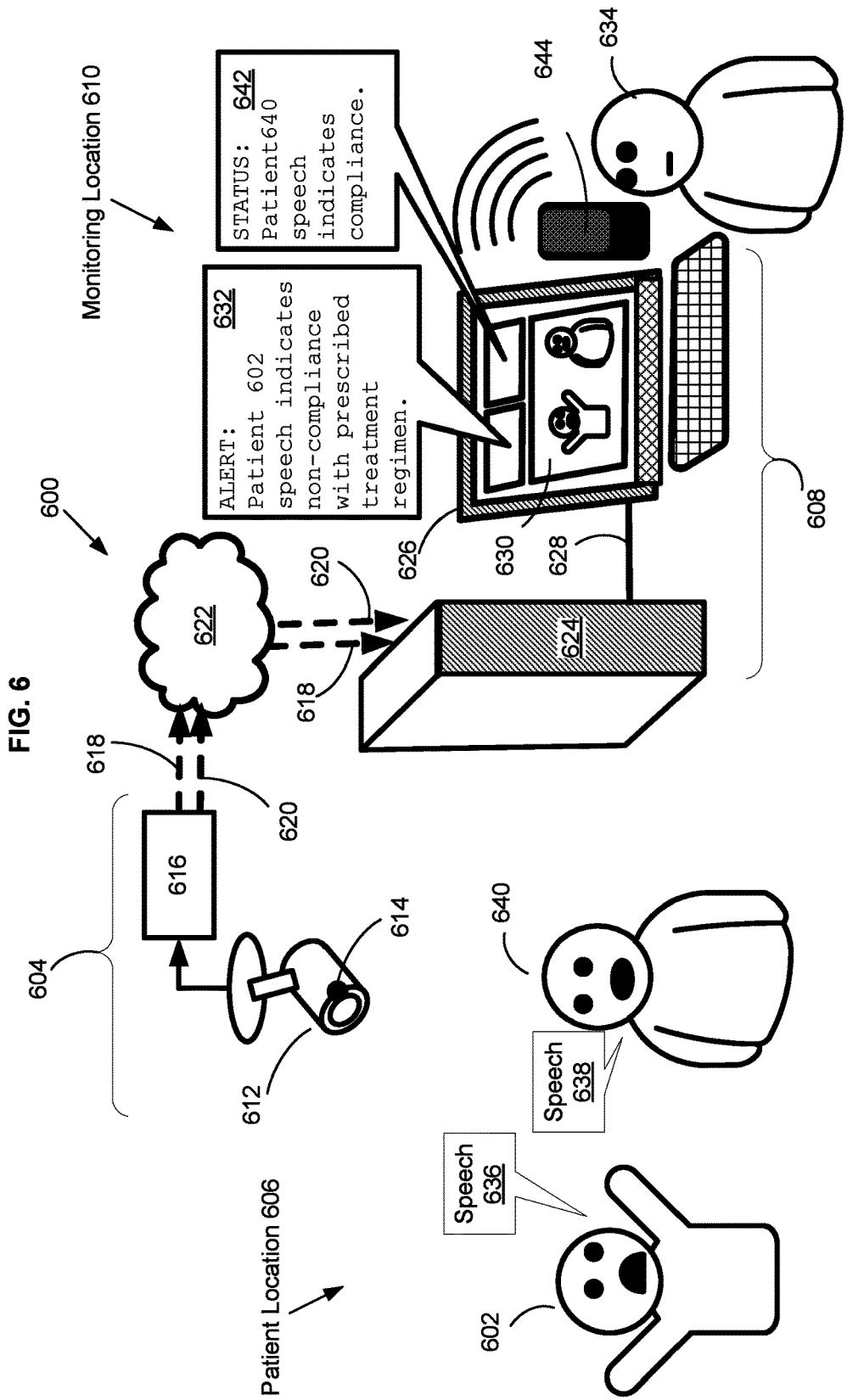
FIG. 6 illustrates another embodiment of a system for monitoring compliance of a patient with a prescribed treatment regimen.

FIG. 6 depicts an example of a system 600 for monitoring patient compliance that is suitable for monitoring a patient 602 in a group setting, for example a group home. System 600 includes a local system 604 in patient location 606, and monitoring system 608 in monitoring location 610. Local system 604 includes imaging device 612, which in this example is a video camera, and microphone 614 connected to circuitry 616. Circuitry 616 transmits a speech data signal 618 containing a speech signal from microphone 614 and identity signal 620 containing a video signal from imaging device 612 to network 622 and from there to monitoring system 608. Circuitry 616 includes conventional closed-circuit TV circuitry that processes speech 636 (e.g., by amplification and filtering) before transmitting it to monitoring system 608. Monitoring system 608 includes computer 624 connected to display 626 by data link 628. Monitoring system 608 can be located in a separate room of a group home from local system 604, connected to local system 604 by a LAN or WAN, for example. Video data contained in identity signal 620 is used to generate image 630, which is displayed on display 626, along with report 632, for viewing by medical care provider 634 (or alternatively, a counselor, or group home staff member, for example). Report 632 is generated by software running on computer 624 based on analysis of speech data signal 618. Speech 636 from patient 602 is separated from speech 638 from second patient 640 based on analysis of identity signal 618. In the present example, analysis of identity signal 618 includes one or both of facial recognition or gait analysis, using methods as discussed herein above. Speech 636 from patient 602 is analyzed to determine whether patient 602 has complied with the prescribed treatment regimen. In the example of FIG. 6, patient 602 exhibits an agitated physical activity pattern (detectable in image 630) and agitated speech pattern (detectable in speech 636), indicating that patient 602 has failed to comply with a prescribed treatment regimen. Accordingly, report 632 states "ALERT: Patient 602 speech indicates non-compliance with prescribed treatment regimen." In addition, an audio alarm (a beep or buzzing sound) is generated on speaker 644 to attract the attention of medical care provider 634. Medical care provider 634 observes the behavior of patient 602 on display 626 in addition to listening to the accompanying audio signal presented on speaker 644. In addition, compliance of patient 640 with a prescribed treatment regimen is also monitored: speech of patient 640 can be detected, separated from the speech of patient 602, analyzed, and compliance reported in the same manner. For example, in FIG. 6, report 642 indicates the status of patient 640: "STATUS: Patient 640 speech indicates compliance."

Figure 7:
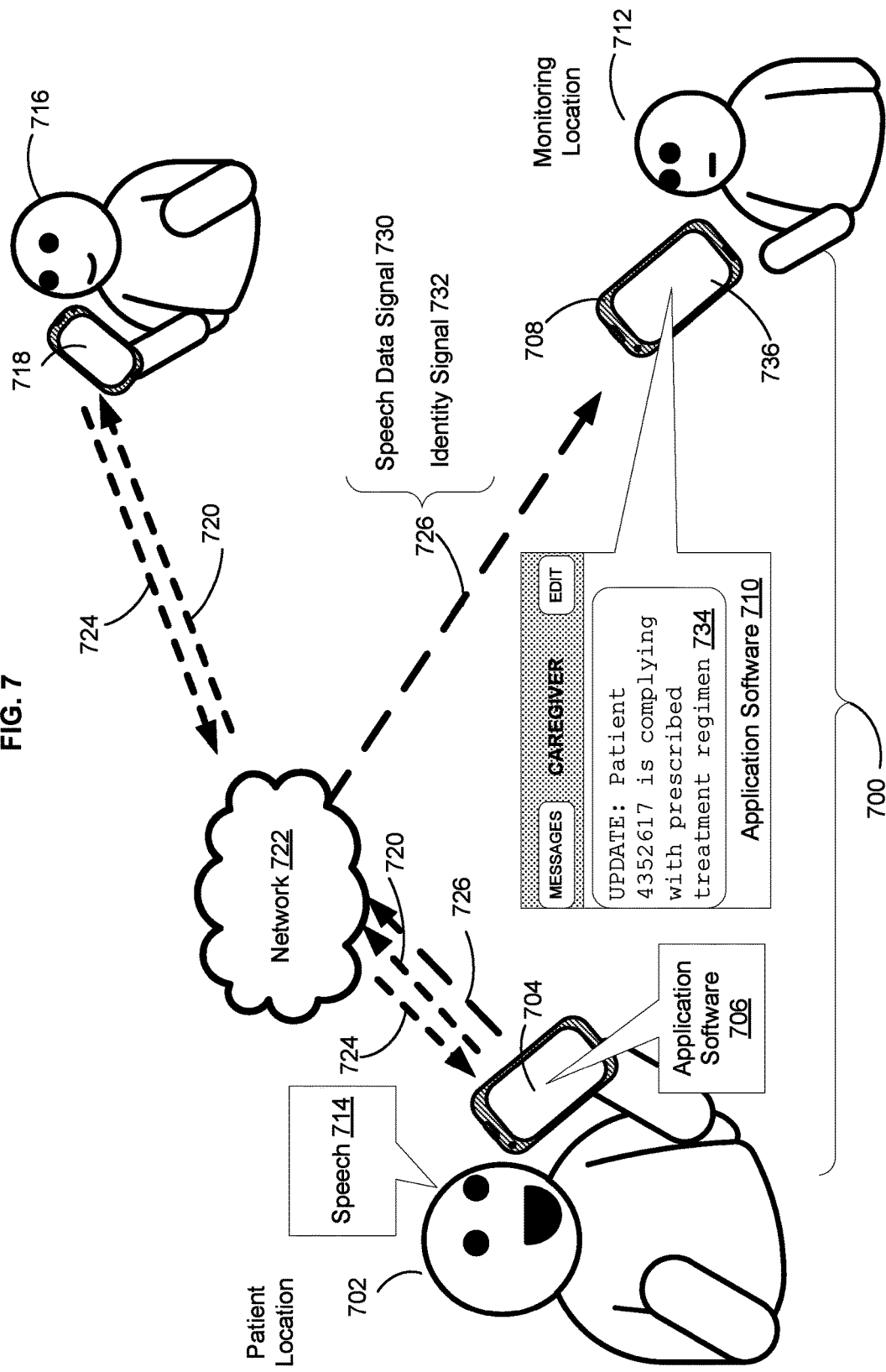
FIG. 7 illustrates another embodiment of a system for monitoring compliance of a patient with a prescribed treatment regimen.

FIG. 7 depicts an example of a system 700 for monitoring compliance of a patient 702 with a treatment regimen. System 700 includes cell phone 704, which is a cell phone used by patient 702, configured with application software 706, and cell phone 708, configured with application software 710, and used by medical care provider 712. System 700 is used to monitor compliance of patient 702 with a prescribed treatment regimen by analyzing speech 714 of patient 702 during the course of routine use of cell phone 704 by patient 702, for example to communicate with person 716 (e.g., a friend) using a cell phone 718. During communication with person 716, a conventional cellular communication signal 720 containing voice data from patient 702 is transmitted to cellular network 722 and from there to cell phone 718. Similarly, cellular communication signal 724 containing voice data from person 716 is transmitted from cell phone 718 to cell phone 704 via cellular network 722. A second cellular signal 726 is transmitted via cellular network 722 to cell phone 708. Second cellular signal 726 contains speech data signal 730 and identity signal 732, which are processed by application software 710 on cell phone 708 to generate report 734. In an aspect, speech data signal 730 contains speech parameters that characterize the speech of patient 702, but not the speech itself, therefore maintaining privacy of patient 702's communications. Furthermore, speech data signal 730 does not contain speech from person 716. Processing of speech data signal 730 occurs on cell phone 704, through the use of application software 706, to perform signal processing functions as described elsewhere herein. As depicted in FIG. 7, report 734 is presented to medical care provider 712 in the form of a text message displayed on screen 736 of cell phone 708.

Figure 8:
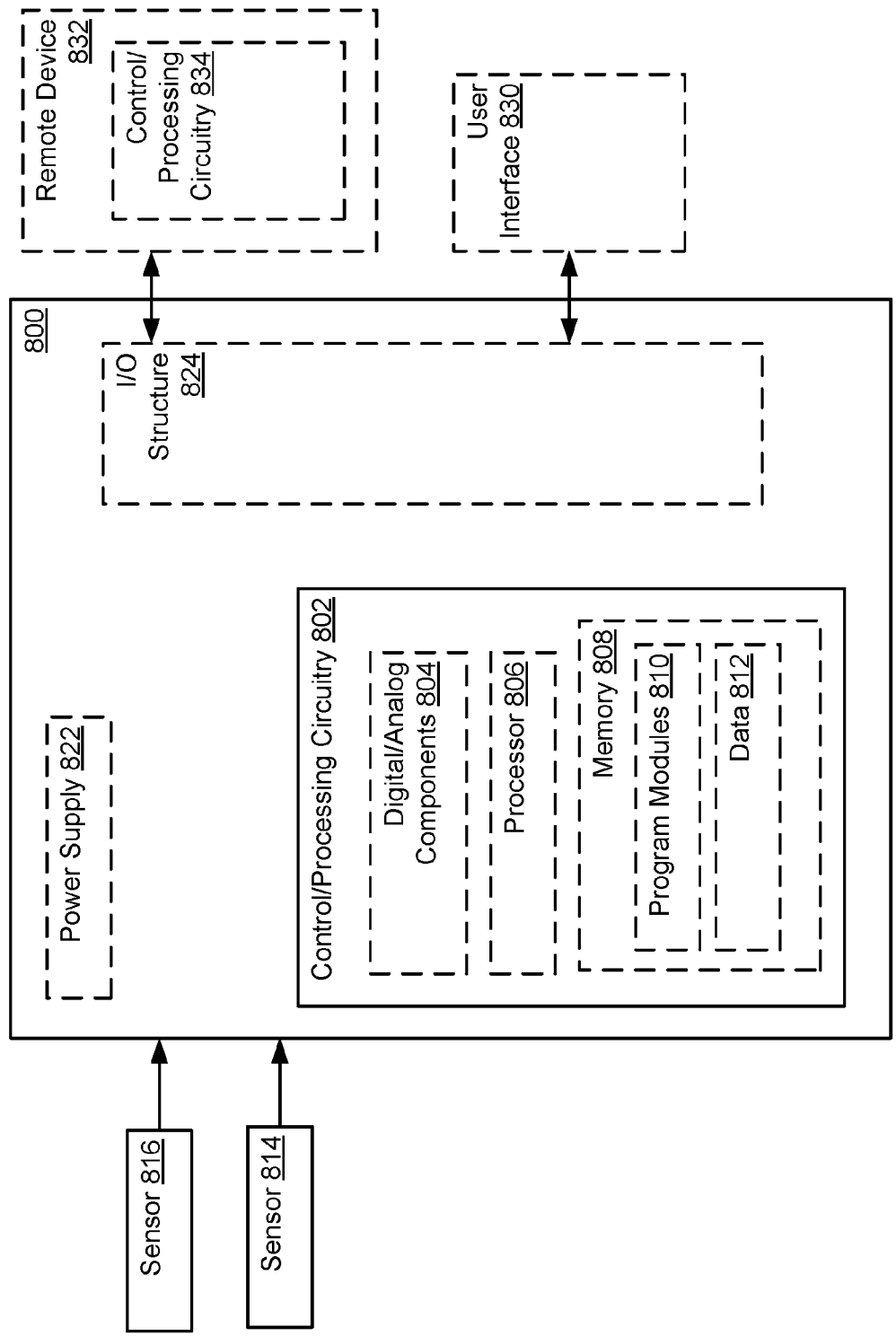
FIG. 8 is a generalized system block diagram.

FIG. 8 illustrates a generalized form of circuitry-based systems as depicted in FIGS. 1-7. Although specific embodiments are described herein, those skilled in the art will appreciate that methods and systems as described herein can be implemented in various ways. Reference is made herein to various circuitry subsystems (e.g., signal processing circuitry 122, compliance determination circuitry 144, and speech identification circuitry 140 in FIGS. 1-3) which may be considered to be control/processing circuitry. As an example of control/processing circuitry 802, local system 105 includes control circuitry for controlling at least one of the at least one audio sensor 114, the signal processing circuitry 122, and the at least one transmitting device 126. Control circuitry of local system 105 in various aspects control other system components and functions, e.g., communication circuitry 284, speech processor 202, notification circuitry 250, as well as data storage, communication, and input/output functions. As an example of control/processing circuitry 832, monitoring system 110 includes control circuitry for controlling at least one of the at least one receiving device 130, the speech identification circuitry 140, the compliance determination circuitry 144, and the reporting circuitry 148, and other system components.

As shown generically in FIG. 8, control/processing circuitry 802 includes any or all of digital and/or analog components 804, one or more processor 806 (e.g., a microprocessor), and memory 808, which may store one or more program module 810 and/or data 812. Systems as described herein may receive signals from various sensors (e.g., sensors 814 and 816 depicted in FIG. 8). System 800 may include other components as known to those skilled in the art, e.g., one or more power supply 822, and I/O structure 824. I/O structure 824 permits communication with various types of user interface devices (represented by user interface 830) and various types of remote device 832, which may have control/processing capability conferred by control/processing circuitry 834.

In a general sense, those skilled in the art will recognize that the various embodiments described herein can be implemented, individually and/or collectively, by various types of electrical circuitry having a wide range of electrical components such as hardware, software, firmware, and/or virtually any combination thereof. Electrical circuitry (including signal processing circuitry 122, speech identification circuitry 140, and compliance determination circuitry 144 in FIG. 1, for example) includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device, which may include various types of memory (e.g., random access, flash, read only, etc.), electrical circuitry forming a communications device (e.g., transmitting device 126 and receiving device 130) (e.g., a modem, communications switch, optical-electrical equipment, etc.), and/or any non-electrical analog thereto, such as optical or other analogs (e.g., graphene based circuitry). In an embodiment, the system is integrated in such a manner that the system operates as a unique system configured specifically for the function of monitoring treatment compliance, and any associated computing devices of the system operate as specific use computers for purposes of the claimed system, and not general use computers. In an embodiment, at least one of the associated computing devices of the system is hardwired with a specific ROM to instruct the at least one computing device. In a general sense, those skilled in the art will recognize that the various aspects described herein which can be implemented, individually and/or collectively, by a wide range of hardware, software, firmware, and/or any combination thereof can be viewed as being composed of various types of "electrical circuitry."

Those skilled in the art will recognize that at least a portion of the devices and/or processes described herein can be integrated into a data processing system. Those having skill in the art will recognize that a data processing system generally includes one or more of a system unit housing, a video display, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

As discussed in connection with FIG. 1, transmitting device 126 in local system 106 and receiving device 130 in monitoring system 110 are configured to provide a communication link between the two locations. In various aspects, transmitting device 126 and receiving device 130 provide a wireless communication link. A wireless communication link may also be established between monitoring system 110 and wireless device 376, as shown in FIG. 3. In various aspects, a wireless communication link includes at least one of a radio frequency, wireless network, cellular network, satellite, WiFi, BlueTooth, Wide Area Network, Local Area Network, or Body Area Network communication link. Various types of communication links are suitable for providing communication between two remote locations. Communication between locations remote from each other may take place over telecommunications networks, for example public or private Wide Area Network (WAN). In general, communication between remote locations is not considered to be suitably handled by technologies geared towards physically localized networks, e.g., Local Area Network (LAN) technologies operation at Layer ½ (such as the forms of Ethernet or WiFi). However, it will be appreciated that portions (but not the entirety) of communication networks used in remote communications may include technologies suitable for use in physically localized network, such as Ethernet or WiFi. In an aspect, system components are considered "remote" from each other if they are not within the same room, building, or campus. In an aspect, a remote system may include components separated by a few miles or more. Conversely, system components may be considered "local" to each other if they are located within the same room, building, or campus.

Figure 9:
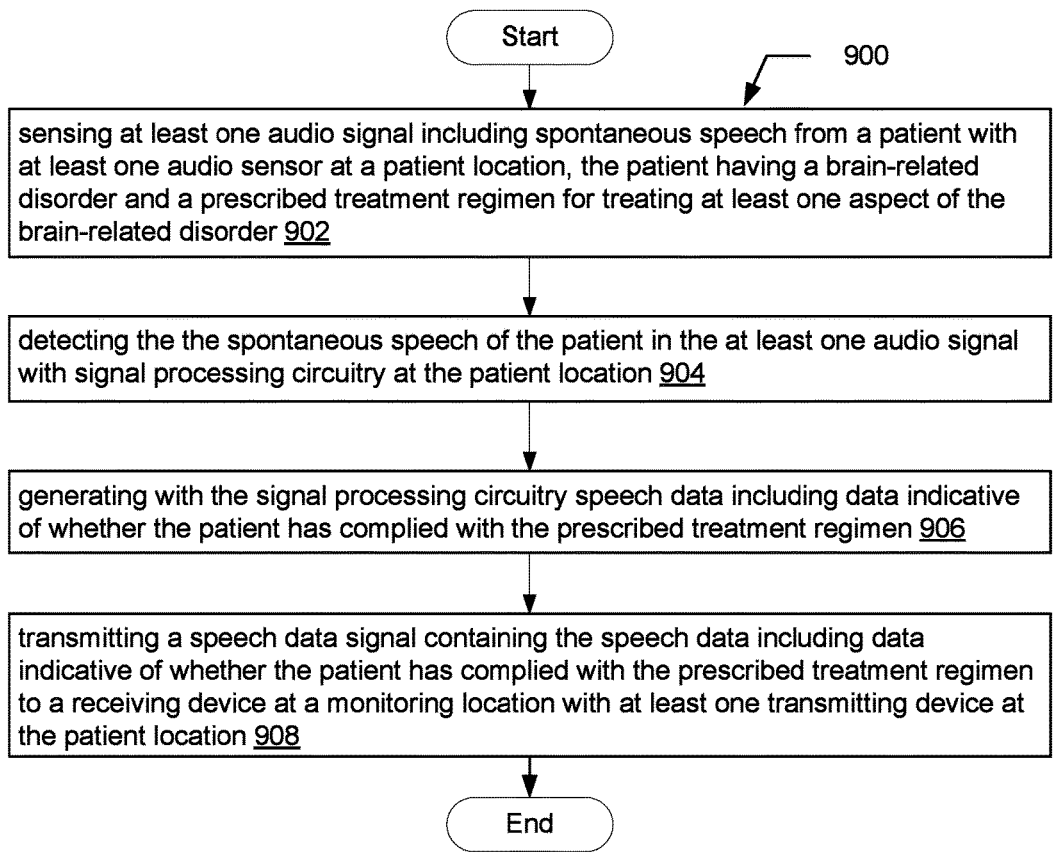
FIG. 9 is a flow diagram of a method of monitoring compliance of patient with a prescribed treatment regimen.

FIG. 9 is a flow diagram of a method 900 relating to monitoring of a patient at a patient location to determine compliance of the patient with a prescribed treatment regimen. Method 900 includes sensing at least one audio signal including spontaneous speech from a patient with at least one audio sensor at a patient location, the patient having a brain-related disorder and a prescribed treatment regimen for treating at least one aspect of the brain-related disorder, as indicated at 902; detecting spontaneous speech of the patient in the at least one audio signal with signal processing circuitry at the patient location, as indicated at 904; generating with the signal processing circuitry speech data including data indicative of whether the patient has complied with the prescribed treatment regimen, as indicated at 906; and transmitting a speech data signal containing the speech data including data indicative of whether the patient has complied with the prescribed treatment regimen to a receiving device at a monitoring location with at least one transmitting device at the patient location, as indicated at 908. Generation of a speech data signal containing speech data including data indicative of whether the patient has complied with the prescribed treatment regimen is carried out with a system as depicted in FIG. 2

FIGS. 10-18 depict variations and expansions of method 900 as shown in FIG. 9. In the methods depicted in FIGS. 10-18, steps 902-908 are as described generally in connection with FIG. 9. Here and elsewhere, method steps outlined with dashed lines represent steps that are included in some, but not all method aspects, and combinations of steps other than those specifically depicted in the figures are possible as would be known by those having ordinary skill in the relevant art.

Figure 10:
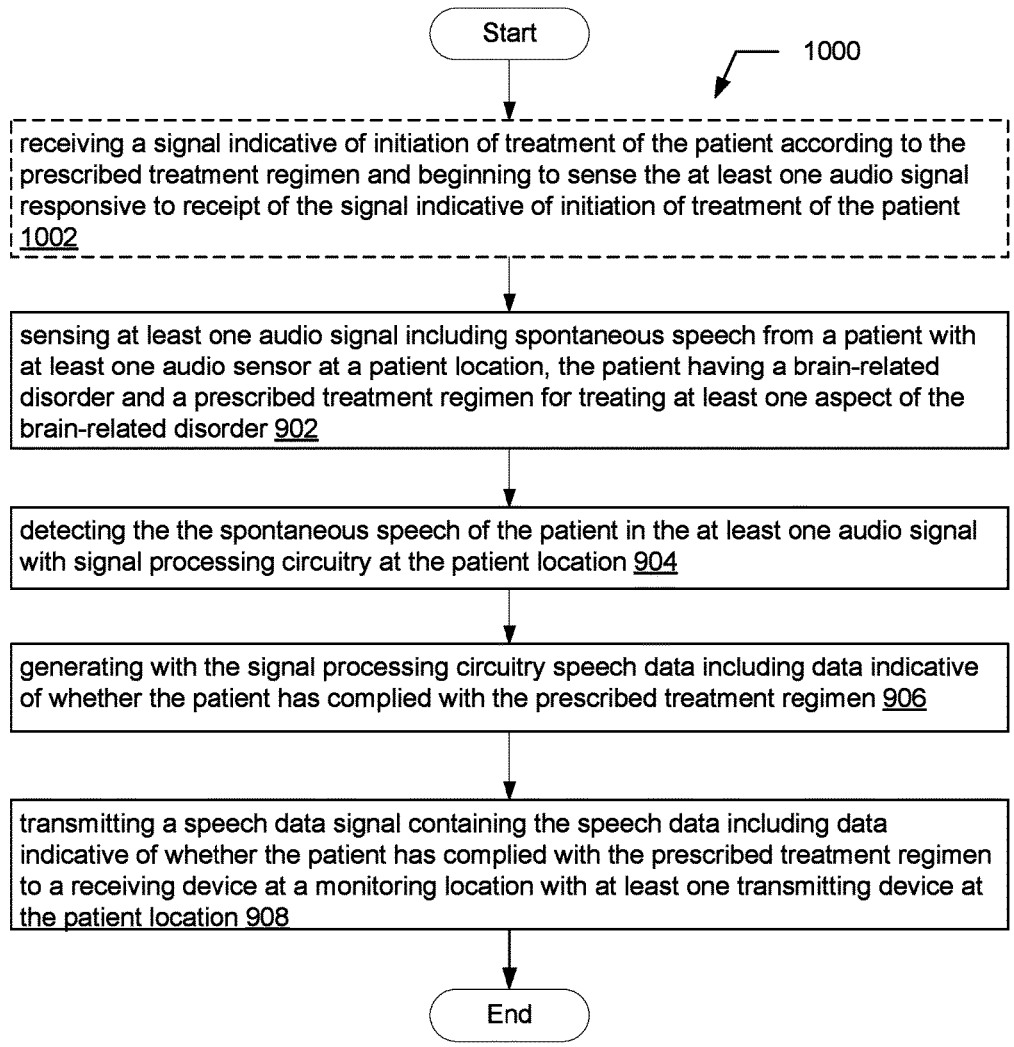
FIG. 10 is a flow diagram of further aspects of the method of FIG. 9.

FIG. 10 depicts method 1000, which includes steps 902-908 as described above, and also includes receiving a signal indicative of initiation of treatment of the patient according to the prescribed treatment regimen and beginning to sense the at least one audio signal responsive to receipt of the signal indicative of initiation of treatment of the patient, as indicated at 1002. As shown in FIG. 2, in an aspect a treatment signal 272 is transmitted to local system 106 from monitoring system 110, in response to an input indicating initiation of treatment from medical care provider 151, provided via a user input device (e.g., a keyboard or keypad), for example. In some aspects, patient 102 may provide an input via a user input device (e.g., a keyboard or keypad) to indicate that treatment has been initiated (e.g., that the patient took a dose of medication).

Figure 11:
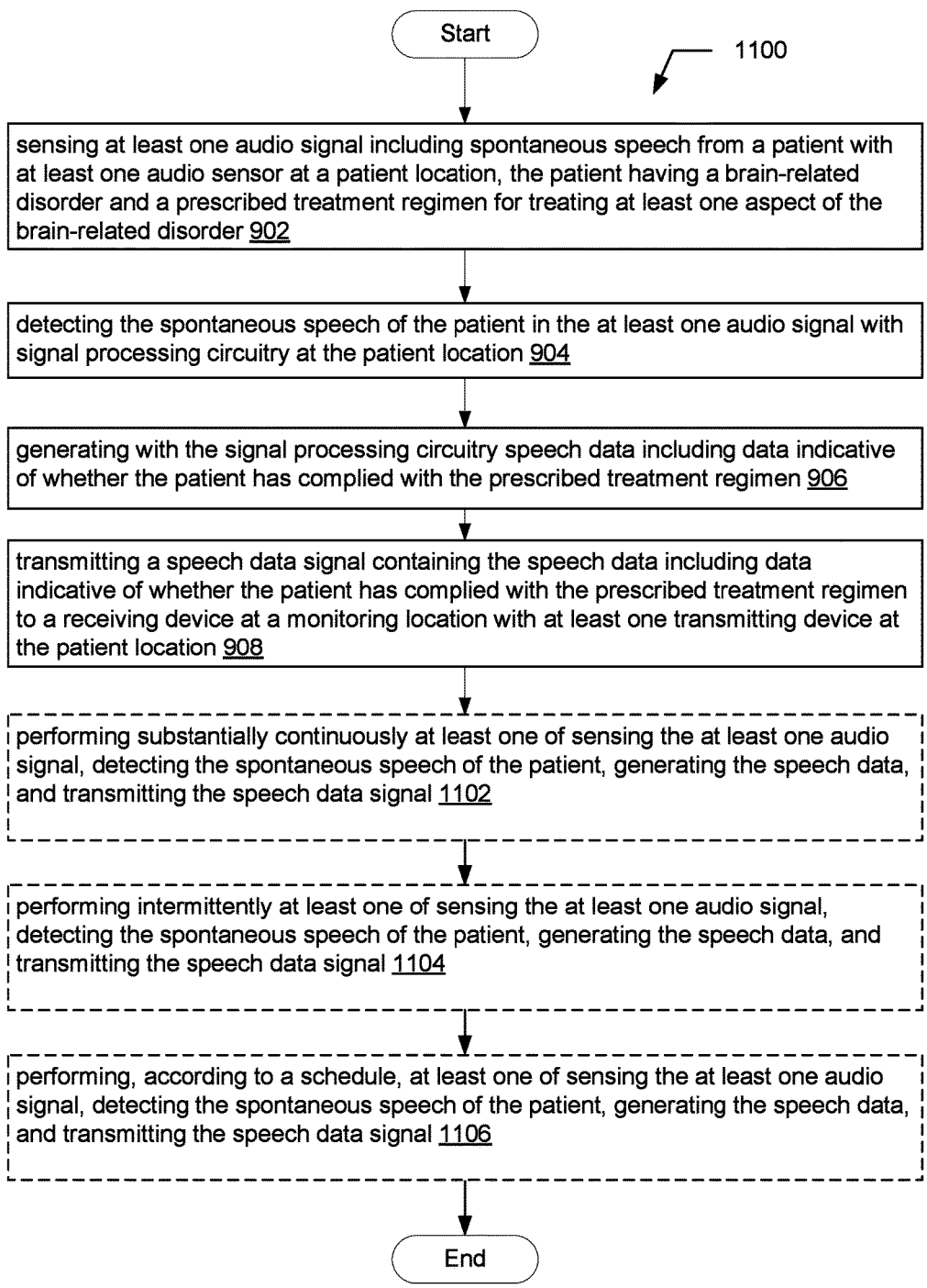
FIG. 11 is a flow diagram of further aspects of the method of FIG. 9.

FIG. 11 depicts a further method 1100, which includes performing substantially continuously at least one of sensing the at least one audio signal, detecting the spontaneous speech of the patient, generating the speech data, and transmitting the speech data signal, as indicated at 1102. Continuous monitoring may be appropriate, for example, in situations where the patient's condition is unstable and likely to change abruptly or dramatically, such that prompt detection and correction is desirable. In an aspect, method 1100 includes performing intermittently at least one of sensing the at least one audio signal, detecting the spontaneous speech of the patient, generating the speech data, and transmitting the speech data signal, as indicated at 1104. Intermittent sensing may be appropriate for patients whose condition is sufficiently stable that continuous monitoring is not required. Intermittent sensing may be event driven (for example, sensing can be performed when the patient uses a phone for communication, or when the patient uses a personal computer). In another aspect, method 1100 includes performing, according to a schedule, at least one of sensing the at least one audio signal, detecting the spontaneous speech of the patient, generating the speech data, and transmitting the speech data signal, as indicated at 1106. Sensing can be performed according to a schedule, under control of timing circuitry 244 in local system 106, as shown in FIG. 2. Timing circuitry 244 includes clock 274 and/or timer 276 and controls sensing according to stored schedule 278, for example by sending an interrupt to initiate sensing at the time or times specified by schedule 278, based on time from clock 274/timer 276. Similarly, timing may be controlled by timing circuitry 386 in monitoring system 110, according to schedule 398, based on time from clock 388 and/or timer 396.

Figure 12:
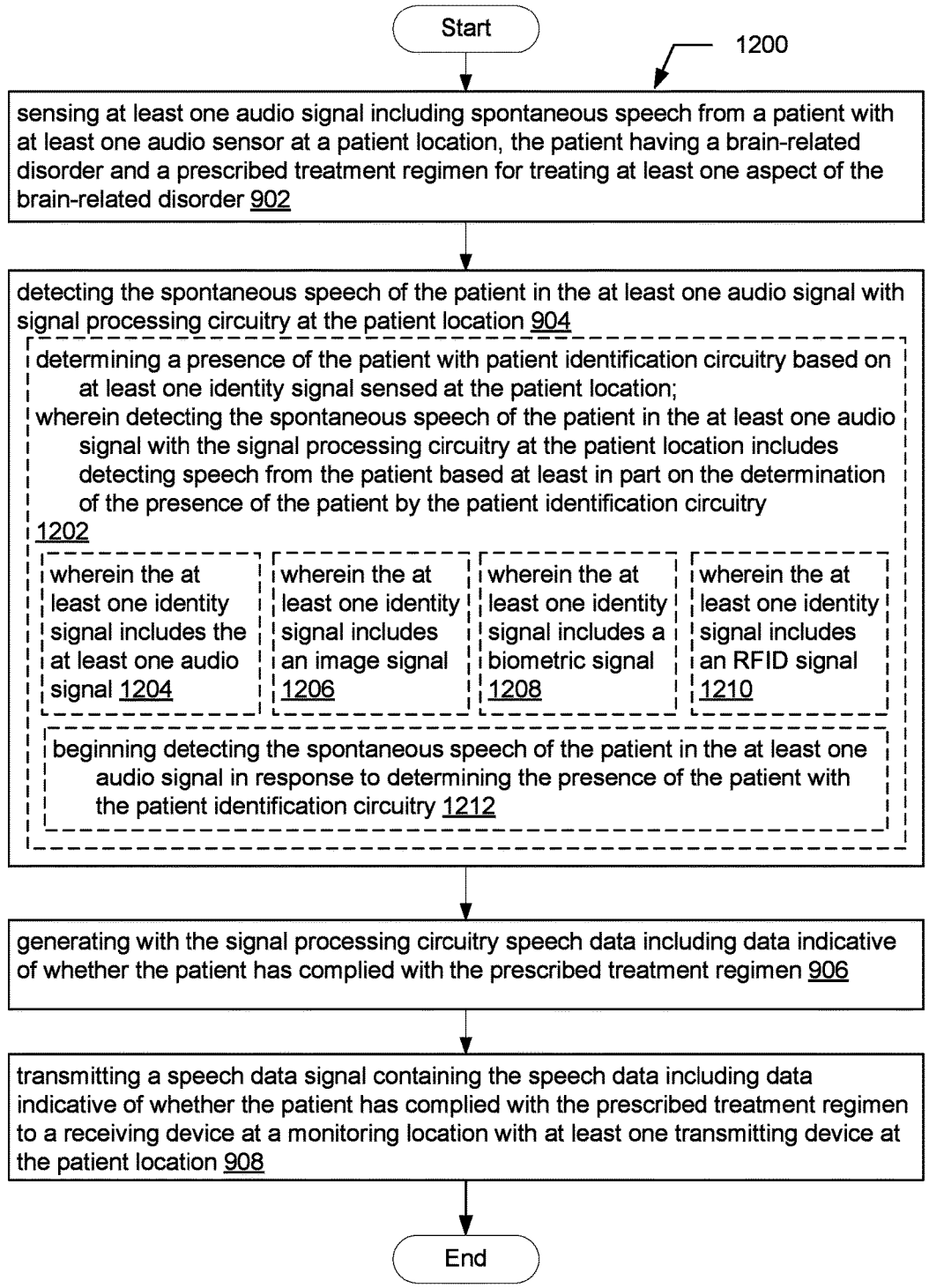
FIG. 12 is a flow diagram of further aspects of the method of FIG. 9.

As shown in FIG. 12, in another aspect, method 1200 includes determining a presence of the patient with patient identification circuitry based on at least one identity signal sensed at the patient location, wherein detecting spontaneous speech of the patient in the at least one audio signal with the signal processing circuitry at the patient location includes detecting speech from the patient based at least in part on the determination of the presence of the patient by the patient identification circuitry, as indicated at 1202. The identity signal may include, for example, the audio signal, as indicated at 1204; an image signal, as indicated at 1206; a biometric signal, as indicated at 1208; or an RFID signal, as indicated at 1210. In an aspect, method 1200 includes beginning detecting the spontaneous speech of the patient in the at least one audio signal in response to determining the presence of the patient with the patient identification circuitry, as indicated at 1212. For example, in the embodiment of FIG. 6, in an aspect, detection of spontaneous speech from patient 602 is initiated in response to determining the presence of patient 602 based on recognition of patient 602 in image 630, using one or both of gait or facial recognition techniques.

Figure 13:
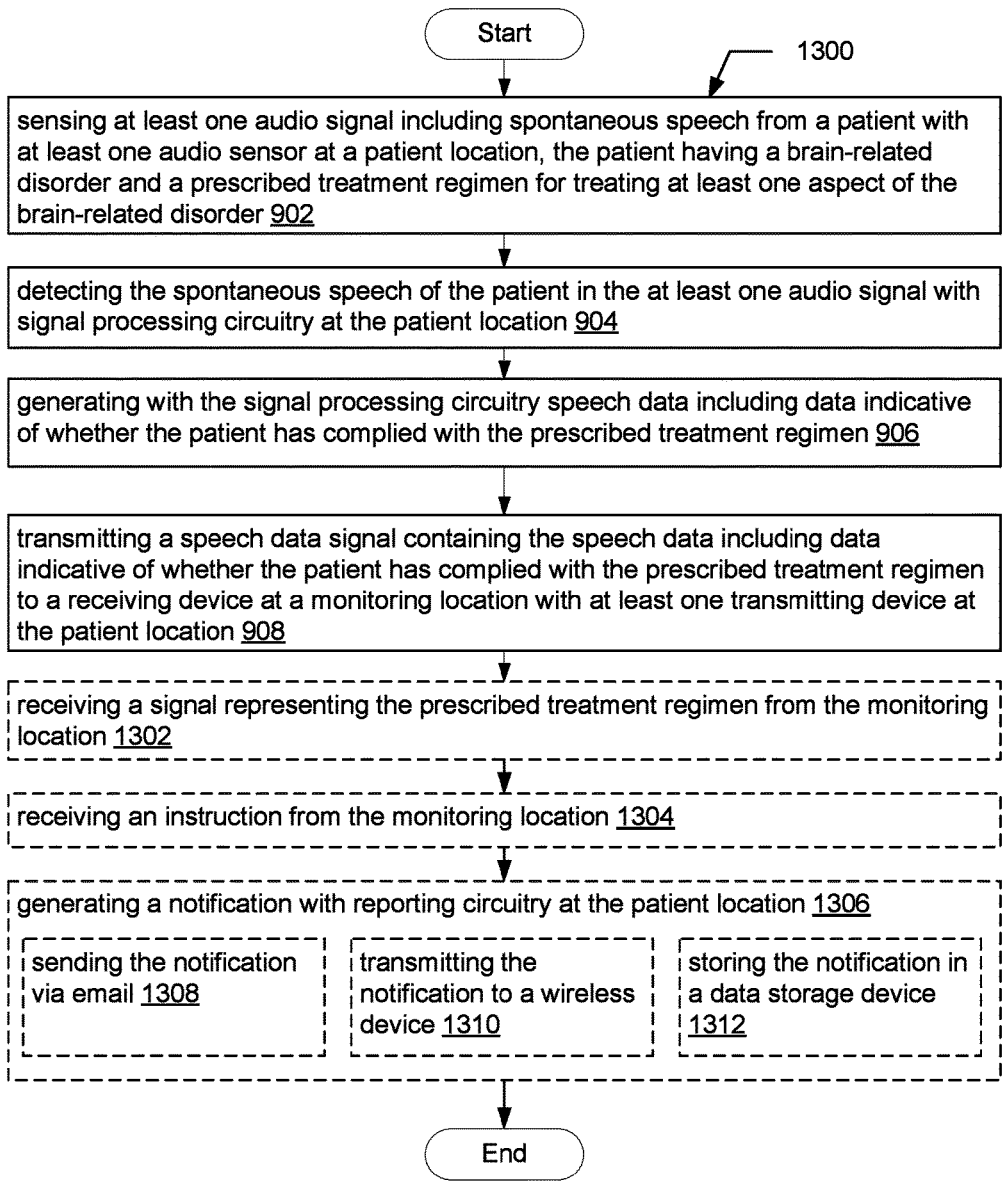
FIG. 13 is a flow diagram of further aspects of the method of FIG. 9.

As shown in FIG. 13, in various aspects a method 1300 includes receiving a signal representing the prescribed treatment regimen from the monitoring location, as indicated at 1302 (e.g., prescription information signal 338 in FIGS. 2 and 3); receiving an instruction from the monitoring location, as indicated at 1304 (e.g., instruction 399 in FIGS. 2 and 3); and generating a notification with notification circuitry at the patient location, as indicated at 1306; and may also include one or more of sending the notification via email, as indicated at 1308; transmitting the notification to a wireless device, as indicated at 1310; and storing the notification in a data storage device, as indicated at 1312 (see, e.g., discussion of notification generation by notification circuitry 250 in FIG. 2).

Figure 14:
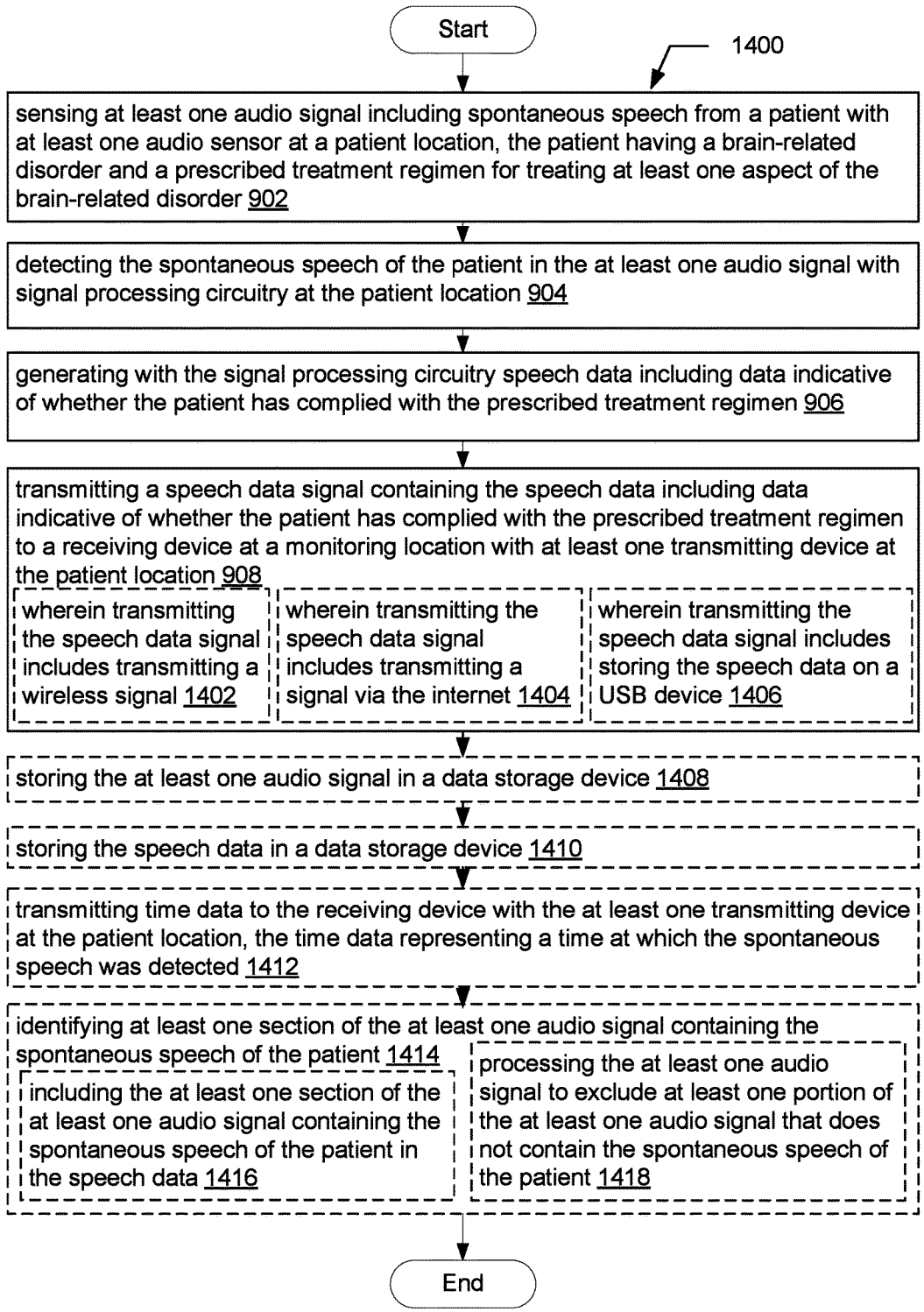
FIG. 14 is a flow diagram of further aspects of the method of FIG. 9.

As shown in FIG. 14, in various aspects of a method 1400, transmitting the speech data signal includes transmitting a wireless signal, as indicated at 1402; transmitting a signal via the internet, as indicated at 1404; or storing the speech data on a USB device, as indicated at 1406. See, e.g., transmitting device 126, as depicted and described in connection with FIG. 2. Method 1400 may include storing the at least one audio signal in a data storage device, as indicated at 1408; storing the speech data in a data storage device, as indicated at 1410 (e.g., data storage device 200 in FIG. 2); or transmitting time data to the receiving device with the at least one transmitting device at the patient location, the time data representing a time at which the spontaneous speech was detected, as indicated at 1412. Method 1400 may include identifying at least one section of the at least one audio signal containing spontaneous speech of the patient, as indicated at 1414. Method 1400 may then also include one or both of including the at least one section of the at least one audio signal containing spontaneous speech of the patient in the speech data, as indicated at 1416, and processing the at least one audio signal to exclude at least one portion of the at least one audio signal that does not contain the spontaneous speech of the patient, as indicated at 1418.

Figure 15:
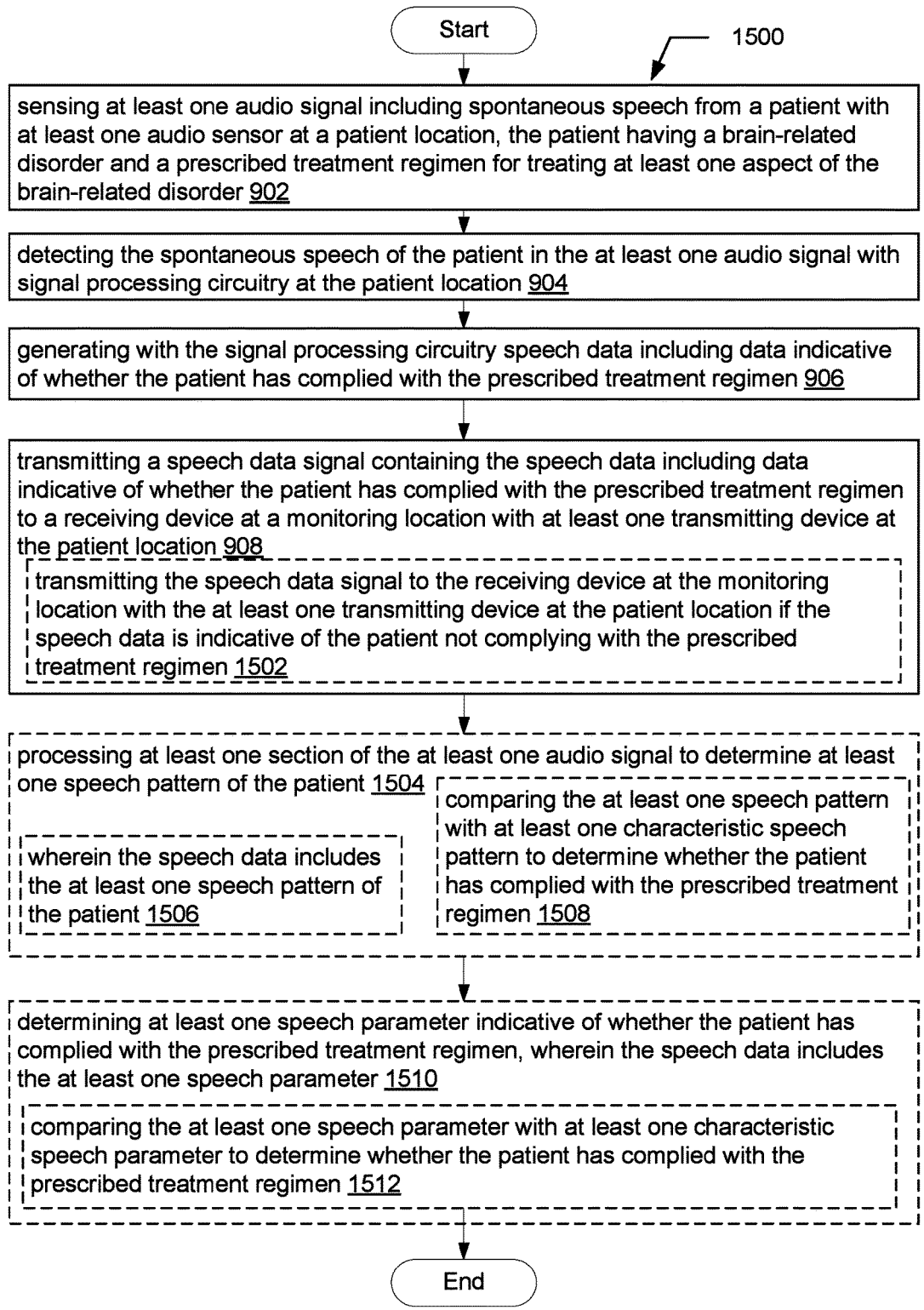
FIG. 15 is a flow diagram of further aspects of the method of FIG. 9.

FIG. 15 depicts a method 1500, which in an aspect includes transmitting the speech data signal to the receiving device at the monitoring location with the at least one transmitting device at the patient location if the speech data is indicative of the patient not complying with the prescribed treatment regimen, as indicated at 1502. Such a notification allows a medical care provider to take action to correct or respond to the patient's lack of compliance when such notification is received, without the need for the medical care provider to monitor the patient's status continuously. In addition, in an aspect, method 1500 includes processing at least one section of the at least one audio signal to determine at least one speech pattern of the patient, as indicated at 1504. The speech data may then include the at least one speech pattern of the patient, as indicated at 1506. In addition, method 1500 may also include comparing the at least one speech pattern with at least one characteristic speech pattern to determine whether the patient has complied with the prescribed treatment regimen, as indicated at 1508.

In another aspect, method 1500 includes determining at least one speech parameter indicative of whether the patient has complied with the prescribed treatment regimen, wherein the speech data includes the at least one speech parameter, as indicated at 1510, and may then also include comparing the at least one speech parameter with at least one characteristic speech parameter to determine whether the patient has complied with the prescribed treatment regimen, as indicated at 1512.

Figure 16:
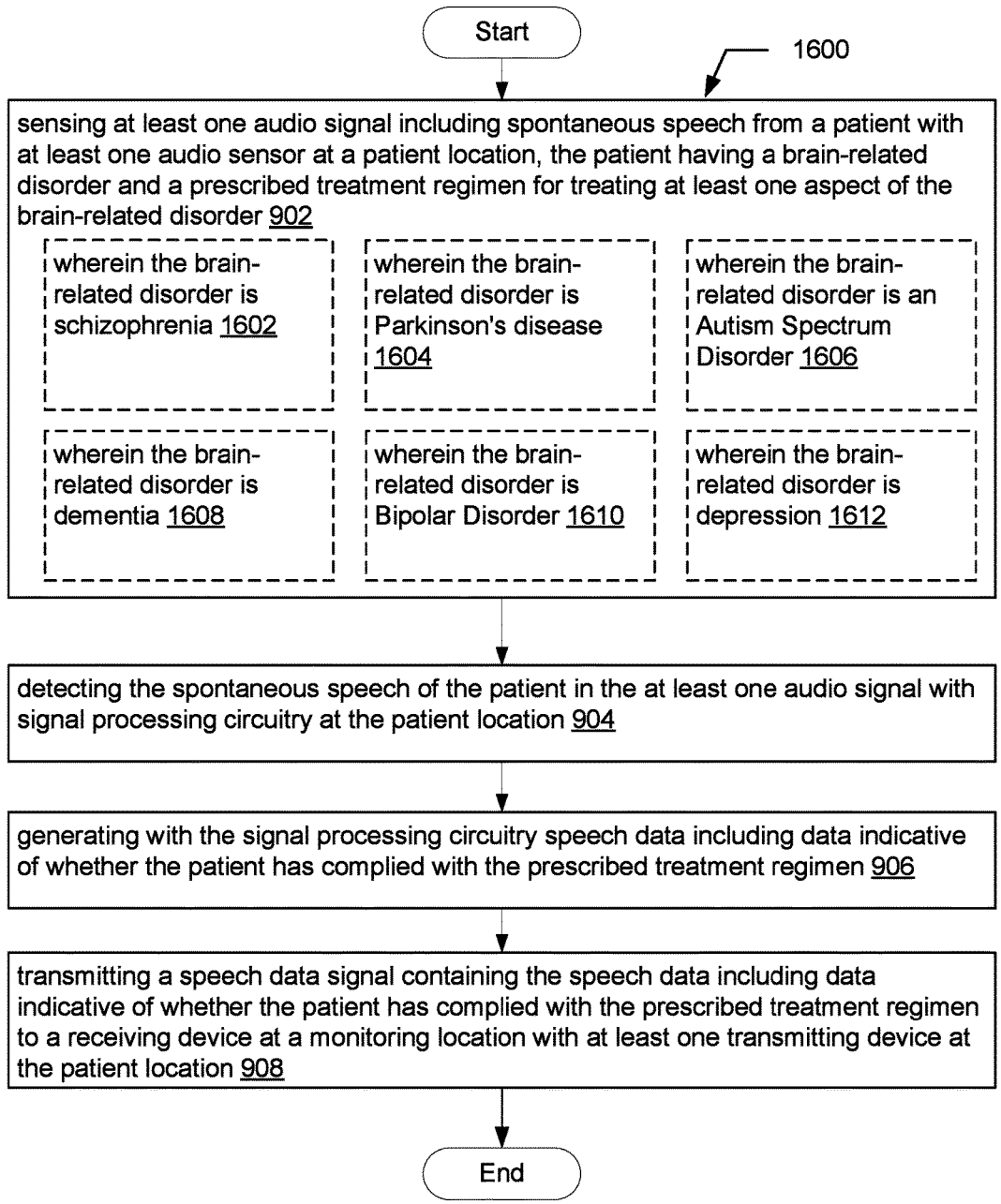
FIG. 16 is a flow diagram of further aspects of the method of FIG. 9.

As shown in FIG. 16, various aspects of a method 1600, the brain-related disorder is schizophrenia, as indicated at 1602; Parkinson's disease, as indicated at 1604; an Autism Spectrum Disorder, as indicated at 1606; dementia, as indicated at 1608; Bipolar Disorder, as indicated at 1610; or depression, as indicated at 1612.

In an aspect a brain-related disorder is a mental disorder, psychological disorder, or psychiatric disorder. A mental disorder, psychological disorder, or psychiatric disorder can include, for example, a psychological pathology, psychopathology, psychosocial pathology, social pathology, or psychobiology disorder. A mental disorder, psychological disorder, or psychiatric disorder can be any disorder categorized in any Diagnostic and Statistical Manual (DSM) or International Statistical Classification of Diseases (ICD) Classification of Mental and Behavioural Disorders text, and may be, for example and without limitation, a neurodevelopmental disorder (e.g., autism spectrum disorder or attention-deficit/hyperactivity disorder), a psychotic disorder (e.g., schizophrenia), a mood disorder, a bipolar disorder, a depressive disorder, an anxiety disorder, an obsessive-compulsive disorder, a trauma- or stressor-related disorder, a dissociative disorder, a somatic symptom disorder, an eating disorder, an impulse-control disorder, a substance-related or addictive disorder, a personality disorder (e.g., narcissistic personality disorder or antisocial personality disorder), a neurocognitive disorder, a major or mild neurocognitive disorder (e.g., one due to Alzheimer's disease, traumatic brain injury, HIV infection, prion disease, Parkinson's disease, Huntington's disease, or substance/medication). A mental disorder, psychological disorder, or psychiatric disorder can be any disorder described by the NIH National Institute of Mental Health (NIMH) Research Domain Criteria Project and may include a biological disorder involving brain circuits that implicate specific domains of cognition, emotion, or behavior. In an aspect, a brain-related disorder includes a serious mental illness or serious emotional disturbance.

In various aspects, a brain-related disorder includes a serious mental illness or serious emotional disturbance, a mental disorder, psychological disorder, or psychiatric disorder.

In an aspect a brain disorder is a traumatic disorder, such as a traumatic brain injury. Traumatic brain injury-induced disorders may present with dysfunction in cognition, communication, behavior, depression, anxiety, personality changes, aggression, acting out, or social inappropriateness. See, e.g., Jeffrey Nicholl and W. Curt LaFrance, Jr., "Neuropsychiatric Sequelae of Traumatic Brain Injury," Semin Neurol. 2009, 29(3):247-255.

In an aspect a brain-related disorder is a lesion-related disorder. A brain lesion can include, for example and without limitation, a tumor, an aneurysm, ischemic damage (e.g., from stroke), an abscess, a malformation, inflammation, or any damage due to trauma, disease, or infection. An example of a lesion-related disorder is a disorder associated with a right-hemisphere lesion.

In an aspect a brain disorder is a neurological disorder. A neurological disorder may be, for example and without limitation, Alzheimer's disease, a brain tumor, a developmental disorder, epilepsy, a neurogenetic disorder, Parkinson's disease, Huntington's disease, a neurodegenerative disorder, stroke, traumatic brain injury or a neurological consequence of AIDS. Neurological disorders are described on the website of the National Institutes of Health (NIH) National Institute of Neurological Disorders and Stroke (NINDS)

Figure 17:
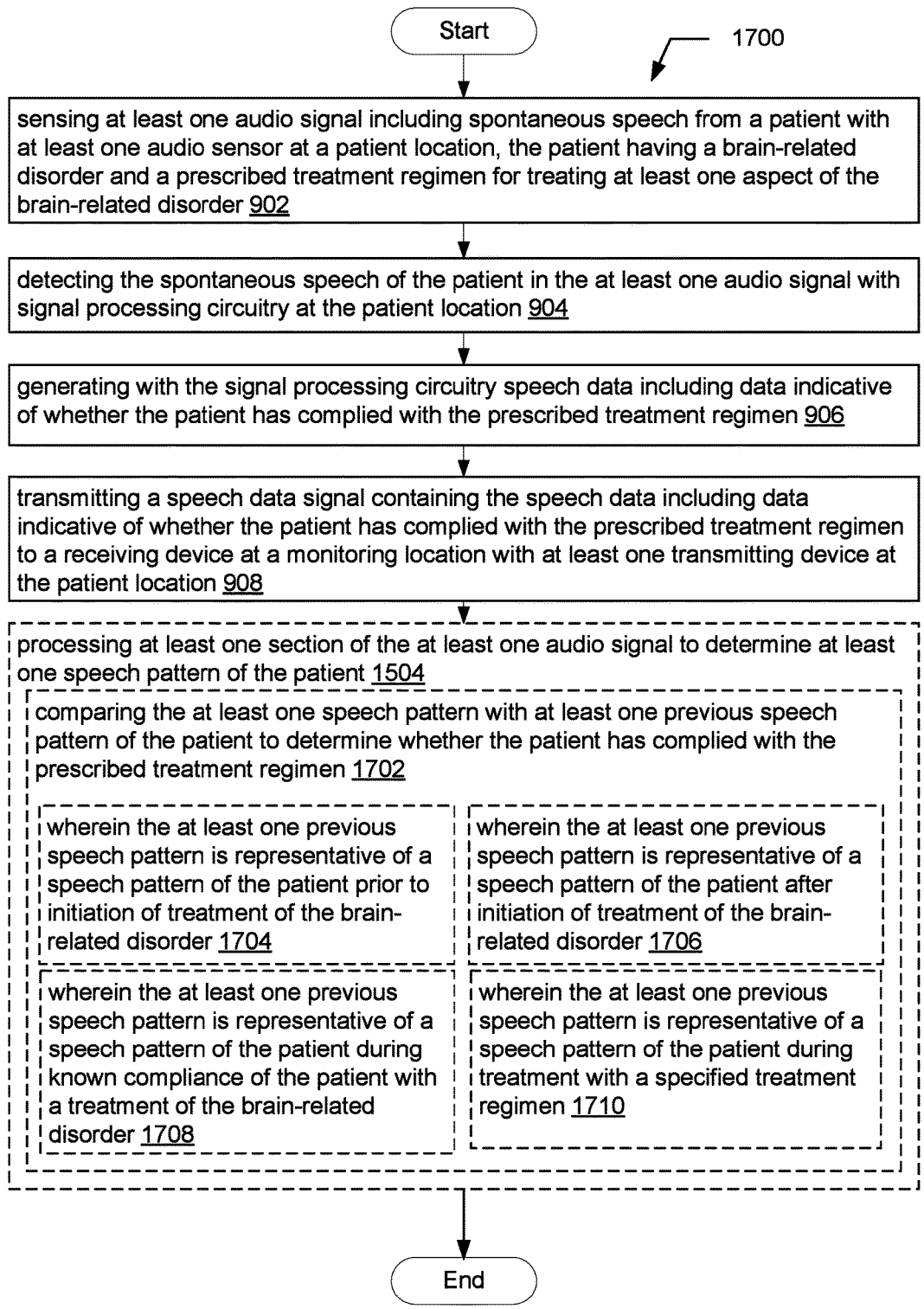
FIG. 17 is a flow diagram of further aspects of the method of FIG. 9.

FIG. 17 shows a method 1700 that includes processing at least one section of the at least one audio signal to determine at least one speech pattern of the patient, as indicated at 1504, and in addition, comparing the at least one speech pattern with at least one previous speech pattern of the patient to determine whether the patient has complied with the prescribed treatment regimen, as indicated at 1702. For example, in various aspects, the at least one previous speech pattern is representative of a speech pattern of the patient prior to initiation of treatment of the brain-related disorder, as indicated at 1704; a speech pattern of the patient after initiation of treatment of the brain-related disorder, as indicated at 1706; a speech pattern of the patient during known compliance of the patient with a treatment of the brain-related disorder, as indicated at 1708; or a speech pattern of the patient during treatment with a specified treatment regimen, as indicated at 1710.

Figure 18:
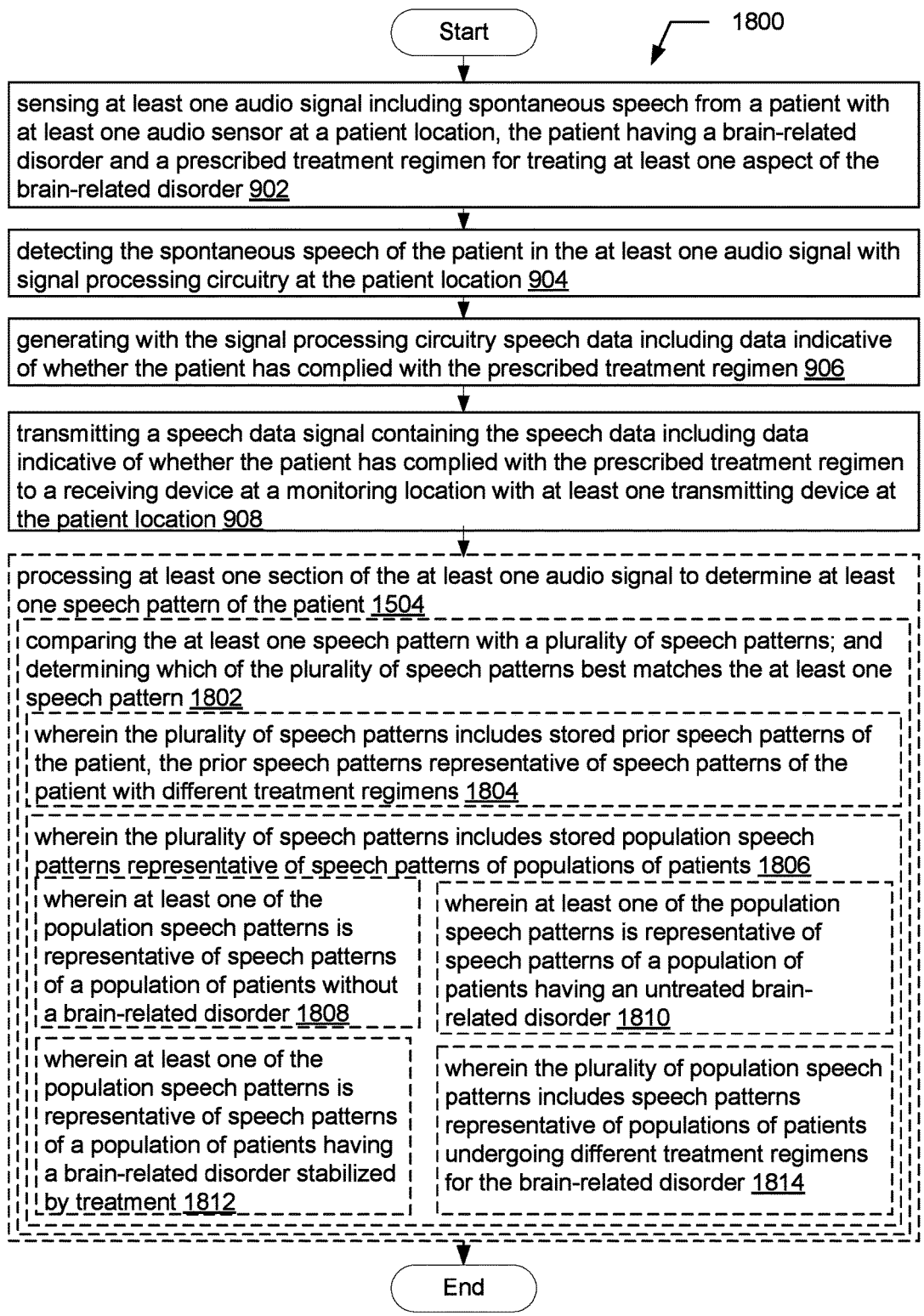
FIG. 18 is a flow diagram of further aspects of the method of FIG. 9.

As shown in FIG. 18, in an aspect, a method 1800 includes processing at least one section of the at least one audio signal to determine at least one speech pattern of the patient, as indicated at 1504, and in addition, comparing the at least one speech pattern with a plurality of speech patterns and determining which of the plurality of speech patterns best matches the at least one speech pattern, as indicated at 1802. In an aspect, the plurality of speech patterns includes stored prior speech patterns of the patient, the prior speech patterns representative of speech patterns of the patient with different treatment regimens, as indicated at 1804. In another aspect, the plurality of speech patterns includes stored population speech patterns representative of speech patterns of populations of patients, as indicated at 1806. In various aspects, at least one of the population speech patterns is representative of speech patterns of a population of patients without a brain-related disorder, as indicated at 1808; a population of patients having an untreated brain-related disorder, as indicated at 1810; or a population of patients having a brain-related disorder stabilized by treatment, as indicated at 1812. In an aspect, the plurality of population speech patterns includes speech patterns representative of populations of patients undergoing different treatment regimens for a brain-related disorder, as indicated at 1814.

In various embodiments, methods as described herein may be performed according to instructions implementable in hardware, software, and/or firmware. Such instructions may be stored in non-transitory machine-readable data storage media, for example. Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically oriented hardware, software, and or firmware.

In some implementations described herein, logic and similar implementations may include software or other control structures. Electrical circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components.

Implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

This detailed description sets forth various embodiments of devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to non-transitory machine-readable data storage media such as a recordable type medium such as a floppy disk, a hard disk drive, a Compact Disc (CD), a Digital Video Disk (DVD), a digital tape, a computer memory, etc. A signal bearing medium may also include transmission type medium such as a digital and/or an analog communication medium (e.g., a fiber optic cable, a waveguide, a wired communications link, a wireless communication link (e.g., transmitter, receiver, transmission logic, reception logic, etc.) and so forth).

Figure 19:
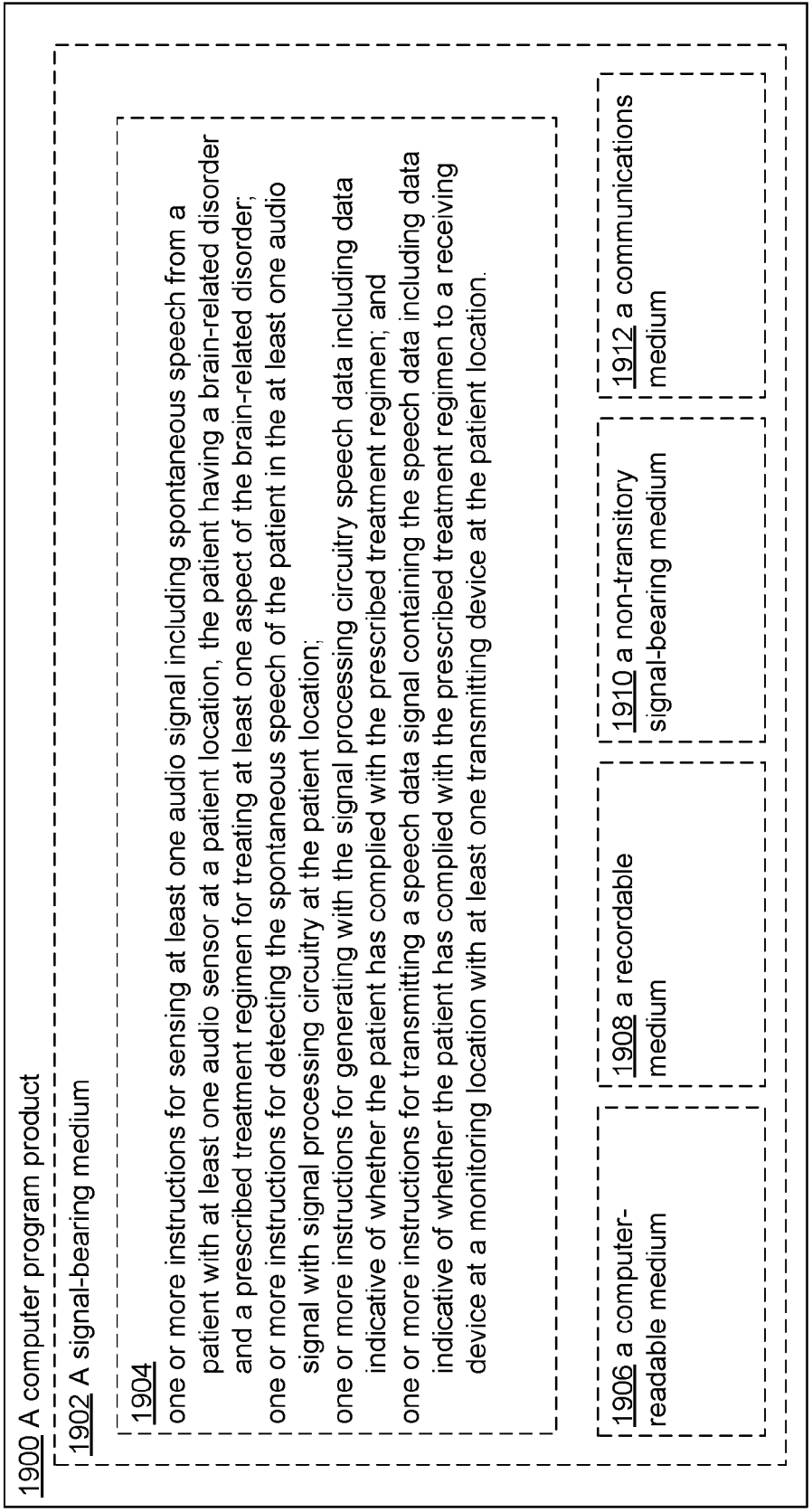
FIG. 19 is a block diagram of a computer program product including a signal-bearing medium.

FIG. 19 is a block diagram of a computer program product 1900 for implementing a method as described in connection with FIG. 9. Computer program product 1900 includes a signal-bearing medium 1902 bearing: one or more instructions for sensing at least one audio signal including spontaneous speech from a patient with at least one audio sensor at a patient location, the patient having a brain-related disorder and a prescribed treatment regimen for treating at least one aspect of the brain-related disorder; one or more instructions for detecting spontaneous speech of the patient in the at least one audio signal with signal processing circuitry at the patient location; one or more instructions for generating with the signal processing circuitry speech data including data indicative of whether the patient has complied with the prescribed treatment regimen; and one or more instructions for transmitting a speech data signal containing the speech data including data indicative of whether the patient has complied with the prescribed treatment regimen to a receiving device at a monitoring location with at least one transmitting device at the patient location, as indicated at 1904. Signal-bearing medium 1902 may be, for example, a computer-readable medium 1906, a recordable medium 1908, a non-transitory signal-bearing medium 1910, or a communications medium 1912, examples of which are described herein above.

Figure 20:
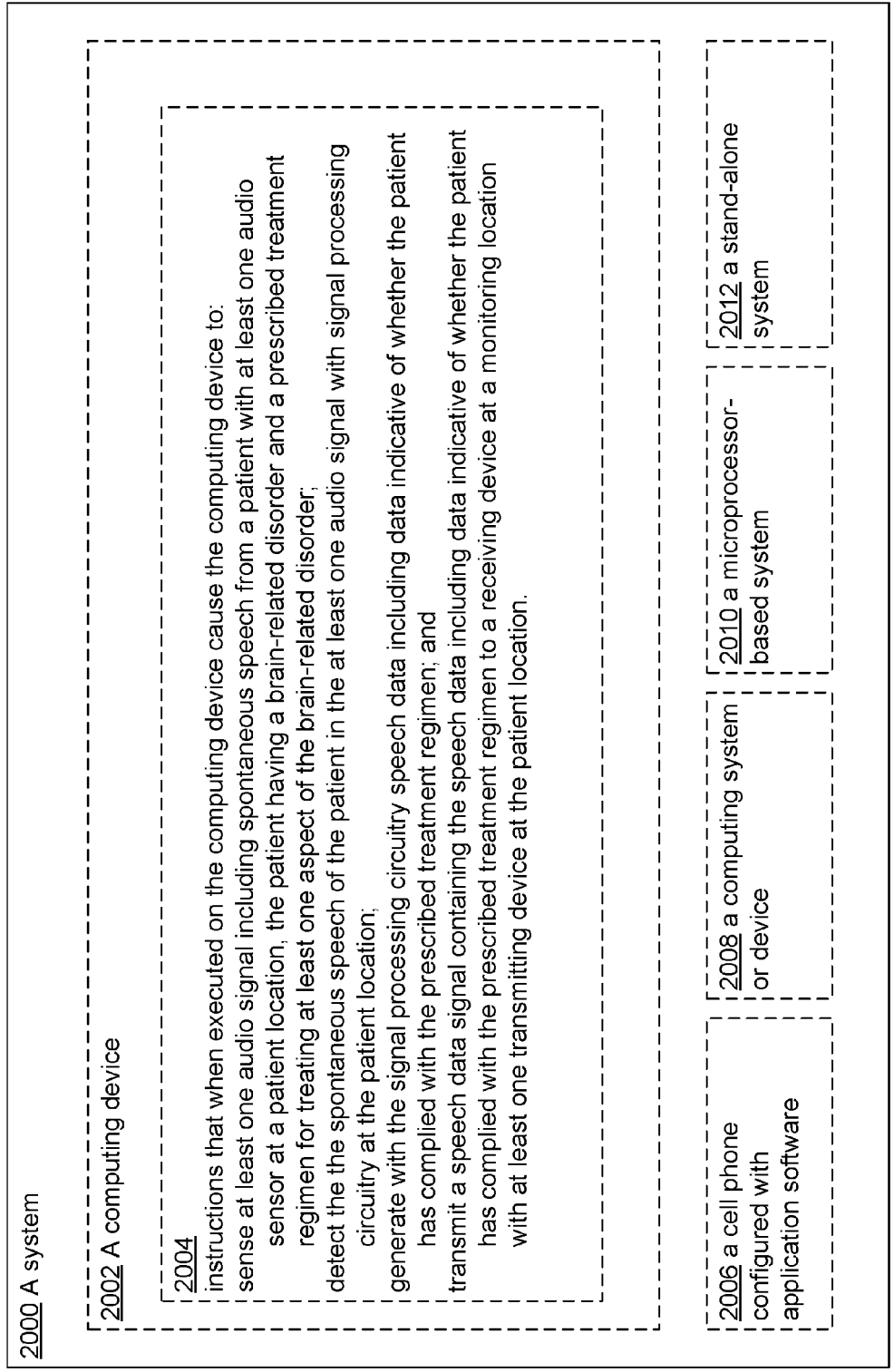
FIG. 20 is a block diagram of a system including a computing device.

FIG. 20 is a block diagram of a system 2000 for implementing a method as described in connection with FIG. 9. System 2000 includes a computing device 2002 and instructions that when executed on the computing device cause the computing device to sense at least one audio signal including spontaneous speech from a patient with at least one audio sensor at a patient location, the patient having a brain-related disorder and a prescribed treatment regimen for treating at least one aspect of the brain-related disorder; detect spontaneous speech of the patient in the at least one audio signal with signal processing circuitry at the patient location; generate with the signal processing circuitry speech data including data indicative of whether the patient has complied with the prescribed treatment regimen; and transmit a speech data signal containing the speech data including data indicative of whether the patient has complied with the prescribed treatment regimen to a receiving device at a monitoring location with at least one transmitting device at the patient location, as indicated at 2004. System 2000 may be, for example, a cell phone configured with application software 2006, a computing system or device 2008, a microprocessor-based system 2010, and/or a stand-alone system 2012.

Figure 21:
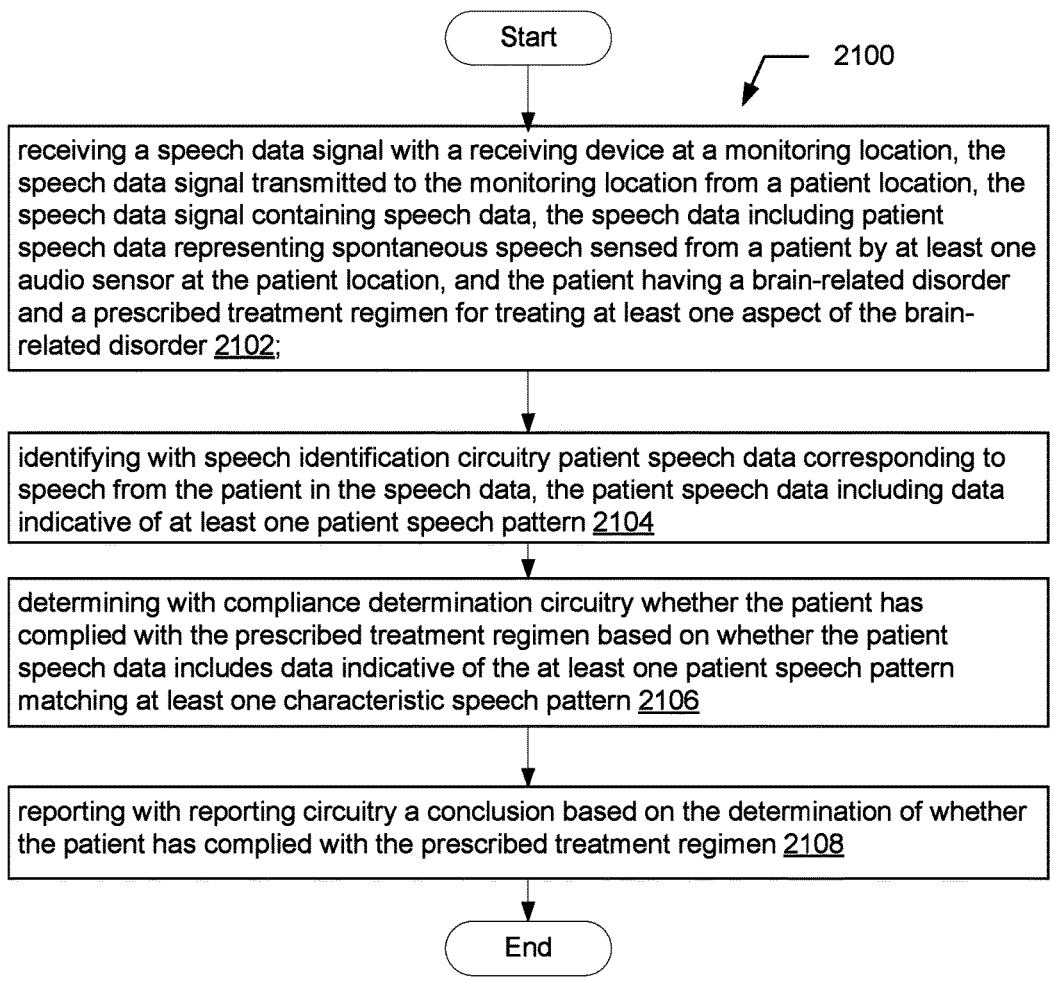
FIG. 21 is a flow diagram of a method of monitoring compliance of patient with a prescribed treatment regimen.

FIG. 21 is a flow diagram of a method 2100 of monitoring compliance of a patient with a prescribed treatment regimen, including method aspects occurring at or associated with a monitoring location, e.g., monitoring location 112 in FIG. 1. Method 2100 includes receiving a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at a patient location, and the patient having a brain-related disorder and a prescribed treatment regimen for treating at least one aspect of the brain-related disorder, as indicated at 2102; identifying with speech identification circuitry patient speech data corresponding to speech from the patient in the speech data, the patient speech data including data indicative of at least one patient speech pattern, as indicated at 2104; determining with compliance determination circuitry whether the patient has complied with the prescribed treatment regimen based on whether the patient speech data includes data indicative of the at least one patient speech pattern matching at least one characteristic speech pattern, as indicated at 2106; and reporting with reporting circuitry a conclusion based on the determination of whether the patient has complied with the prescribed treatment regimen, as indicated at 2108.

FIGS. 22-32 depict variations and expansions of method 2100 as shown in FIG. 21. In the methods depicted in FIGS. 22-32, steps 2102-2108 are as described generally in connection with FIG. 21. Here and elsewhere, method steps outlined with dashed lines represent steps that are included in some, but not all method aspects, and combinations of steps other than those specifically depicted in the figures are possible as would be known by those having ordinary skill in the relevant art.

Figure 22:
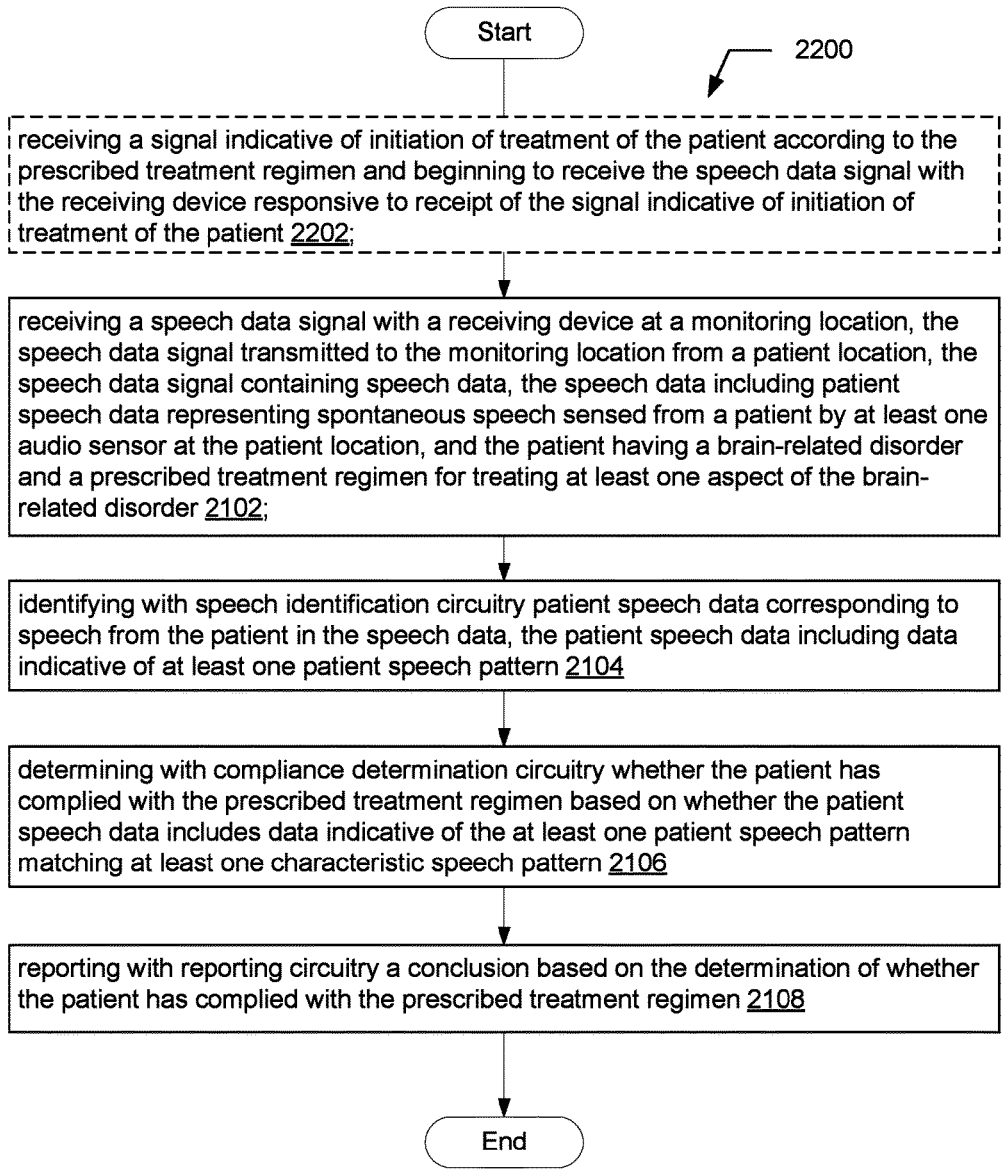
FIG. 22 is a flow diagram of further aspects of the method of FIG. 22.

As shown in FIG. 22, a method 2200 includes receiving a signal indicative of initiation of treatment of the patient according to the treatment regimen and beginning to receive the speech data signal with the receiving device responsive to receipt of the signal indicative of initiation of treatment of the patient, as indicated at 2202.

Figure 23:
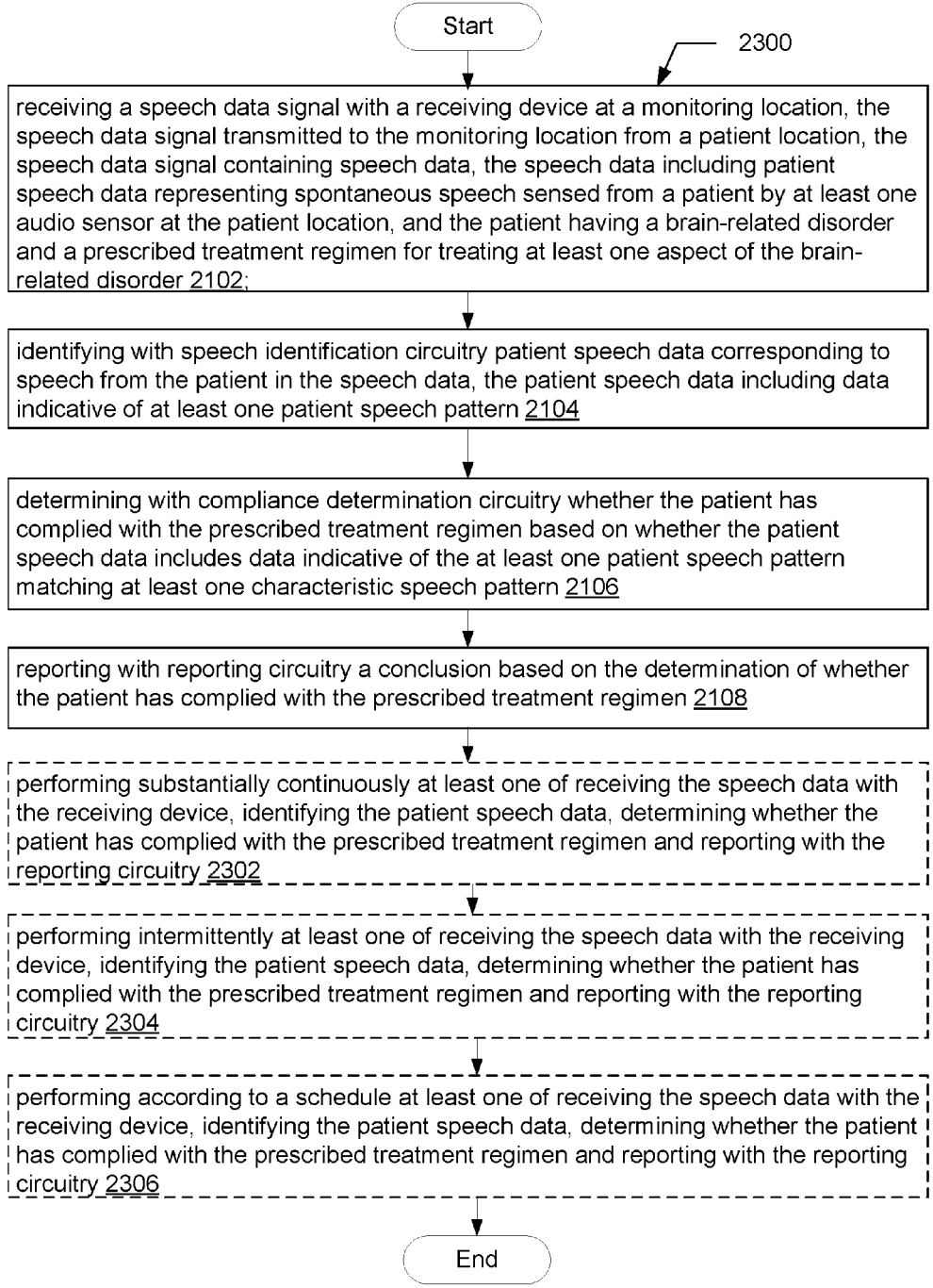
FIG. 23 is a flow diagram of further aspects of the method of FIG. 22.

As shown in FIG. 23, in an aspect, a method 2300 includes performing substantially continuously at least one of receiving the speech data with the receiving device, identifying the patient speech data, determining whether the patient has complied with the prescribed treatment regimen and reporting with the reporting circuitry, as indicated at 2302. In another aspect, method 2300 includes performing intermittently at least one of receiving the speech data with the receiving device, identifying the patient speech data, determining whether the patient has complied with the prescribed treatment regimen and reporting with the reporting circuitry, as indicated at 2304. In another aspect, method 2300 includes performing according to a schedule at least one of receiving the speech data with the receiving device, identifying the patient speech data, determining whether the patient has complied with the prescribed treatment regimen and reporting with the reporting circuitry, as indicated at 2306.

Figure 24:
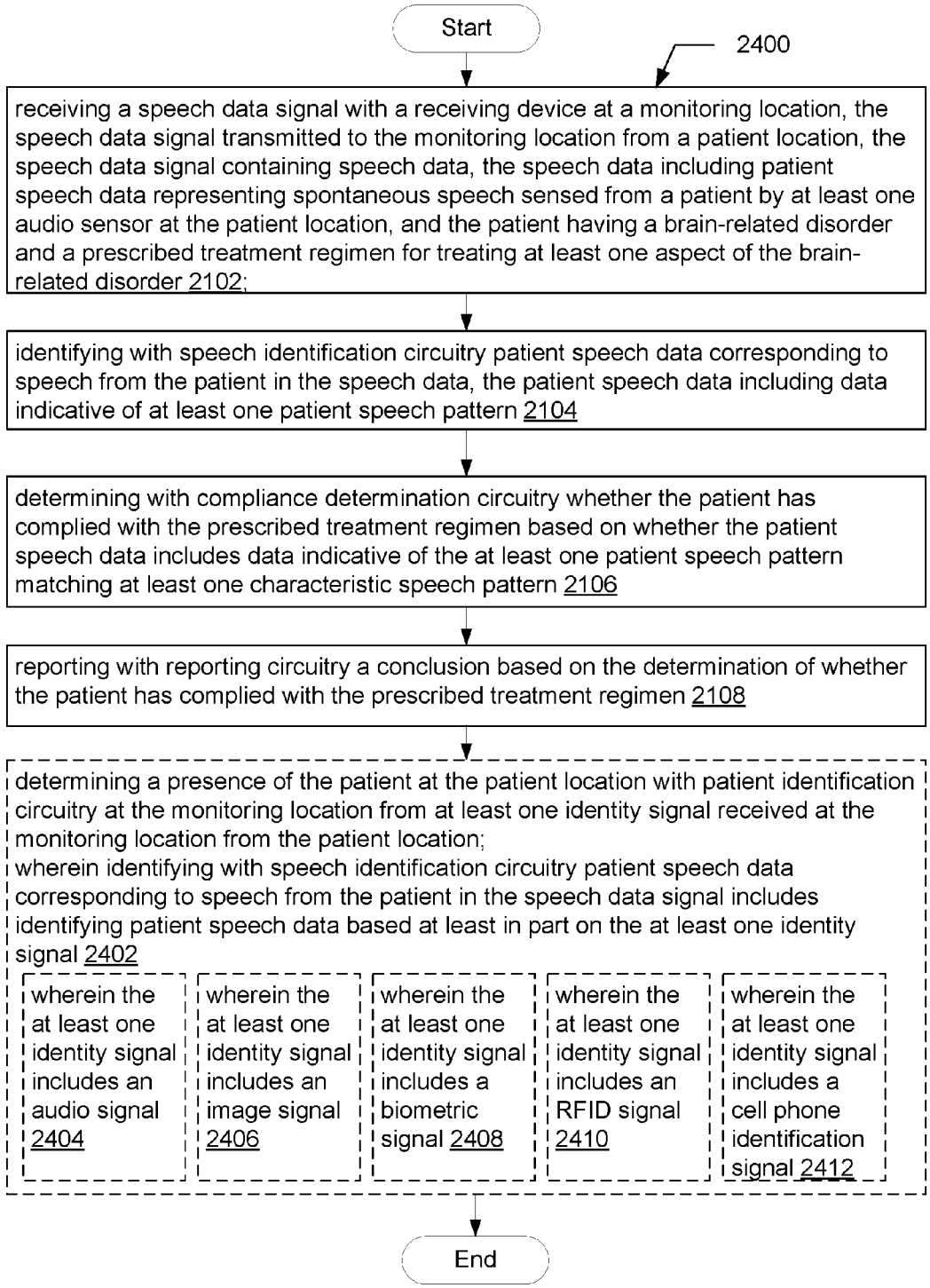
FIG. 24 is a flow diagram of further aspects of the method of FIG. 22.

FIG. 24 depicts a method 2400, which includes determining a presence of the patient at the patient location with patient identification circuitry at the monitoring location from at least one identity signal received at the monitoring location from the patient location, wherein identifying with speech identification circuitry patient speech data corresponding to speech from the patient in the speech data signal includes identifying patient speech data based at least in part on the identity signal, as indicated at 2402. In various aspects, the identity signal includes a voice signal, as indicated at 2404; an image signal, as indicated at 2406; a biometric signal, as indicated at 2408; an RFID signal, as indicated at 2410; or a cell phone identification signal, as indicated at 2412.

Figure 25:
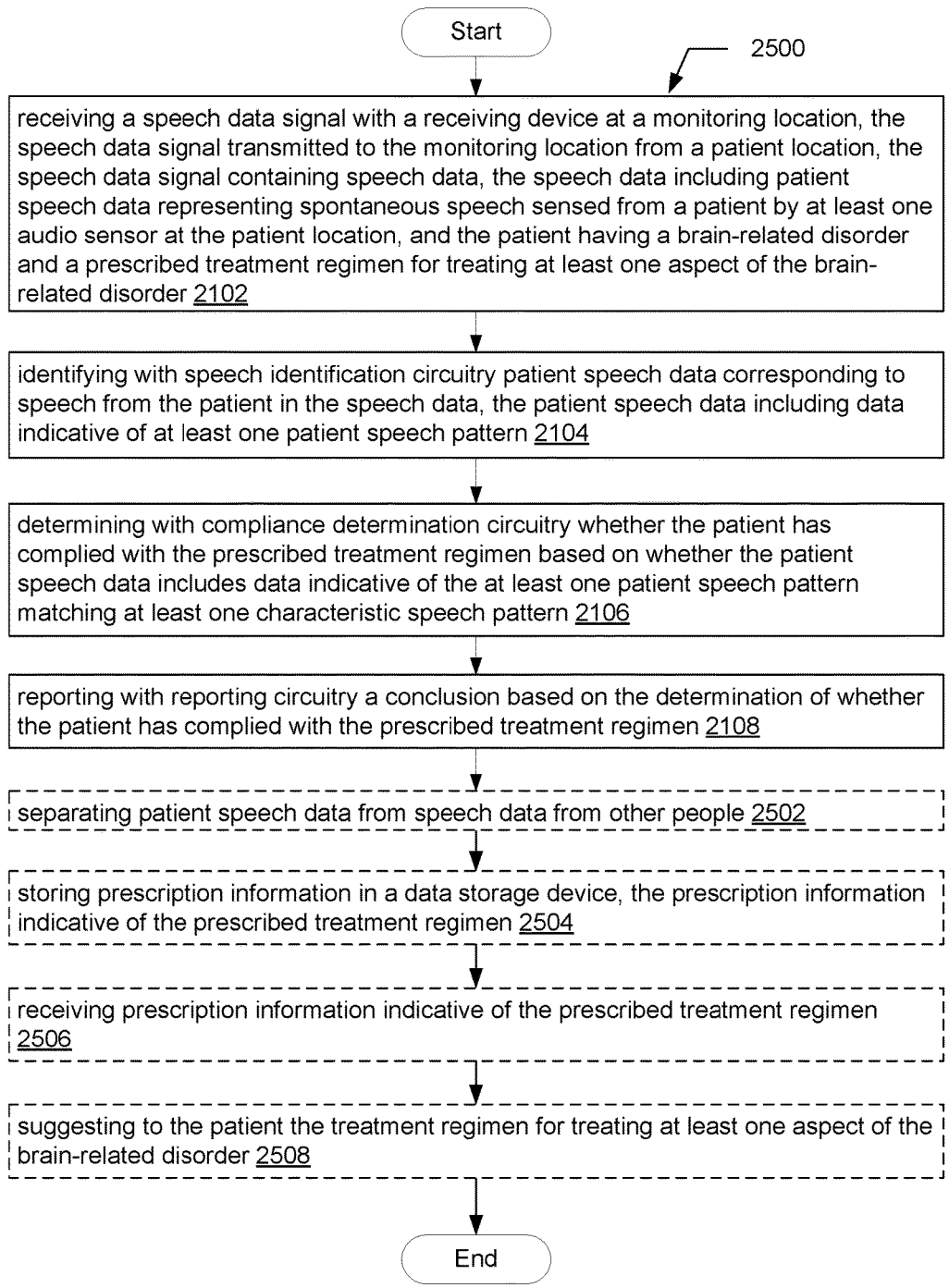
FIG. 25 is a flow diagram of further aspects of the method of FIG. 22.

FIG. 25 depicts method 2500, which includes one or more of separating patient speech data from speech data from other people, as indicated at 2502; storing prescription information in a data storage device, the prescription information indicative of the prescribed treatment regimen, as indicated at 2504; receiving prescription information indicative of the prescribed treatment regimen, as indicated at 2506; and suggesting to the patient the treatment regimen for treating at least one aspect of the brain-related disorder, as indicated at 2508.

Figure 26:
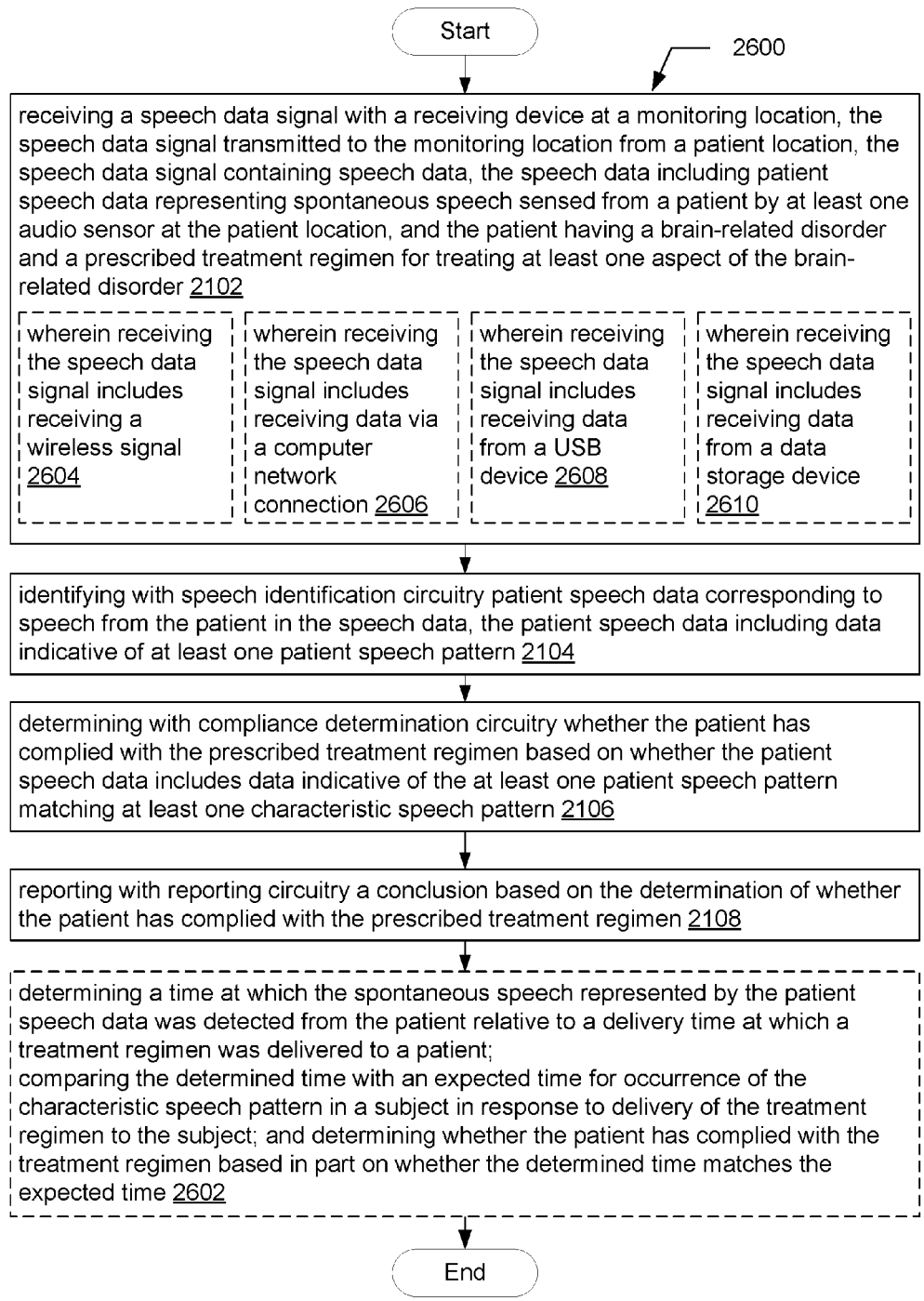
FIG. 26 is a flow diagram of further aspects of the method of FIG. 22.

FIG. 26 depicts a method 2600, relating to determining patient compliance based on whether the time course of the patient's response to a treatment regimen matches an expected time course. In an aspect, method 2600 includes determining a time at which the spontaneous speech represented by the patient speech data was detected from the patient relative to a delivery time at which a treatment regimen was delivered to a patient, comparing the determined time with an expected time for occurrence of the characteristic speech pattern in a subject in response to delivery of the treatment regimen to the subject, and determining whether the patient has complied with the prescribed treatment regimen based in part on whether the determined time matches the expected time, as indicated at 2602. In various aspects, receiving the speech data signal includes receiving a wireless signal, as indicated at 2604; receiving data via a computer network connection, as indicated at 2606; receiving data from a USB device, as indicated at 2608; and/or receiving data from a data storage device, as indicated at 2610.

Figure 27:
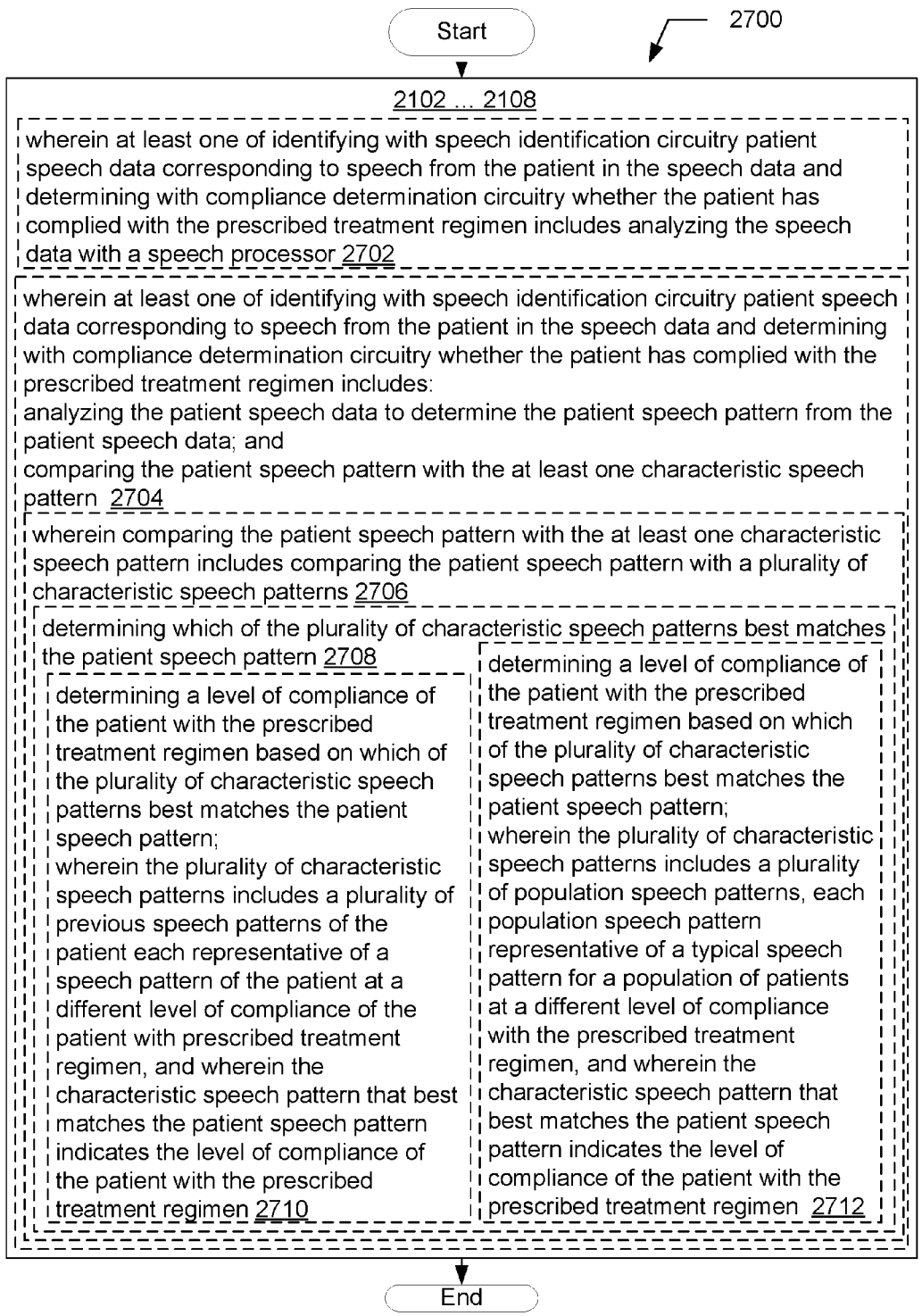
FIG. 27 is a flow diagram of further aspects of the method of FIG. 22.

FIG. 27 depicts method 2700 including steps 2102-2108 as shown in FIG. 21, and including additional steps relating to comparison of a patient's speech patterns with multiple characteristic speech patterns. In one aspect, at least one of identifying with speech identification circuitry patient speech data corresponding to speech from the patient in the speech data and determining with compliance determination circuitry whether the patient has complied with the prescribed treatment regimen includes analyzing the speech data with a speech processor, as indicated at 2702. In another aspect, at least one of identifying with speech identification circuitry patient speech data corresponding to speech from the patient in the speech data and determining with compliance determination circuitry whether the patient has complied with the prescribed treatment regimen includes analyzing the patient speech data to determine the patient speech pattern from the patient speech data, and comparing the patient speech pattern with the at least one characteristic speech pattern, as indicated at 2704.

In an aspect, comparing the patient speech pattern with the at least one characteristic speech pattern includes comparing the patient speech pattern with a plurality of characteristic speech patterns, as indicated at 2706. In addition, method 2700 may include determining which of the plurality of characteristic speech patterns best matches the patient speech pattern, as indicated at 2708. In connection therewith, an aspect, method 2700 also includes determining a level of compliance of the patient with the prescribed treatment regimen based on which of the plurality of characteristic speech patterns best matches the patient speech pattern, wherein the plurality of characteristic speech patterns includes a plurality of previous speech patterns of the patient each representative of a speech pattern of the patient at a different level of compliance of the patient with prescribed treatment regimen, and wherein the characteristic speech pattern that best matches the patient speech pattern indicates the level of compliance of the patient with the prescribed treatment regimen, as indicated at 2710. Method 2700 may also include determining a level of compliance of the patient with the prescribed treatment regimen based on which of the plurality of characteristic speech patterns best matches the patient speech pattern, wherein the plurality of characteristic speech patterns includes a plurality of population speech patterns, each population speech pattern representative of a typical speech pattern for a population of patients at a different level of compliance with the prescribed treatment regimen, and wherein the characteristic speech pattern that best matches the patient speech pattern indicates the level of compliance of the patient with the prescribed treatment regimen, as indicated at 2712.

Figure 28:
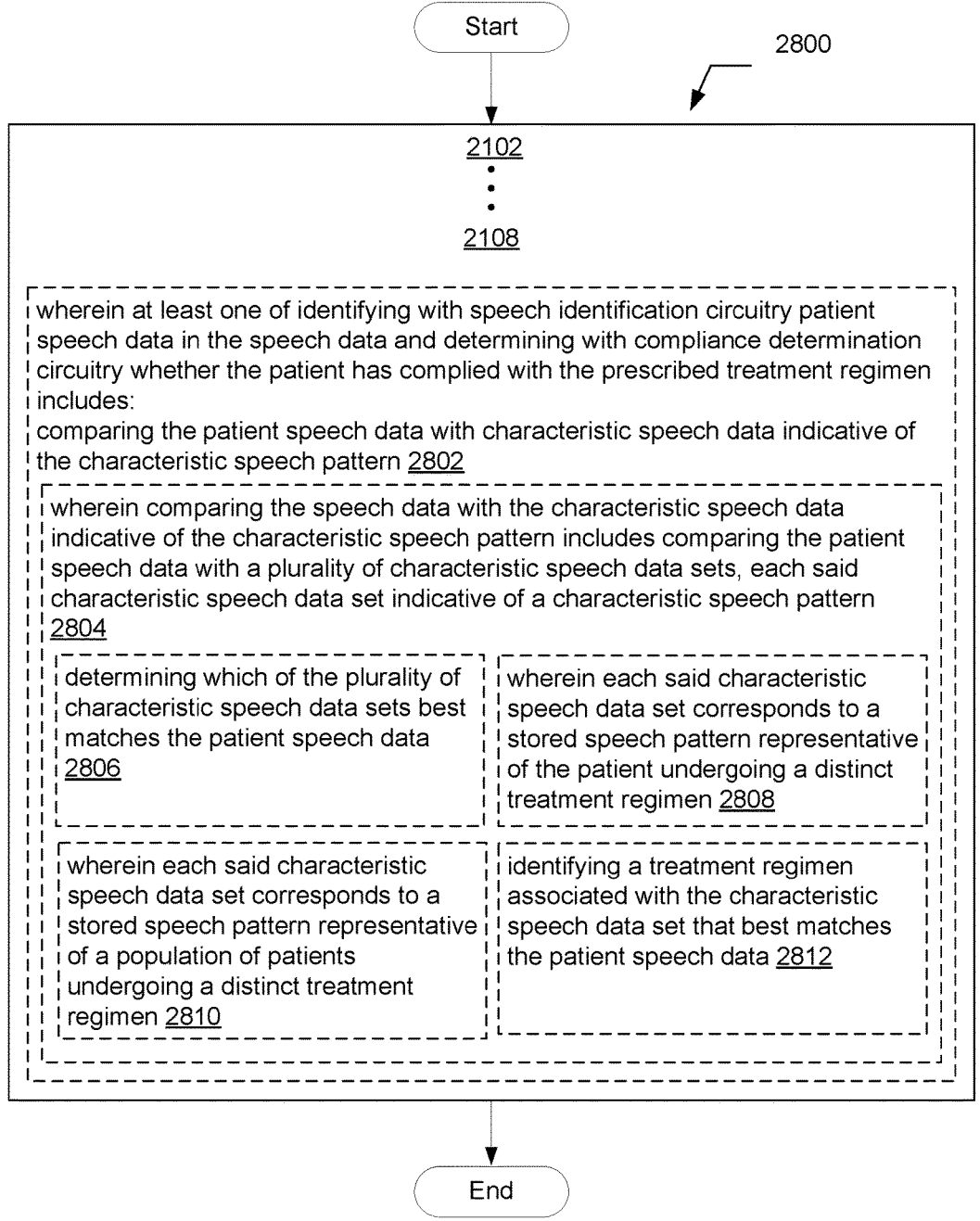
FIG. 28 is a flow diagram of further aspects of the method of FIG. 22.

FIG. 28 depicts method 2800 including steps 2102-2108 as shown in FIG. 21. In an aspect of method 2800, at least one of identifying with speech identification circuitry patient speech data in the speech data and determining with compliance determination circuitry whether the patient has complied with the prescribed treatment regimen includes comparing the patient speech data with characteristic speech data indicative of the characteristic speech pattern, as indicated at 2802. In an aspect, comparing the speech data with the characteristic speech data indicative of the characteristic speech pattern includes comparing the patient speech data with a plurality of characteristic speech data sets, each said characteristic speech data set indicative of a characteristic speech pattern, indicated at 2804. In connection therewith, in an aspect, method 2800 also includes determining which of the plurality of characteristic speech data sets best matches the patient speech data, as indicated at 2806. In an aspect, each said characteristic speech data set corresponds to a stored speech pattern representative of the patient undergoing a distinct treatment regimen, as indicated at 2808, or to a stored speech pattern representative of a population of patients undergoing a distinct treatment regimen, as indicated at 2810. In an aspect, method 2800 includes identifying a treatment regimen associated with the characteristic speech data set that best matches the patient speech data, as indicated at 2812.

Figure 29:
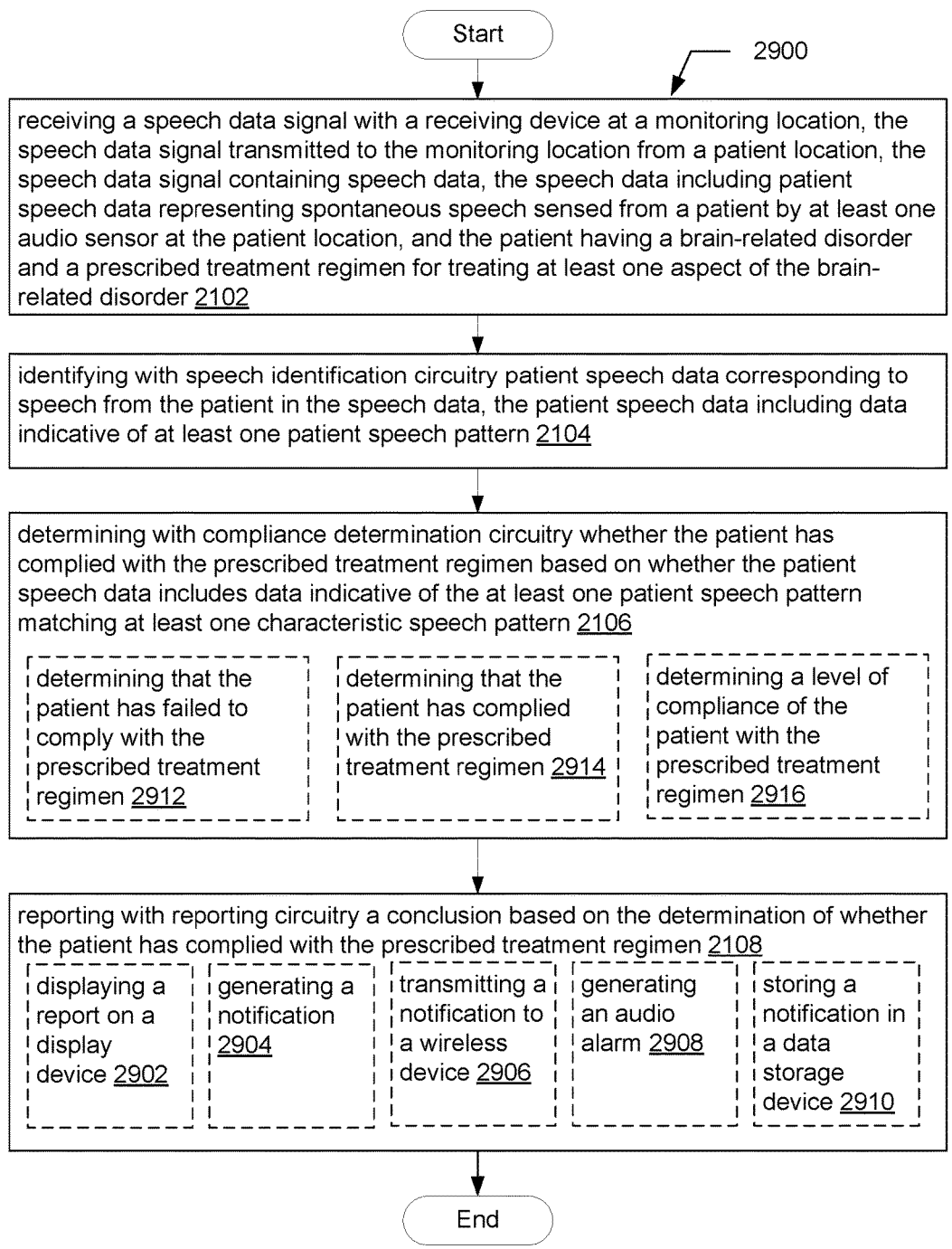
FIG. 29 is a flow diagram of further aspects of the method of FIG. 22.

FIG. 29 depicts method 2900, in which, in various aspects, reporting with reporting circuitry a conclusion based on the determination of whether the patient has complied with the prescribed treatment regimen includes displaying a report on a display device, as indicated at 2902; generating a notification, as indicated at 2904; transmitting a notification to a wireless device, as indicated at 2906; generating an audio alarm, as indicated at 2908; or storing a notification in a data storage device, as indicated at 2910. Generating an audio alarm may involve generating a beeping or chiming sound, for example, or generating a voice alarm (e.g., a warning or notification) from recorded or synthesized speech, e.g., to deliver a verbal warning to the medical care provider at the monitoring location.

In other aspects, determining with compliance determination circuitry whether the patient has complied with the prescribed treatment regimen includes determining that the patient has failed to comply with the prescribed treatment regimen, as indicated at 2912; determining that the patient has complied with the prescribed treatment regimen, as indicated at 2914; and/or determining a level of compliance of the patient with the prescribed treatment regimen, as indicated at 2916. Approaches for determining compliance, lack of compliance, or level of compliance are discussed herein above.

Figure 30:
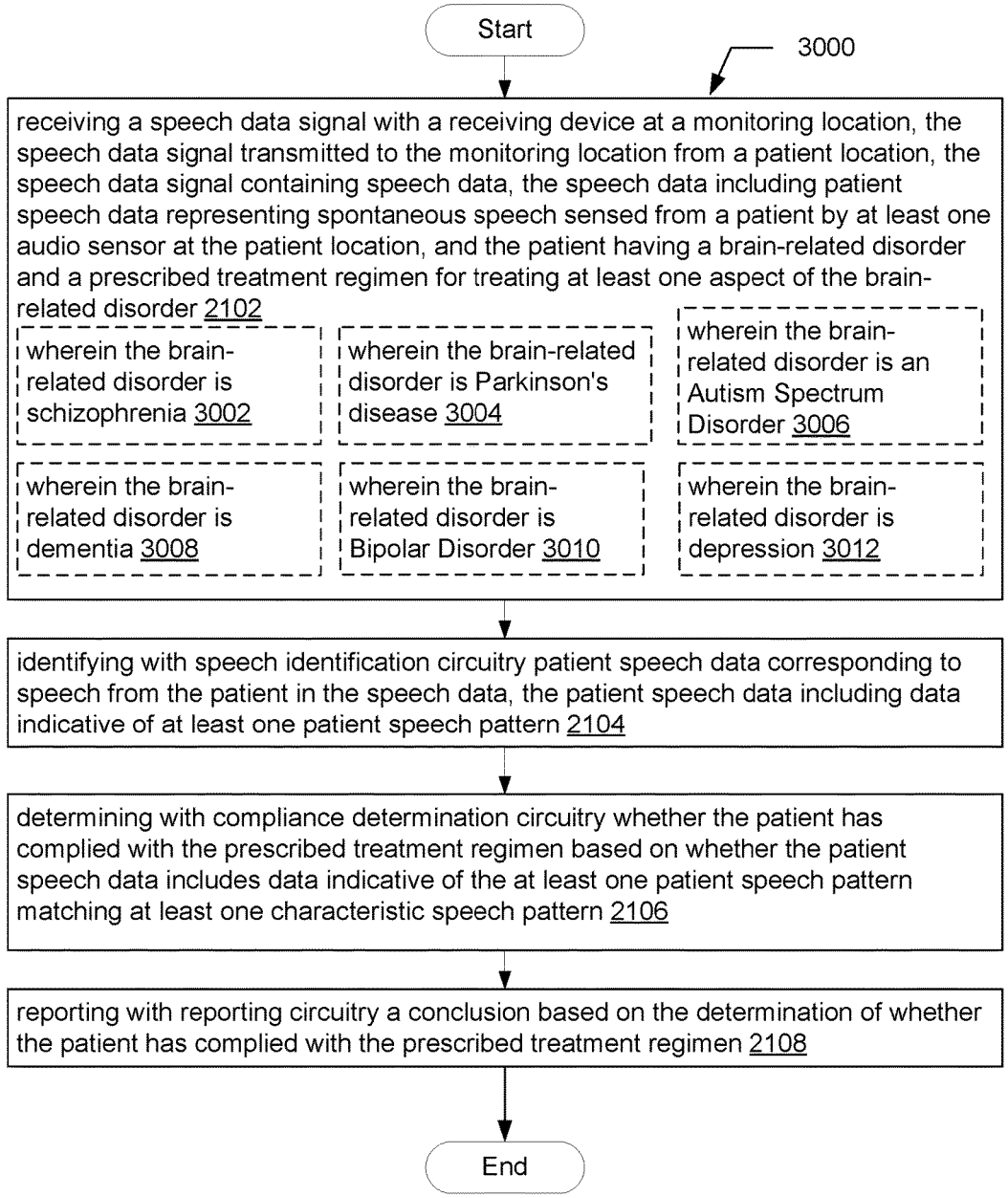
FIG. 30 is a flow diagram of further aspects of the method of FIG. 22.

FIG. 30 depicts method 3000, wherein the brain-related disorder is schizophrenia, as indicated at 3002; Parkinson's disease, as indicated at 3004; an Autism Spectrum Disorder, as indicated at 3006; dementia, as indicated at 3008; Bipolar Disorder, as indicated at 3010; or depression, as indicated at 3012. Other brain-related disorders, as discussed herein, may be monitored.

Figure 31:
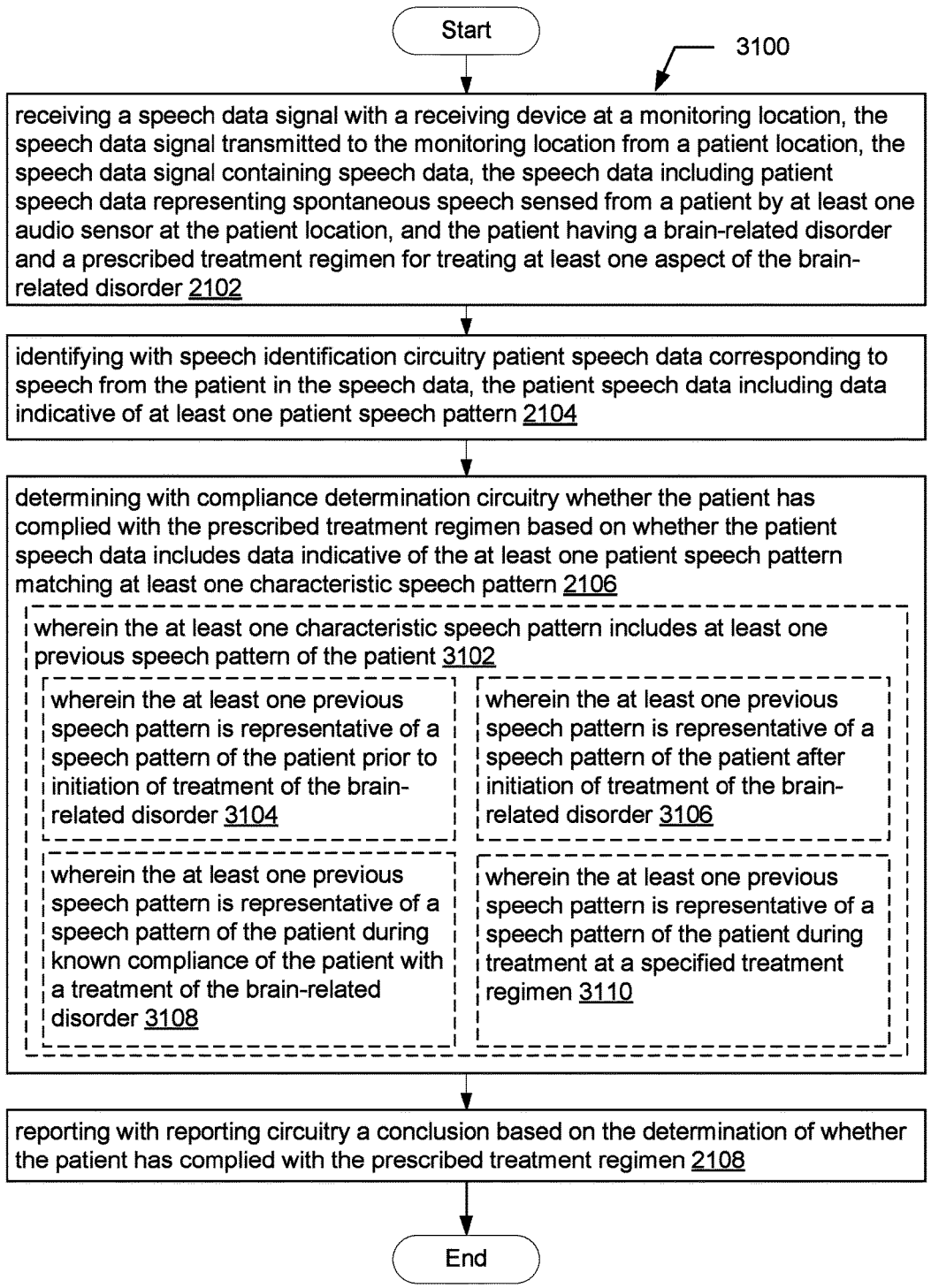
FIG. 31 is a flow diagram of further aspects of the method of FIG. 22.

As shown in FIG. 31, in an aspect of method 3100, the at least one characteristic speech pattern includes at least one previous speech pattern of the patient, as indicated at 3102. For example, in various aspects, the at least one previous speech pattern is representative of a speech pattern of the patient prior to initiation of treatment of the brain-related disorder, as indicated at 3104; a speech pattern of the patient after initiation of treatment of the brain-related disorder, as indicated at 3106; a speech pattern of the patient during known compliance of the patient with a treatment of the brain-related disorder, as indicated at 3108; or a speech pattern of the patient during treatment at a specified treatment regimen, as indicated at 3110. Comparison of a patient speech pattern to one or more characteristic speech patterns is discussed herein above.

Figure 32:
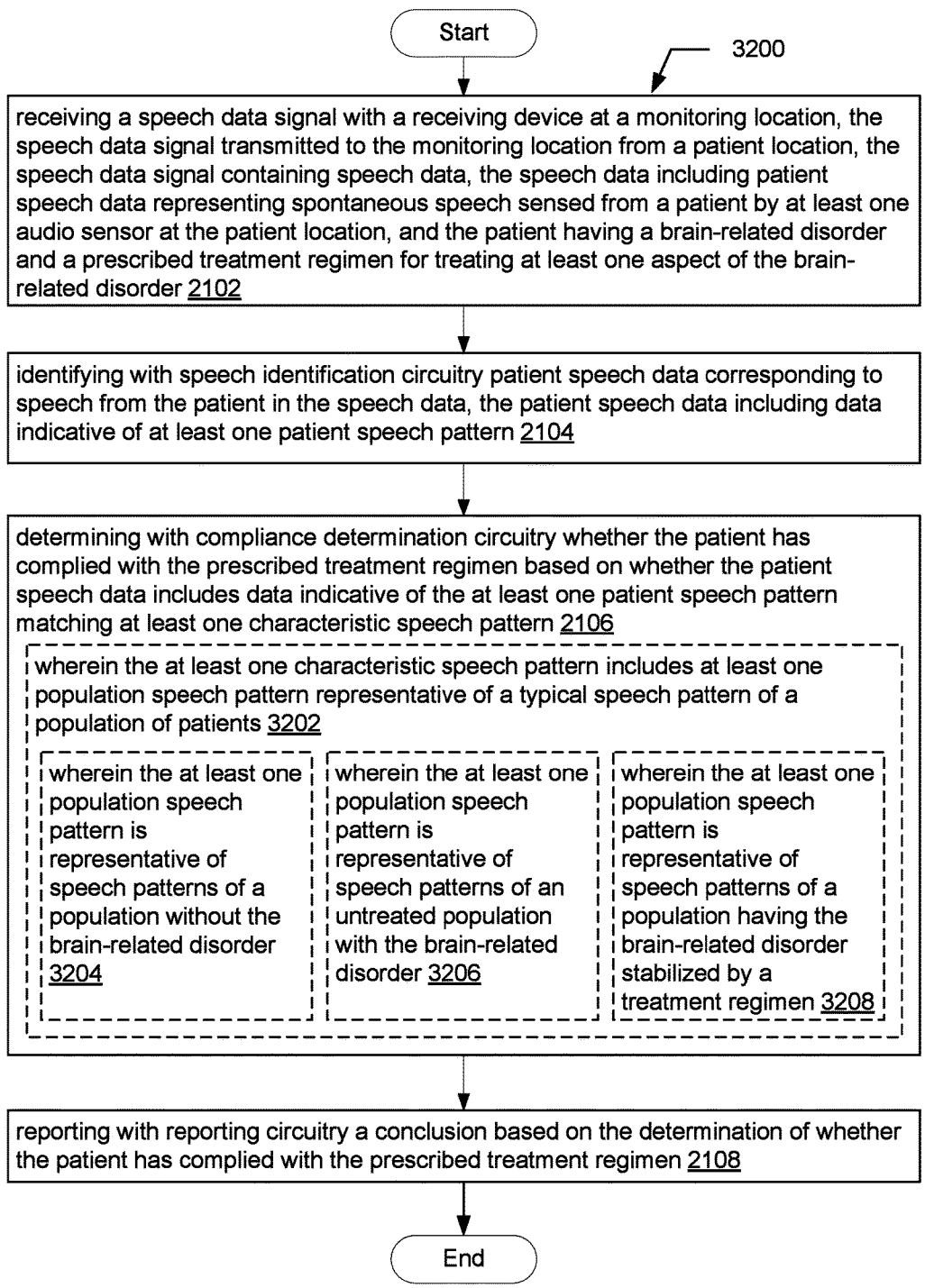
FIG. 32 is a flow diagram of further aspects of the method of FIG. 22.

As shown in FIG. 32, in an aspect of a method 3200, the at least one characteristic speech pattern includes at least one population speech pattern representative of a typical speech pattern of a population of patients, as indicated at 3202. For example, the at least one population speech pattern is representative of speech patterns of a population without the brain-related disorder, as indicated at 3204; speech patterns of an untreated population with the brain-related disorder, as indicated at 3206; or speech patterns of a population having the brain-related disorder stabilized by a treatment regimen, as indicated at 3208.

Figure 33:
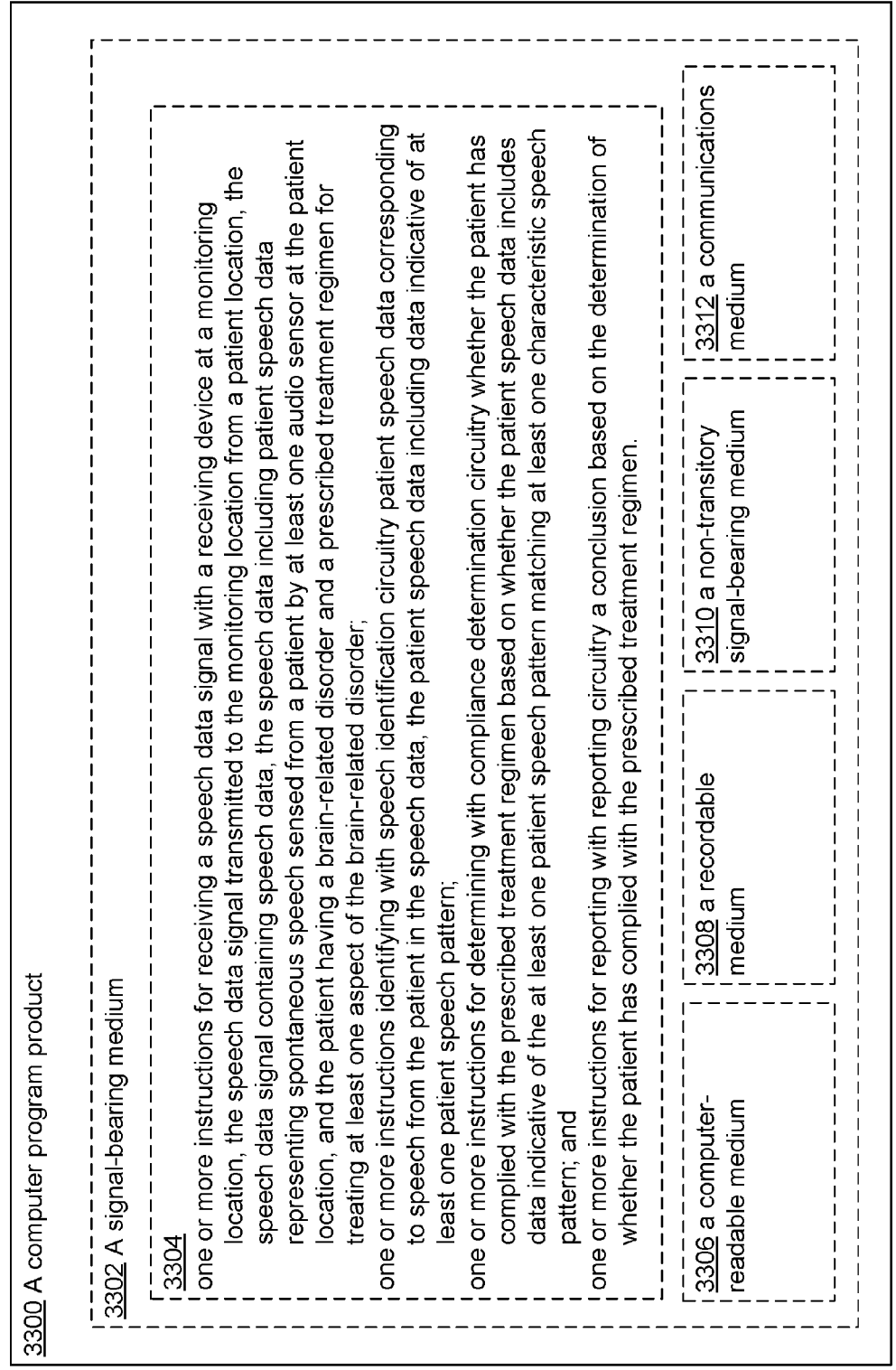
FIG. 33 is a block diagram of a computer program product including a signal-bearing medium.

FIG. 33 depicts a computer program product 3300, for implementing the method of FIG. 22. Computer program product 3300 includes a signal-bearing medium 3302 bearing one or more instructions for receiving a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at a patient location, and the patient having a brain-related disorder and a prescribed treatment regimen for treating at least one aspect of the brain-related disorder, one or more instructions identifying with speech identification circuitry patient speech data corresponding to speech from the patient in the speech data, the patient speech data including data indicative of at least one patient speech pattern, one or more instructions for determining with compliance determination circuitry whether the patient has complied with the prescribed treatment regimen based on whether the patient speech data includes data indicative of the at least one patient speech pattern matching at least one characteristic speech pattern, and one or more instructions for reporting with reporting circuitry a conclusion based on the determination of whether the patient has complied with the prescribed treatment regimen, as indicated at 3304. Signal-bearing medium 3302 may be, for example, a computer-readable medium 3306, a recordable medium 3308, a non-transitory signal-bearing medium 3310, or a communications medium 3312.

Figure 34:
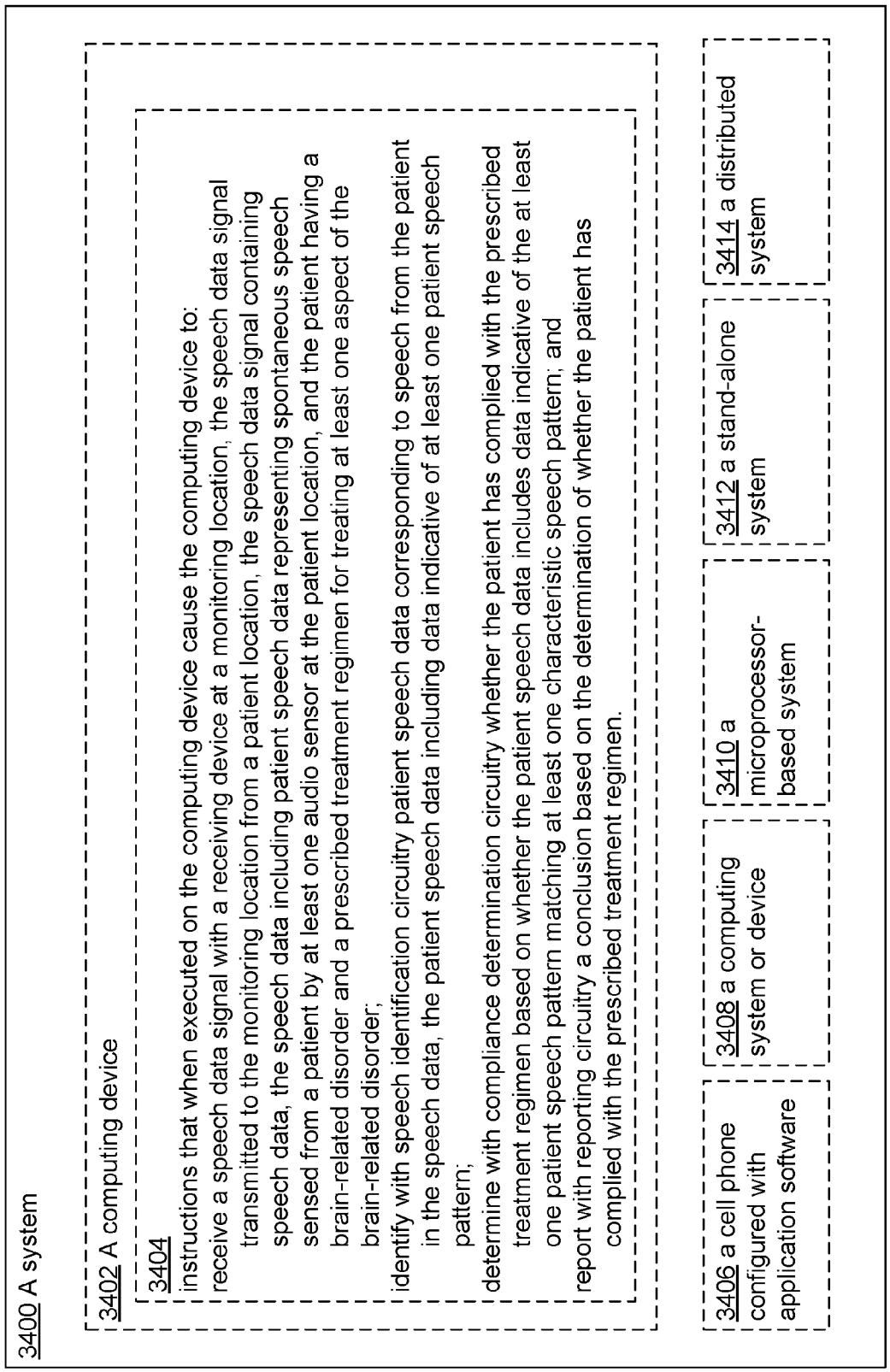
FIG. 34 is a block diagram of a system including a computing device.

FIG. 34 depicts a system 3400 for implementing the method of FIG. 22. System 3400 includes a computing device 3402 and instructions that when executed on computing device 3402 cause computing device 3402 to receive a speech data signal with a receiving device at a monitoring location, the speech data signal transmitted to the monitoring location from a patient location, the speech data signal containing speech data, the speech data including patient speech data representing spontaneous speech sensed from a patient by at least one audio sensor at a patient location, and the patient having a brain-related disorder and a prescribed treatment regimen for treating at least one aspect of the brain-related disorder; identify with speech identification circuitry patient speech data corresponding to speech from the patient in the speech data, the patient speech data including data indicative of at least one patient speech pattern; determine with compliance determination circuitry whether the patient has complied with the prescribed treatment regimen based on whether the patient speech data includes data indicative of the at least one patient speech pattern matching at least one characteristic speech pattern; and report with reporting circuitry a conclusion based on the determination of whether the patient has complied with the prescribed treatment regimen, as indicated at 3404. System 3400 may be, for example, a cell phone configured with application software, as indicated at 3406; a computing system or device 3408; a microprocessor-based system 3410; a stand-alone system 3412; or a distributed system 3414.

Figure 35:
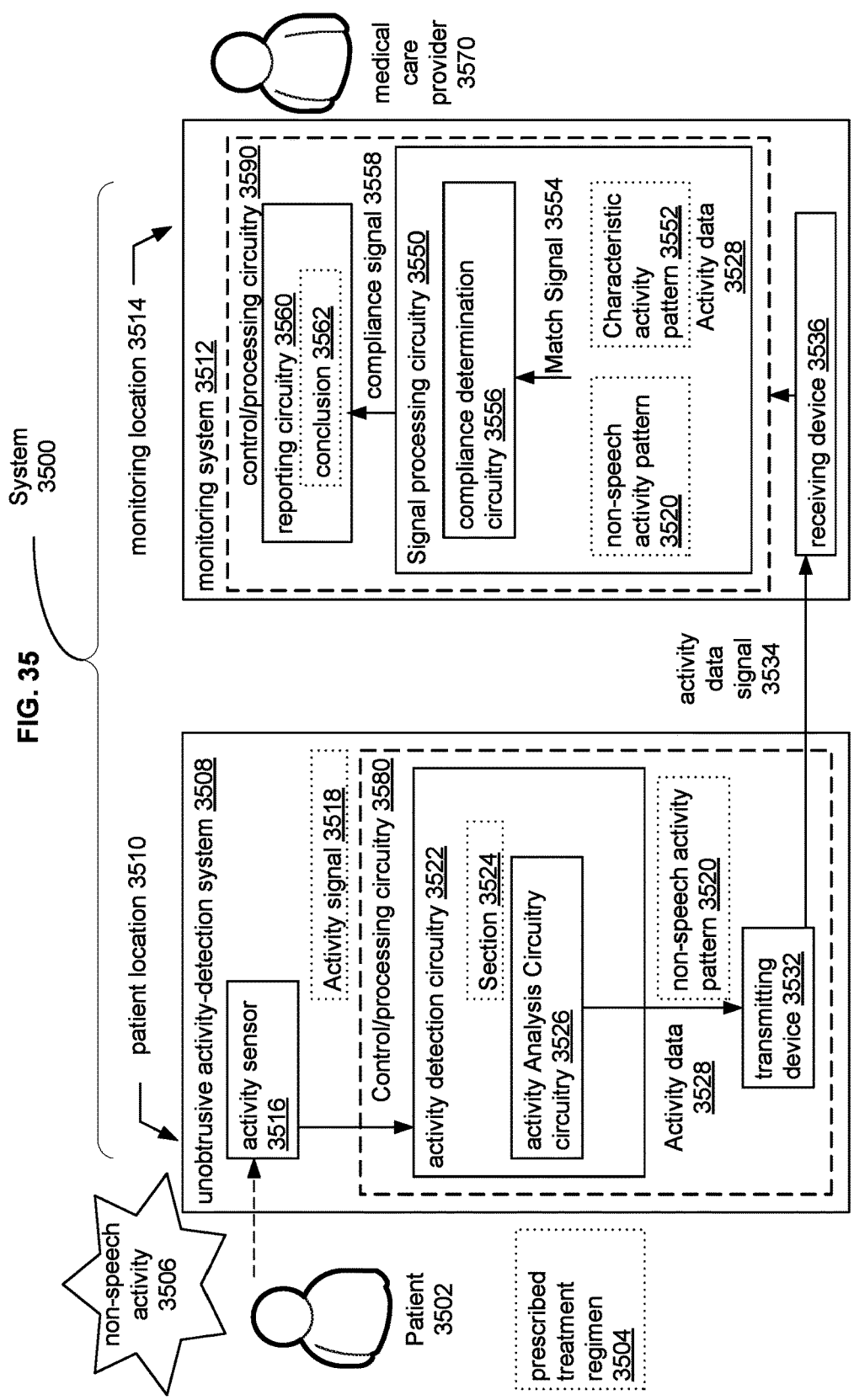
FIG. 35 is a block diagram of a system for monitoring compliance of a patient with a treatment regimen.

In an aspect, a patient 3502 has a brain-related disorder, and treatment of the patient according to a prescribed treatment regimen 3504 results in detectable changes in the patient's performance of one or more non-speech activities, relative to the patient's activity performance while in an untreated or partially treated state. In an aspect, failure of the patient to comply with a prescribed treatment regimen can be detected by monitoring the patient's activity-related activity patterns, and steps can be taken to address the patient's lack of compliance. FIG. 35 illustrates in block diagram form a system 3500 for monitoring compliance of a patient 3502 with a prescribed treatment regimen 3504 based upon unobtrusive detection of a non-verbal activity of the patient, where the non-verbal activity corresponds to performance of non-speech activity 3506 by the patient. System 3500 includes unobtrusive activity-detection system 3508 at patient location 3510, which is used to detect non-verbal activity of the patient, and monitoring system 3512 at monitoring location 3514, which allows remote monitoring of patient compliance with prescribed treatment regimen 3504 by a medical care provider 3570 or other interested party or entity, e.g., a family member, an insurance company, etc.

In FIG. 35, and in other figures herein, in general, unless context dictates otherwise, solid lines are used to indicate standard components or steps, and dashed lines are used to represent optional components or steps. Unless context indicates otherwise, dotted lines are used to indicate data or information. Dashed lines may also be used to indicate signals.

System 3500 monitors compliance of patient 3502 with prescribed treatment regimen 3504 by detecting and analyzing activity of patient 3502 corresponding to performance of a non-speech activity 3506.

Unobtrusive activity-detection system 3508 includes at least one activity sensor 3516 for sensing at least one activity signal 3518 including a non-speech activity pattern 3520 corresponding to performance of non-speech activity 3506 by patient 3502 at patient location 3510. Unobtrusive activity-detection system 3508 also includes activity detection circuitry 3522, which is configured to identify at least one section 3524 of the at least one activity signal 3518 containing the non-speech activity pattern 3520, and activity analysis circuitry 3526 for processing the at least one section 3524 of the at least one activity signal 3518 to generate activity data 3528 including data indicative of whether the patient has complied with the treatment regimen. In addition, unobtrusive activity-detection system 3508 includes at least one transmitting device 3532 for transmitting activity data signal 3534 including activity data 3528 including data indicative of whether the patient has complied with the treatment regimen. Transmitting device 3532 transmits activity data signal 3534 from patient location 3510 to receiving device 3536 at monitoring location 3514.

Monitoring system 3512 at monitoring location 3514 includes at least one receiving device 3536 for use at a monitoring location 3514 for receiving an activity data signal 3534 transmitted to the monitoring location 3514 from patient location 3510. Activity data signal 3534 contains activity data 3528 representing at least one non-speech activity pattern 3520 in activity sensed from patient 3502 with at least one activity sensor 3516 in unobtrusive activity-detection system 3508 at patient location 3510 during performance of non-speech activity 3506 by patient 3502. Monitoring system 3512 also includes signal processing circuitry 3550, which is configured to analyze activity data signal 3534 to determine whether activity data 3528 represents at least one non-speech activity pattern 3520 that matches at least one characteristic activity pattern 3552. Signal processing circuitry 3550 generates match signal 3554 indicating a determination that non-speech activity pattern 3520 matches a characteristic activity pattern 3552. Monitoring system 3512 also includes compliance determination circuitry 3556, which is configured to determine whether patient 3502 has complied with prescribed treatment regimen 3504 based upon whether activity data 3528 represents a non-speech activity pattern 3520 that matches at least one characteristic activity pattern 3552. Compliance determination circuitry 3556 generates compliance signal 3558. Monitoring system 3512 also includes reporting circuitry 3560, which is configured to report a conclusion 3562 (regarding patient's compliance or lack thereof) based on the determination of whether the patient has complied with the prescribed treatment regimen 3504, as indicated by compliance signal 3558.

Both unobtrusive activity-detection system 3508 and monitoring system 3512 include control/processing circuitry, e.g., control/processing circuitry 3580 in unobtrusive activity-detection system 3508 and control/processing circuitry 3590 in monitoring system 3512, which includes the circuitry components specifically described herein and other circuitry components used to control operation of unobtrusive activity-detection system 3508 and monitoring system 3512, respectively.

In different embodiments, examples of which are described elsewhere here, different levels of signal processing take place in unobtrusive activity-detection system 3508 at patient location 3510 versus at monitoring system 3512 at monitoring location 3514. The location at which different signal processing aspects are performed may depend on availability of data storage space; speed, reliability and/or power consumption of data transmission between patient location 3510 and monitoring location 3514; and privacy concerns relating to storage and transmittal of patient data, among other considerations. As will be discussed in greater detail herein below, activity data signal 3534 may contain raw activity data, information obtained from processed activity data, or both.

In an aspect, patient 3502 has a brain-related disorder, and prescribed treatment regimen 3504 is a treatment regimen prescribed to patient 3502 for treating at least one aspect of the brain-related disorder. Brain-related disorders include, for example, mental disorders, psychological disorders, psychiatric disorders, traumatic disorders, lesion-related disorders, and/or neurological disorders, as discussed in greater detail elsewhere herein. Prescribed treatment regimen 3504 may include a prescription for one or more therapeutic treatments, including medications, pharmaceuticals, nutraceuticals, therapeutic activities, diet, sleep, exercise, counseling, etc., to be used individually or in combination. In various aspects, prescribed treatment regimen 3504 specifies type, quantity, and time course of any or all such therapeutic treatments.

Monitoring system 3512 at monitoring location 3514 allows medical care provider 3570 or another interested individual or entity to remotely monitor compliance of patient 3502 with prescribed treatment regimen 3504. Monitoring location 3514 may be, for example, a hospital, clinic, data center, or doctor's office. Monitoring location 3514 may be a short distance away from patient location 3510 (e.g., in another room of the same building, or even within the same room as patient location 3510) or it may be in a separate building, a few miles away, or many miles away.

Systems as described herein can be used, for example, to monitor patient compliance with prescribed treatment regimen 3504 at the request of or with the cooperation and/or authorization of patient 3502, e.g., in the situation that the patient and/or the patient's caregiver wish to track the patient's compliance with the prescribed treatment regimen. In some cases, monitoring of patient compliance with a prescribed treatment regimen can be implemented at the request or requirement of a caregiver, insurance company, or other individual or entity, for example, as a condition of living in a group home, mental health care facility, or other institution, or as a condition of insurance reimbursement for treatment. In some cases, monitoring of compliance can be implemented without knowledge and/or authorization of the patient, e.g., in situations in which the patient is not capable of making decisions for his or her self or to fulfill a legal requirement.

Figure 36:
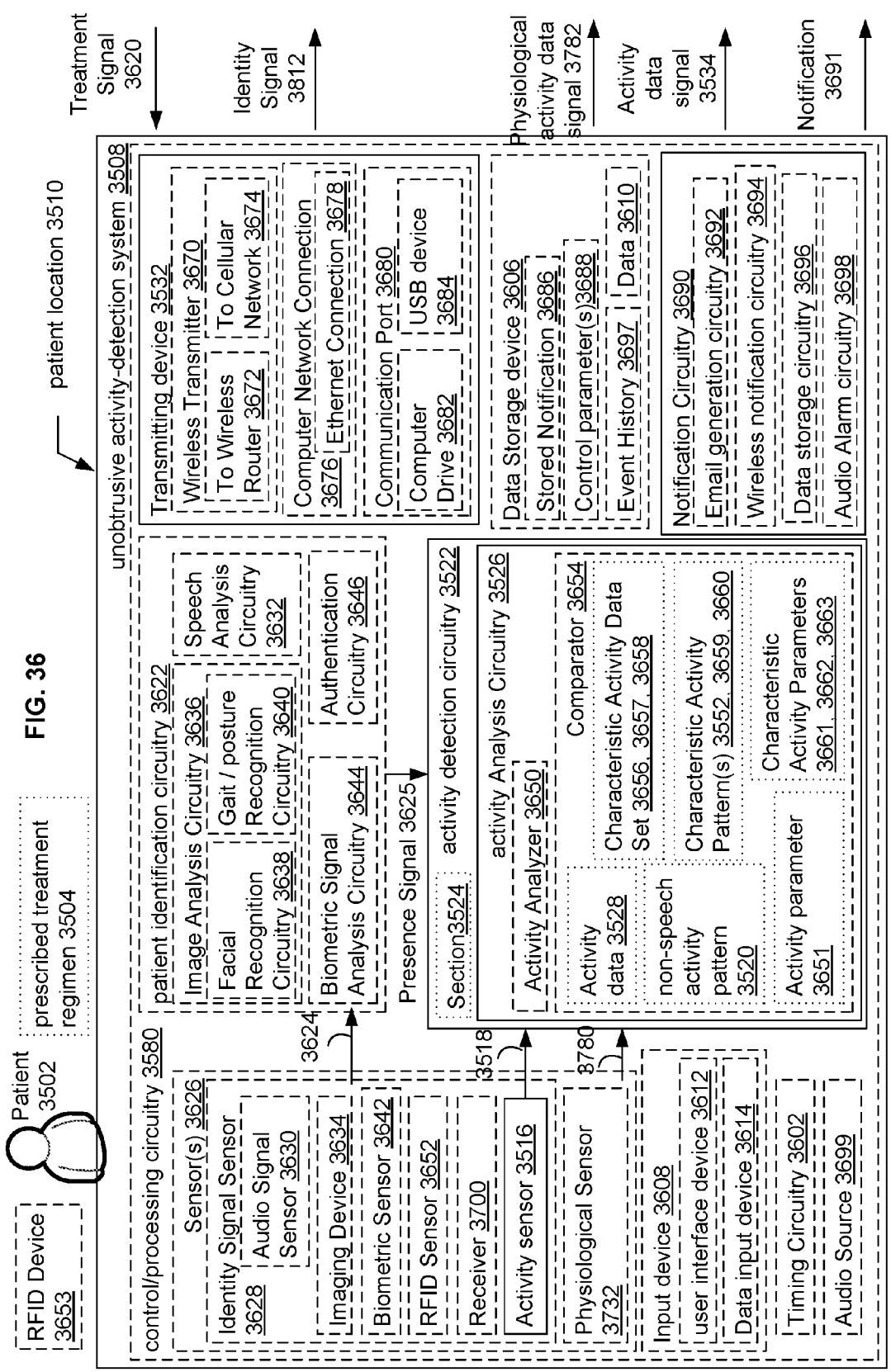
FIG. 36 is a block diagram of an unobtrusive activity-detection system.

FIG. 36 illustrates components of unobtrusive activity-detection system 3508 at patient location 3510. As discussed above, unobtrusive activity-detection system 3508 includes at least one activity sensor 3516, activity detection circuitry 3522, activity analysis circuitry 3526, and at least one transmitting device 3532. Activity detection circuitry 3522, activity analysis circuitry 3526, and other circuitry components as described herein include or form a part of control/processing circuitry 3580.

Non-speech activity detected by unobtrusive activity-detection system 3508 corresponds to one or more non-speech activity 3506 performed by patient 3502 (as shown in FIG. 35). For example, such activities may include various activities of daily life, or other activities or tasks performed routinely by patient 3502, including, but not limited to, hygiene, washing, eating, dressing, brushing teeth, brushing hair, combing hair, preparing food, interacting with another person (e.g., in the same location or via an electronic device), interacting with an animal, interacting with a machine, interacting with an electronic device, or using an implement. In an aspect, such activities are performed by the patient 3502 without prompting by unobtrusive activity-detection system 3508. In an aspect, detection of non-speech activity-related activity is accomplished in a manner that is not noticeable to the patient, and does not interfere with the patient's daily routine. Unprompted activity refers to activity that is performed independent of any prompt by unobtrusive activity-detection system 3508. Such activity can be considered "passively captured" in that capture of such activity is not predicated on the delivery of a prompt to the patient from unobtrusive activity-detection system 3508. It should be noted, however, that, as used herein, unprompted activity in some cases includes activity produced by the patient in response to prompts or queries by another person, e.g., in the course of interaction with the person. In addition, activity produced by the patient that is not dependent on prior interaction with another person is also considered "spontaneous activity."

Unobtrusive activity-detection system 3508 may include various types of sensors 3626, including various types of activity sensor(s) 3516 for detecting activities that provide information regarding the patient's brain-related state. The patient's movements may be detected directly or indirectly with various types of sensors (including, but not limited to, pressure, force, capacitance, optical, motion, and acceleration sensors). Imaging sensors (e.g., cameras) can provide images of the patient that can be used to determine various aspects of motion of the patient. The patient's interaction with devices may be detected with user interface and input devices (e.g., keyboard, pointing device, or touchscreen) and/or device controls (including, but not limited to, controllers for game or entertainment devices or systems, appliances, vehicles, medical equipment, etc.). Interaction of the patient with other individuals, pets, or other animals, can be detected through image analysis, or through the use of proximity sensors to detect proximity of the patient to the individual or animal (with proximity assumed to correlate with interaction). Activity sensor 3516 may be worn or carried by the patient, built into or attached to a device with which the patient interacts, or located in the patient's environment (e.g., a video camera in the patient's home).

In an aspect, activity detection circuitry 3522 is configured to identity the at least one section 3524 of the at least one activity signal containing non-speech activity pattern 3520 from an activity signal 3518 corresponding to unprompted performance of the non-speech activity by the patient.

In an aspect, unobtrusive activity-detection system 3508 includes timing circuitry 3602 configured to control timing of operation of at least a portion of unobtrusive activity-detection system 3508 to perform substantially continuously sensing the at least one activity signal 3518 with the at least one activity sensor 3516. In an aspect, timing circuitry 3602 includes a clock or timer device. For example, timing circuitry 3602 may be configured to cause sensing to be performed substantially continuously by causing samples to be collected from the activity sensor 3516 (e.g., via an A/D converter, not shown) at a fixed sampling rate that is sufficiently high to capture any meaningful variations in the activity sensed by the sensor (e.g., at at least the Nyquist rate). The sampling rate may be determined by hardware or software, and may be factory pre-set or controllable by the user (e.g., the sampling rate may be determined by one or more control parameters 3688 stored in data storage device 3606, which may be set during manufacture of unobtrusive activity-detection system 3508, or entered by a user of the system via input device 3608.) For example, in an aspect, control/processing circuitry 3580 includes an A/D converter, with the sampling rate of the A/D converter controlled by timing circuitry 3602.

In another aspect, timing circuitry 3602 is configured to control timing of operation of at least a portion of the system to perform intermittently at least one of sensing the at least one activity signal 3518 with the at least one activity sensor 3516, identifying the at least one section 3524 of the at least one activity signal containing the non-speech activity pattern with the activity detection circuitry 3522, processing the at least one section of the at least one activity signal to generate activity data 3528 including data indicative of whether the patient has complied with the treatment regimen with the activity analysis circuitry 3526, and transmitting an activity data signal 3534 including the activity data 3528 including data indicative of whether the patient has complied with the treatment regimen from the patient location 3510 to a receiving device at a monitoring location with the at least one transmitting device 3532. For example, in an aspect, intermittent sensing of the at least one activity signal 3518 is controlled by using software to determine sampling rate and times at which sampling is performed, with appropriately selected control parameters 3688 stored in data storage device 3606. Alternatively, in an aspect, activity is sensed substantially continuously with activity sensor 3516, but either activity detection circuitry 3522 and/or activity analysis circuitry 3526 is configured to process the activity signal 3518 and/or section 3524 intermittently rather than continuously. In another aspect, activity signal 3518 is sampled on a substantially continuous basis, but transmitting device 3532 is configured (with hardware or software) to transmit activity data signal 3534 to the monitoring location only intermittently (once an hour, once a day, etc.). Intermittent performance of sampling, data transmission, and/or other system functions include performance at uniform intervals, any sort of non-uniform intermittent pattern (e.g., at a high frequency during some parts of the day and lower frequency during other parts of the day), or at random or quasi-random intervals (e.g., as determined by a random number generator). In an aspect, timing of system functions is controlled in part by timing circuitry 3602 and in part in response to some other sensed parameter or other inputs; for example, a basic schedule may be determined by timing circuitry 3602 but if it is determined that the subject is asleep or is not present, or if the data cannot be transmitted due to low signal strength, low battery power, etc., the scheduled function may be delayed until suitable conditions are obtained. Data storage device 3606 is used to store data 3610 that includes any or all of activity signal 3518, section 3524 of activity signal, and activity data 3528, as such data are obtained. Data thus stored can be retrieved from data storage device 3606 for transmission with transmitting device 3532 intermittently. Data storage device 3606 may be any of various types of data storage and/or memory devices.

In an aspect, timing circuitry 3602 is configured to control timing of operation of at least a portion of the system to perform according to a schedule at least one of sensing the at least one activity signal with the at least one activity sensor 3516, identifying the at least one section 3524 of the at least one activity signal containing the non-speech activity pattern 3520 with the activity detection circuitry 3522, processing the at least one section 3524 of the at least one activity signal to generate activity data 3528 including data indicative of whether the patient has complied with the treatment regimen the activity analysis circuitry, and transmitting an activity data signal 3534 including the activity data including data indicative of whether the patient has complied with the treatment regimen from the patient location to a receiving device at a monitoring location with the at least one transmitting device 3532. Performance of the aforementioned steps according to a schedule can be controlled by timing circuitry 3602 configured by hardware and software, using control parameters 3688, including sampling rate and times at which sampling, processing of activity signal 3518 and/or section 3524, and transmission of activity data signal 3534 are to be performed. The timing of these steps can be determined by control parameters 3688, which may be set or selected by a user, or preset during manufacture of the device, as described above. Unobtrusive activity-detection system 3508 may include one or more power sources (not shown), e.g., a battery, a plug for connecting to an electrical outlet or communication port, e.g., a USB port, or any of various other types of power sources.

As noted above, in an aspect, unobtrusive activity-detection system 3508 includes an input device 3608. In various aspects, input device 3608 includes one or more of a user interface device 3612, which may be any of various types of user interface devices, or data input device 3614, which is a data input device adapted to receive data from a computing device or other electrical circuitry. Such data may be received by a wired connection or wireless connection. In an aspect, input device 3608 is used for receiving a treatment signal 3620 indicative of initiation of treatment of the patient according to the treatment regimen. In an aspect, treatment signal 3620 is received from a user (either the patient or a caregiver of the patient) via a user interface device 3612. In another aspect, treatment signal 3620 is received via data input device 3614.

In an aspect, unobtrusive activity-detection system 3508 includes patient identification circuitry 3622, which is configured to determine a presence of the patient from at least one identity signal 3624 sensed at the patient location, and to generate presence signal 3625 which is provided to activity detection circuitry 3522. In an aspect, an identity signal 3812 is transmitted from unobtrusive activity-detection system 3508 to a monitoring system at the monitoring location. Identity signal 3812 may be the same as identity signal 3624, or may be a processed version of identity signal 3624. In implementations in which unobtrusive activity-detection system 3508 does not include patient identification circuitry 3622, identity signal 3812 may be transmitted to the monitoring location and processed by circuitry there to determine identity/presence of the patient. In implementations in which unobtrusive activity-detection system 3508 include patient identification circuitry 3622, identity signal 3812 transmitted to the monitoring location so that the presence/identity of the patient may be determined from either the patient location or the monitoring location, or both, or the identity signal may be used for other purposes.

As noted previously, unobtrusive activity-detection system 3508 includes activity sensor 3516. In some aspects, activity signal 3518 sensed by activity sensor 3516 functions not only as a source of information regarding one or more activities performed by patient 3502, but also as an identity signal 3624 which is used to determine the identity of patient 3502. In an aspect, patient identification circuitry 3622 is configured to identify the at least one section 3524 of the at least one activity signal containing the non-speech activity pattern based at least in part on a determination of the presence of the patient 3502 by patient identification circuitry 3622. In an aspect the at least one identity signal 3624 includes at least a portion of the at least one activity signal 3518, and patient identification circuitry 3622 is configured to analyze the activity signal 3518 to identify at least a portion of the at least one activity signal that resembles a known activity pattern of the patient. Accordingly, in this example activity sensor 3516 is also identity signal sensor 3628.

In order to use activity signal 3518 as identity signal 3624, it may be necessary to process activity signal 3518 to determine the presence of the patient and simultaneously or subsequently process activity signal 3518 with activity detection circuitry 3522 to generate activity data 3528. This can be accomplished by parallel processing of activity signal 3518 by patient identification circuitry 3622 and activity detection circuitry 3522, or by processing activity signal 3518 first with patient identification circuitry 3622 and subsequently with activity detection circuitry 3522. If the latter approach is used, generation of activity data signal 3534 may not take place strictly in real time. Activity data signal 3534 can be identified through the use of other types of identity signal, as well, as described herein below.

In some aspects, identity signal sensor 3628 is distinct from activity sensor 3516. In an aspect, unobtrusive activity-detection system 3508 includes an audio signal sensor 3630 for sensing an audio signal including speech from patient 3502 at the patient location, and patient identification circuitry 3622 includes speech analysis circuitry 3632 for identifying at least a portion of the audio signal that resembles known speech of the patient. In an aspect, activity detection circuitry 3522 is configured to identify the at least one section of the at least one activity signal 3518 by activity in activity signal 3518 that corresponds (e.g., spatially and/or temporally) to the presence of patient 3502 detected by speech analysis circuitry 3632. For example, a continuous speech system may be used for identifying the speaker, as described in Chandra, E. and Sunitha, C., "A Review on Speech and Speaker Authentication System using Voice Signal Feature Selection and Extraction," IEEE International Advance Computing Conference, 2009. IACC 2009, Page(s): 1341-1346, 2009 (DOI: 10.1109/IADCC.2009.4809211), which is incorporated herein by reference. In an aspect, patient identification circuitry 3622 is configured to analyze identity signal 3624 to determine the presence of the patient based on frequency analysis of the audio identity signal. Magnitude or phase spectral analysis may be used, as described in McCowan, I.; Dean, D.; McLaren, M.; Vogt, R.; and Sridharan, S.; "The Delta-Phase Spectrum With Application to Voice Activity Detection and Speaker Recognition," IEEE Transactions on Audio, Speech, and Language Processing, 2011, Volume: 19, Issue: 7, Page(s): 2026-2038 (DOI: 10.1109/TASL.2011.2109379), which is incorporated herein by reference.

In an aspect, unobtrusive activity-detection system 3508 includes an imaging device 3634 for sensing an image at the patient location, wherein the patient identification circuitry 3622 includes image analysis circuitry 3636 for identifying a presence of the patient in the image. For example, in an aspect image analysis circuitry 3636 includes facial recognition circuitry 3638, configured to analyze the image to determine the presence of the patient through facial recognition. For example, in an aspect facial recognition circuitry 3638 uses approaches as described in Wheeler, Frederick W.; Weiss, R. L.; and Tu, Peter H., "Face Recognition at a Distance System for Surveillance Applications," Fourth IEEE International Conference on Biometrics: Theory Applications and Systems (BTAS), 2010 Page(s): 1-8 (DOI: 10.1109/BTAS.2010.5634523), and Moi Hoon Yap; Ugail, H.; Zwiggelaar, R.; Rajoub, B.; Doherty, V.; Appleyard, S.; and Hurdy, G., "A Short Review of Methods for Face Detection and Multifractal Analysis," International Conference on CyberWorlds, 2009. CW '09, Page(s): 231-236 (DOI: 10.1109/CW.2009.47), both of which are incorporated herein by reference.

In an aspect, image analysis circuitry 3636 includes gait/posture recognition circuitry 3640, which is configured to analyze the image to determine the presence of the patient through gait or posture recognition. Identification of the patient based on gait analysis can be performed, for example, by methods as described in U.S. Pat. No. 7,330,566, issued Feb. 12, 2008 to Cutler, and Gaba, I. and Kaur P., "Biometric Identification on The Basis of BPNN Classifier with Other Novel Techniques Used For Gait Analysis," Intl. J. of Recent Technology and Engineering (IJRTE) ISSN: 2277-3878, Vol. 2, issue 4, September 2013, pp. 137-142, both of which are incorporated herein by reference.

In an aspect, unobtrusive activity-detection system 3508 includes a biometric sensor 3642 for sensing a biometric signal from the patient, wherein the patient identification circuitry 3622 includes biometric signal analysis circuitry 3644 for analyzing the biometric signal to determine the presence of the patient. Biometric identification can include face and gait recognition, as described elsewhere herein, and recognition based on a variety of other physiological or behavioral characteristics, such as fingerprints, voice, iris, retina, hand geometry, handwriting, keystroke pattern, etc., e.g., as described in Kataria, A. N.; Adhyaru, D. M.; Sharma, A. K.; and Zaveri, T. H., "A Survey of Automated Biometric Authentication Techniques" Nirma University International Conference on Engineering (NUiCONE), 2013, Page(s): 1-6 (DOI: 10.1109/NUiCONE.2013.6780190), which is incorporated herein by reference. U.S. Pat. No. 8,229,178 issued Jul. 24, 2012 to Zhang et al., which is incorporated herein by reference, describes a method for acquiring a palm vein image with visible and infrared light and extracting features from the image for authentication of individual identity. Biometric identification can be based on imaging of the retina or iris, as described in U.S. Pat. No. 5,572,596 issued to Wildes et al. on Nov. 5, 1996 and U.S. Pat. No. 4,641,349 issued to Flom et al. on Feb. 3, 1987, each of which is incorporated herein by reference. Combinations of several types of identity signals can also be used (e.g., speech and video, as described in Aleksic, P. S. and Katsaggelos, A. K. "Audio-Visual Biometrics," Proceedings of the IEEE Volume: 94, Issue: 11, Page(s): 2025-2044, 2006 (DOI: 10.1109/JPROC.2006.886017), which is incorporated herein by reference).

In an aspect, user interface device 3612 is used for receiving an input indicative of at least one authentication factor from the user, and patient identification circuitry 3622 includes authentication circuitry 3646 for determining the presence of the patient based on the at least one authentication factor. The at least one authentication factor may include, for example, a security token, a password, a digital signature, and a cryptographic key. In an aspect, an authentication factor is received by unobtrusive activity-detection system via a user interface device 3612. User interface device 3612 can include various types of user interface devices or controls as are well known to those of ordinary skill in the art, including, but not limited to, keyboards, touchpads, touchscreens, pointing devices, (e.g., a mouse), joysticks, tracking balls, graphic interfaces, styluses, microphones or other voice interfaces, motion tracking interfaces, gesture interfaces (e.g., via a Kinect® or the like), brain-computer interfaces, buttons, or switches. User interface device 3612 can be integral to a communication device, e.g., a key pad of a cell phone. One or more user interface device 3612 in unobtrusive activity-detection system 3508 can be used to receive various types of user interfaces relating to operation of unobtrusive activity-detection system 3508, not limited to entry of an authentication factor. In an aspect, data input device 3614 is used to receive a data signal, which is used as the identity signal, and patient identification circuitry 3622 is configured to determine the presence of the patient based on the data signal.

In an aspect, unobtrusive activity-detection system 3508 includes a receiver 3700 for receiving a cell phone identification code, wherein the identity signal 3624 is a cell phone identification code, and wherein the patient identification circuitry 3622 is configured to determine the presence of the patient based on the cell phone identification code. The cell phone identification code may be, for example, an electronic serial number, a mobile identification number, and a system identification code.

In an aspect, unobtrusive activity-detection system 3508 includes a radio frequency identification (RFID) sensor 3652 for receiving an RFID signal from an RFIC device 3653 carried by or otherwise associated with patient 3502, wherein the identity signal 3624 is an RFID signal, and wherein the patient identification circuitry 3622 is configured to determine the presence of the patient based on the RFID signal. In an aspect, RFIC device 3653 is a passive RFID in a tag or chip associated with the patient. In an aspect, RFID sensor 3652 is an active RFID reader.

In an aspect, patient identification circuitry 3622 is configured to distinguish the presence of patient 3502 from the presence of another individual. In the event that the activity of another individual is detected by unobtrusive activity-detection system 3508, activity detected from the other individual should not be used to determine the compliance of patient 3502 with prescribed treatment regimen 3504. Accordingly, in an aspect, patient identification circuitry 3622 is configured to determine the presence of patient 3502 by determining that information contained in the identity signal matches patient information associated with the patient. For some types of identity signal (e.g., a password or device identity code), an exact match can be obtained. In other cases, a match is obtained by using a windowing, thresholding, or distance measurement to determine whether the identity signal (or information contained there) matches sufficiently closely patient information associated with the patient. In an aspect, patient identification circuitry 3622 is configured to distinguish the presence of the patient from the absence of the patient.

In an aspect, patient identification circuitry 3622 generates presence signal 3625 to indicate presence and/or identity of patient 3502. In an aspect, presence signal 3625 is provided as an input to activity detection circuitry 3522. Presence of patient 3502 may be indicated by a value of presence signal 3625. For example, in some aspects, presence signal 3625 is a binary signal; e.g., presence signal 3625 has a high value if the patient is present or a low value if the patient is not present (or vice versa). In an aspect, activity data 3528 is generated from activity signal 3518 only when the value of presence signal 3625 indicates that patient 3502 is present. Alternatively, in some aspects presence signal 3625 is a continuous valued signal that indicates the probability that the patient is present. For example, presence signal 3625 has a value of 100 if there is 100 percent probability that the patient is present, a value of zero if there is zero percent probability that the patient is present, or an intermediate value if there is an intermediate probability that the patient is present. It will be appreciated that in some contexts, the determination of whether the patient is present or absent will be relatively straightforward, in which case a binary presence signal may be appropriate, whereas in others (e.g., in cases where the presence of the patient must be distinguished from the presence of other individuals, e.g., from a conference call) there is some likelihood of error in identifying the presence of the patient (with the likelihood of error potentially dependent upon the number and identity of the other individuals present), such that an indication of the probability that the patient is present may be more appropriate. In some aspects, various device functions (e.g., acquisition of activity data, performance of activity analysis, or transmission of activity data signal 3534 to the monitoring location) are initiated in response to detection of the presence of patient 3502. In some aspects, presence of patient 3502 is a necessary but not sufficient condition for performance of particular device functions. For example, data may be collected at certain times of day, contingent upon the presence of patient 3502. In another aspect, data is collected when patient 3502 is present and initiates a particular activity.

In an aspect, activity detection circuitry 3522 is configured to process the at least one activity signal to exclude at least one portion of the at least one activity signal that does not contain activity of patient 3502, e.g., by excluding portions of the signal that contain no activity, or that contain activity of someone other than patient 3502.

In an aspect, activity detection circuitry 3522 is configured to identify at least one section 3524 of the at least one activity signal containing an activity pattern corresponding to performance of an activity of daily life, for example, hygiene, washing, eating, dressing, brushing teeth, brushing hair, combing hair, preparing food, interacting with another person, interacting with an animal, interacting with a machine, interacting with an electronic device, or using an implement.

In an aspect, activity detection circuitry 3522 is configured to identify at least one section of the at least one activity signal containing an activity pattern corresponding to performance of a motor activity. Examples of motor activities are typing, providing an input via an input device, providing an input via a keyboard, providing an input via a touchscreen, providing an input via a pointing device, controlling an entertainment device or system, controlling a game device or system, controlling a vehicle system, or walking.

In an aspect, unobtrusive activity-detection system 3508 includes one or more physiological sensors 3732. In some aspects, physiological sensor 3732 provides physiological activity signal 3780 to activity detection circuitry 3522. In an aspect, information from physiological activity signal 3780, taken in combination with activity signal 3518, provides supplemental information that aids in determining compliance of patient 3502 with prescribed treatment regimen 3504. In some aspects, physiological activity data signal 3782, including physiological activity data based on information from physiological activity signal 3780 is transmitted to a monitoring system for further analysis.

In an aspect, activity analysis circuitry 3526 is configured to process the at least one section 3524 of the at least one activity signal to determine at least one non-speech activity pattern 3520 of the patient. In an aspect, activity analysis circuitry 3526 is configured to generate activity data 3528 that includes the at least one non-speech activity pattern 3520 of the patient. In addition, in an aspect, activity analysis circuitry 3526 includes an activity analyzer 3650 for assessing the at least one activity pattern to determine at least one activity parameter 3651 indicative of whether the patient has complied with the treatment regimen, and wherein the activity analysis circuitry 3526 is configured to generate activity data 3528 that includes the at least one activity parameter. In various aspects, activity analysis circuitry 3526 is configured to determine activity patterns or parameters. In an aspect, an activity pattern characterizes one or both of coarse and fine temporal patterns of activity (e.g., whether an activity occurs at a particular time of day, such as morning, afternoon, evening, or night; frequency of occurrence of the activity during a particular time window). In an aspect, an activity pattern characterizes amplitude or intensity of the activity (e.g., how forcefully the patient strikes a key on a keyboard, or magnitude of body movement). In an aspect, an activity pattern includes the location at which an activity is performed. In an aspect, an activity pattern includes details regarding the substance of the activity (e.g., if the activity is selecting a song on a music player, the activity pattern includes information regarding the specific song selected). Activity parameters may include, but are not limited to, activity performance error rate, activity performance rate, activity performance time, activity performance frequency (e.g., repetitions of an activity), activity performance variability (including amount of variability, or lack thereof), or activity performance accuracy.

In an aspect, activity analysis circuitry 3526 includes a comparator 3654 for comparing the at least one non-speech activity pattern 3520 with at least one characteristic activity pattern 3552 to determine whether the patient has complied with the treatment regimen. In an aspect, comparator 3654 is configured to compare non-speech activity pattern 3520 with a plurality of characteristic activity patterns 3552, 3659, and 3660 (three characteristic activity patterns are provided as an example but the comparison is not limited to any specific number of characteristic activity patterns).

In an aspect, activity analysis circuitry 3526 is configured to determine that the patient 3502 has failed to comply with the treatment regimen. In an aspect, activity analysis circuitry 3526 is configured to determine that the patient has complied with the treatment regimen.

In an aspect, activity analysis circuitry 3526 is configured to determine whether the patient has complied with the treatment regimen based upon a determination of whether the activity data 3528 represents at least one of a plurality of characteristic activity pattern(s) 3552, 3659, and 3660. (Again, three patterns are provided as examples but comparison can be made to any number of characteristic activity patterns).

The result of the comparison performed by comparator 3654 is a determination that the activity data 3528 (or non-speech activity pattern 3520 or activity parameter 3651 derived therefrom) either does, or does not, match one or more characteristic activity data sets 3656, 3657, 3658, patterns 3552, 3659, 3660, or parameters 3661, 3662, 3663. It will be appreciated that in various aspects, activity analysis circuitry 3522 can be configured to determine both compliance and non-compliance, and additionally, or alternatively, level of compliance (either at specific levels or simply partial compliance). In an aspect, if there is a match, notification 3691 is generated by notification circuitry 3690 regarding whether the patient has complied with the prescribed treatment regimen. In practice, the comparison performed by comparator 3654 (which may include thresholding, windowing, distance computation, for example, as discussed herein above) will result in production of a signal that indicates at least whether the patient has complied with the prescribed treatment regimen, and alternatively, or in addition, a level of compliance with the prescribed treatment regimen. In some cases, a medical care provider at the monitoring location (or another party or entity concerned with the patient's health and well-being, such as a parent, family member, caretaker, healthcare provider, insurance company, etc.) is notified only if the patient has failed to comply with the prescribed treatment regimen. Alternatively, in some aspects the medical care provider or other party/entity is notified when the patient is in compliance with the prescribed treatment regimen. In some aspects, notification can be provided by transmitting a notification 3691 generated by notification circuitry 3690 to the monitoring location with transmitting device 3532, or to a wireless device, e.g., a remote device at the patient location, using wireless notification circuitry 3694.

In an aspect, transmitting device 3532 includes a wireless transmitter 3670, which may, for example, transmit a signal to a wireless router 3672 or a cellular network 3674. In another aspect, transmitting device 3532 includes a computer network connection 3676, e.g., an Ethernet connection 3678. In another aspect, transmitting device 3532 includes a communication port 3680. Communication port 3680 may provide for communication with a computer drive 3682 or USB device 3684.

In an aspect, unobtrusive activity-detection system 3508 includes notification circuitry 3690 for generating a notification 3691 indicative of whether the patient has complied with the treatment regimen. Notification circuitry 3690 may include, for example, email generation circuitry 3692 for generating an email notification, wireless notification circuitry 3694 for generating a notification to be transmitted to a wireless device, data storage circuitry 3696 for storing a notification in a data storage device, and audio alarm circuitry 3698 for generating an audio notification to be delivered with audio source 3699.

Compliance or lack thereof can be represented by appropriate text or numerical value in a displayed report or email, e.g., reported by notification circuitry 3690, or represented by a binary value in data stored by data storage device 3606. Alternatively, or in addition, level of compliance can be represented by a continuous value (e.g., percent compliance) or a text descriptor selected from a number of text descriptors corresponding to different levels of compliance (e.g., "non-compliance," "low compliance," "intermediate compliance," "near-full compliance," "full compliance"). In an aspect, notification circuitry 3690 provides for formatting data included in notification 3691 appropriately (e.g., by including appropriate text to accompany numerical data values) and for deciding whether and how to report the conclusion, based upon user preferences. For example, who is notified (patient versus medical care provider versus family member) or how notification is provided (stored in an event record, via email, or via a text message to a cell phone) may depend on the patient's level of compliance and the specifics of the patient. In some aspects, notification circuitry 3690 can generate different levels of notifications depending on how serious a problem non-compliance is likely to be for the patient. Generating a notification may include retrieving a stored notification 3686 from data storage device 3606, e.g., selected from among one or more notifications 3686 stored in data storage device 3606. Notifications may take the form of text or numerical codes, for example.

In an aspect, notification circuitry 3690 includes audio alarm circuitry 3698 for generating an audio alarm, e.g., a tone or voice alert to be delivered via an audio source (e.g., a speaker, bell, buzzer, beeper, or the like). In an aspect, notification circuitry 3690 provides a notification to patient 3502, e.g., by generating an audio alarm via the audio source or causing a text message to be displayed on a display of unobtrusive activity-detection system 3508, or a device in communication therewith, e.g., a cell phone or computing system used by patient 3502. A notification to the patient could take the form of a reminder to take a medication or contact a medical care provider, for example. In another aspect, notification circuitry 3690 uses wireless notification circuitry 3694 to transmit a notification (e.g., via wireless transmitter 3670) to a wireless device such as a pager, cell phone, or other wireless device used by a medical care provider or family member interested in tracking the status of the patient. In another aspect, notification circuitry 3690 includes data storage circuitry 3696 for storing a notification in a data storage device 3606. For example, in an aspect, data storage device 3606 provides for storage of a notification in event history 3697 in conjunction with information regarding the time at which the notification was generated (obtained, for example from timing circuitry 3602). In an aspect, information stored in event history 3697 becomes a part of the subject's electronic medical records, and may ultimately be transferred to the monitoring system or other location. In an aspect, timing circuitry 3602 includes a clock and/or timer, for example.

Figure 37:
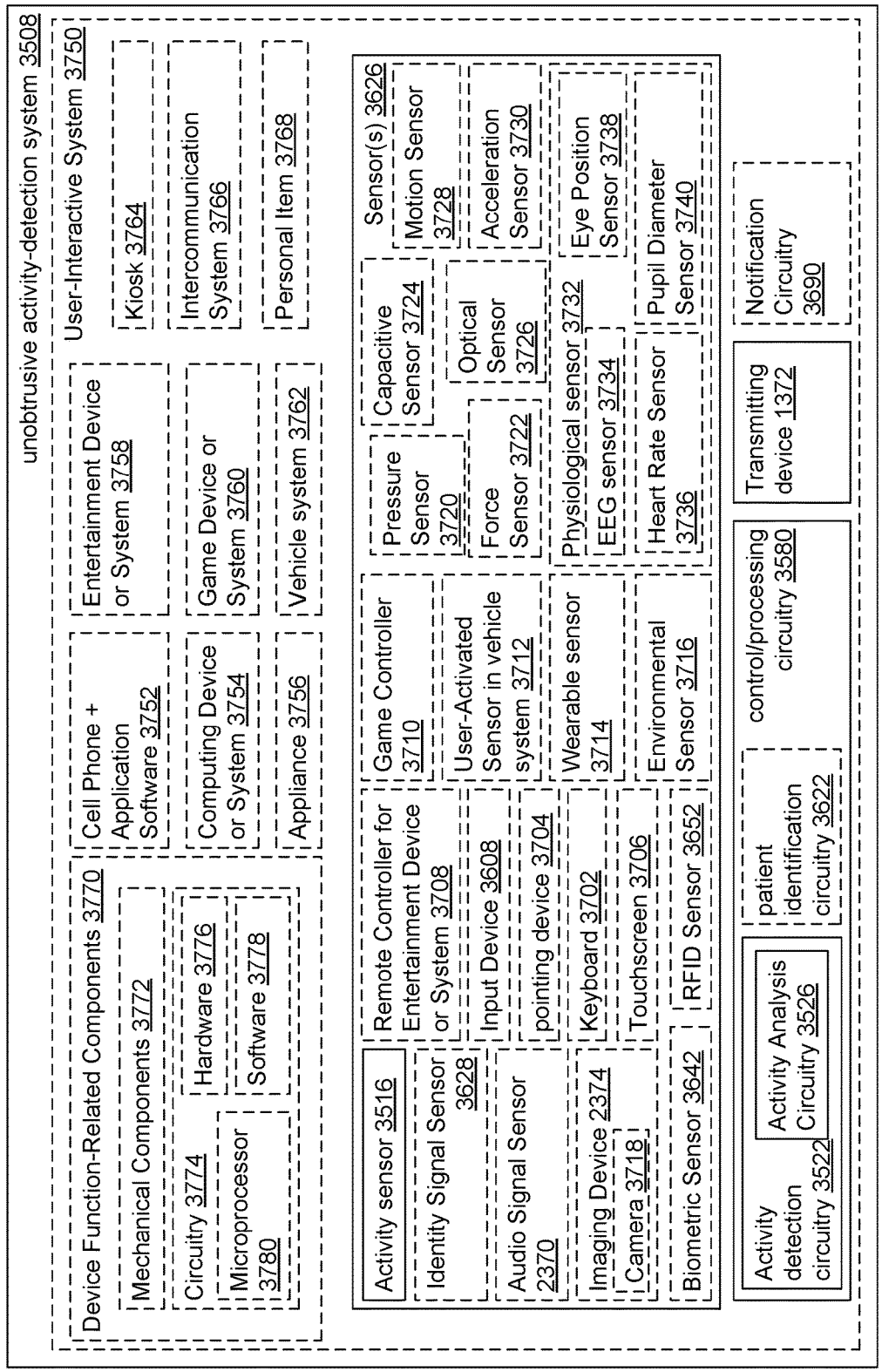
FIG. 37 is a block diagram showing further details of the unobtrusive activity-detection system of FIG. 36.

FIG. 37 depicts details of unobtrusive activity-detection system 3508, showing additional details and additional and/or alternative components relative to what is shown in FIG. 36. As discussed in connection with FIG. 36, unobtrusive activity detection system 3508 includes a variety of sensors 3626, including one or more activity sensor 3516 and one of more identity signal sensor 3628. As discussed in connection with FIG. 36, in some aspects activity sensor 3516 is the same as identity signal sensor 3628, while in other aspects the activity and identity signal sensors are different sensors. Sensors 3626 may include one or more identity signal sensor 3628, including, but not limited to, one or more audio signal sensor 3630, biometric sensor 3642, RFID sensor 3652, or imaging device 3634. In an aspect, activity sensor 3516 includes a camera 3718 or other imaging device 3634, which, in combination with appropriate hardware and software, may form a motion capture device (e.g., a Kinect®- or PlayStation® 4 Camera-type controller) that detects movements and/or gestures. In various aspects, such devices include depth sensing and IR reflectance technology, built-in color camera, infrared (IR) emitter, and microphone array.

A motion capture device can be used to detect activity of the subject during gaming or during daily living activities. In various aspects, camera 3718 includes 2D and 3D cameras. Activity sensor 3516 includes one or more devices of one or more types capable of sensing activity of the patient. In various aspects, the at least one activity sensor 3516 includes one or more input device 3608 (as described in connection with FIG. 36 which may be, for example, a keyboard 3702, a pointing device 3704 (e.g., a computer mouse), or a touchscreen 3706. In various aspects, the at least one activity sensor 3516 includes one or more remote controller for an entertainment device or system 3708, or game controller 3710. In various aspects, the at least one activity sensor includes a user-activated sensor in a vehicle system 3712. In an aspect, activity sensor 3516 is a wearable sensor 3714 or an environmental sensor 3716. In an aspect, an environmental sensor 3716 includes one or more optical sensor 3726 or camera 3718 or other imaging device 3634, in the environment of the subject. In an aspect, an environmental sensor includes a sensor in the environment of the subject that senses proximity of the patient to an object in the environment. In an aspect, an environmental sensor is a sensor attached to an animal or person in the environment. In an aspect, activity sensor 3516 is attached to an item which the patient uses or interacts with, e.g., a comb, a toothbrush, an implement, a utensil, a tool, keys, etc. In an aspect, the at least one activity sensor 3516 includes an imaging device 3634, which may be, for example, a camera 3718. In other aspect, activity sensor 3516 includes one or more pressure sensor 3720, force sensor 3722, capacitive sensor 3724, optical sensor 3726, motion sensor 3728, or acceleration sensor 3730.

In an aspect, unobtrusive activity-detection system 3508 includes at least one physiological sensor 3732, operatively connected to the unobtrusive activity-detection system and configured to detect a physiological signal indicative of whether the patient has complied with the treatment regimen. For example, in an aspect, physiological sensor 3732 includes an EEG sensor 3734. In an aspect, EEG sensor 3734 is configured to detect an event-related potential. Event-related potentials, or "ERPs" correspond to attention of a subject to an event (e.g., the event captures the subject's interest). ERPs normally occur at a fixed latency relative to the event of interest; thus, if the time of occurrence of the event of interest is known, ERGs can be detected based on their latency relative to the event of interest. In addition, it is also possible to detect ERPs in the EEG based on their characteristic shape, without information regarding when the event of interest occurred. Various ERP parameters, such as amplitude, latency, and/or topography are changed in patients with brain-related disorders. See, e.g., Hansenne, "Event-Related Brain Potentials in Psychopathology: Clinical and Cognitive Perspectives," Psychologica Belgica 2006, vol. 46, iss. 1-2, pp. 5-36, and Wise et al., "Event-Related Potential and Autonomic Signs of Maladaptive Information Processing During an Auditory Oddball Task in Panic Disorder," International Journal of Psychophysiology 74 (2009) 34-44, both of which are incorporated herein by reference. Moreover, in some cases treatment of brain-related disorder, e.g., with pharmaceuticals, at least partially restores the ERP parameters to values observed in individuals without the disorder, as described in Sumiyoshi et al., "Neural Basis for the Ability of Atypical Antipsychotic Drugs to Improve Cognition in Schizophrenia," Frontiers in Behavioral Neuroscience," 16 Oct. 2013, Volume 7, Article 140, which is incorporated herein by reference. In an aspect, the number and/or nature of ERPs detected in the patient's EEG provides additional or alternative information regarding compliance of the patient with the treatment regimen. In other aspects, physiological sensor 3732 includes a heart rate sensor 3736, an eye position sensor 3738, or a pupil diameter sensor 3740. Heart rate can be sensed by various approaches, using sensors in a fitness band (for example, of the type described in U.S. Pat. No. 9,113,795, which is incorporated herein by reference), sensors attached to the skin, etc. using various methods known in the art. Eye position can be sensed using a method and system as described in U.S. Pat. No. 8,808,195 to Tseng et al., which is incorporated herein by reference, or by other methods described herein or known to those skilled in the relevant art. Eye position may include static or fixed eye position/gaze direction or dynamic eye position/eye movement. Pupil diameter can be measured, for example, by methods as described in U.S. Pat. No. 6,162,186 to Scinto et al., which is incorporated herein by reference. Abnormal pupillary function is observed, for example, in patients with Alzheimer's disease (As discussed in Fotiou et al., "Pupil Reaction to Light in Alzheimer's disease: Evaluation of Pupil Size Changes and Mobility", Aging Clin Exp Res 2007 October; 19(5):364-71 (Abstract), which is incorporated herein by reference.

Unobtrusive activity-detection system 3508 can be constructed and implemented in a variety of embodiments in which different devices and/or device components provide the functionality described herein. In an aspect, unobtrusive activity-detection system 3508 includes or is implemented on or in connection with various types of systems with which the patient interacts. In an aspect, unobtrusive activity-detection system 3508 is built into such a user-interactive system 3750. In another aspect, unobtrusive activity-detection system 3508 is constructed separately but used in combination with such a user-interactive system 3750. For example, unobtrusive activity-detection system 3508 may be attached to user-interactive system 3750, or operatively connected to user-interactive system 3750. In various aspects, unobtrusive activity-detection system 3508 can be constructed as a microprocessor-based system, either as a device that provides compliance monitoring in combination with some other functionality, or as a compliance monitoring system that is used independently, or as an add-on to a system which provides some other functionality.

In an aspect, activity sensor 3516, activity detection circuitry 3522, activity analysis circuitry 3526, and transmitting device 3532 are components of a cell phone 3752 configured with application software. In another aspect, activity sensor 3516, activity detection circuitry 3522, activity analysis circuitry 3526, and transmitting device 3532 are components of a computing device or system 3754. In another aspect, activity sensor 3516, activity detection circuitry 3522, activity analysis circuitry 3526, and transmitting device 3532 are components of an appliance 3756 (e.g., a household appliance such as a microwave oven, a washing machine, or a coffee maker). In another aspect, activity sensor 3516, activity detection circuitry 3522, activity analysis circuitry 3526, and transmitting device 3532 are components of an entertainment device or system 3758 (e.g., a TV, a DVD player, or a music player) or a game device or system 3760. In yet another aspect, activity sensor 3516, activity detection circuitry 3522, activity analysis circuitry 3526, and transmitting device 3532 are components of a vehicle system 3762. In an aspect, activity sensor 3516, activity detection circuitry 3522, activity analysis circuitry 3526, and transmitting device 3532 are components of a kiosk 3764. In particular, kiosk 3764 may be a medical kiosk used to provide health-related information, perform medical monitoring (e.g., take a blood pressure reading), dispense medication, and the like. In another example, kiosk 3764 may be an entertainment or gaming kiosk, for example, located in a public venue such as a shopping mall or airport.

In another aspect, activity sensor 3516, activity detection circuitry 3522, activity analysis circuitry 3526, and transmitting device 3532 are components of an intercommunication ("intercom") system 3766. In another aspect, activity sensor 3516, activity detection circuitry 3522, activity analysis circuitry 3526, and transmitting device 3532 are components of a personal item 3768. For example, personal item 3768 can be any of various types of personal items that are used by the patient in the course of carrying out activities of daily life, such that the patient's interaction with personal item 3768 may indicate compliance of the patient with a prescribed treatment regimen. For example, personal item 3768 may be a personal grooming article such as a comb, hair brush, or toothbrush; a tool or implement; a key or a key fob attached to one or more keys; a wearable item such as a wristwatch, an item of jewelry, eyeglasses, an article of clothing, footwear, hat, helmet, head covering, or hairband; or a wallet or purse. In an aspect, one or more of activity sensor 3516, activity detection circuitry 3522, activity analysis circuitry 3526, and transmitting device 3532 are operatively connected to personal item 3768; e.g., one or more components may be packaged separately from personal item 3768 but configured to be physically attached to personal item 3768. In some aspects, one or more components of unobtrusive activity detection system 3508 are not attached to the personal item 3768, but communicate with at least one component attached to or built into personal item 3768.

In addition to activity sensor 3516, activity detection circuitry 3522, activity analysis circuitry 3526, and transmitting device 3532 that form part of unobtrusive activity-detection system 3508, user-interactive system 350 includes device function-related components 3770, including, but not limited to, mechanical components 3772 and/or circuitry 3774, which may include hardware 3776, software 3778, and/or microprocessor 3780.

Figure 38:
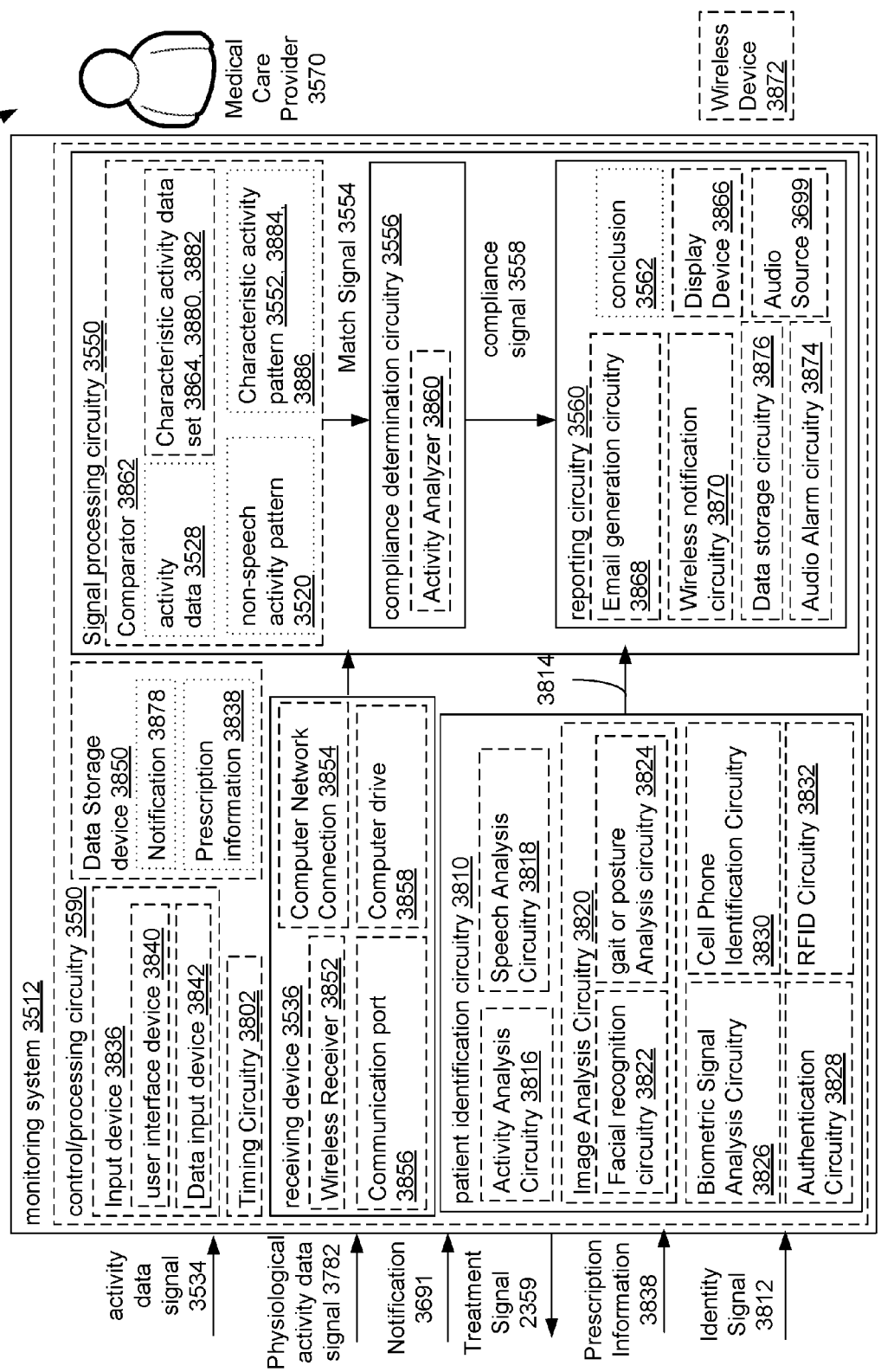
FIG. 38 is a block diagram of a monitoring system.

FIG. 38 depicts aspects of monitoring system 3512. As described briefly in connection with FIG. 35, monitoring system 3512 includes at least one receiving device 3536 for use at a monitoring location 3514 for receiving an activity data signal 3534 transmitted to monitoring location 3514 from a patient location. Activity data signal 3534 contains activity data 3528 representing at least one non-speech activity pattern 3520 in activity sensed from a patient with at least one activity sensor in an unobtrusive activity-detection system (e.g., unobtrusive activity-detection system 3508 at patient location 3510 as shown in FIG. 35) during performance of the non-speech activity by the patient. Monitoring system 3512 also includes signal processing circuitry 3550, which is configured to analyze activity data signal 3534 to determine whether the activity data 3528 represents at least one non-speech activity pattern 3520 that matches at least one characteristic activity pattern 3552. In addition, monitoring system 3512 includes compliance determination circuitry 3556 configured to determine whether the patient has complied with the prescribed treatment regimen based upon whether the activity data 3528 represents the non-speech activity pattern 3520 that matches the at least one characteristic activity pattern 3552, and reporting circuitry 3560 configured to report a conclusion 3562 based on the determination of whether the patient has complied with the treatment regimen.

In an aspect, signal processing circuitry 3550 is configured to analyze the activity data signal 3534 to identify at least one non-speech activity pattern that corresponds to unprompted performance of the non-speech activity by the patient. For example, in an aspect, signal processing circuitry 3550 identifies non-speech activity based upon detectable patterns in the activity data signal, without relying upon information regarding timing of activity relative to a prompt. Analysis of activity data and/or activity patterns is performed substantially as discussed in connection with activity analysis circuitry 3526 in FIG. 36.

In an aspect, monitoring system 3512 includes timing circuitry 3802, which may include a clock or timer device, and function in a manner substantially similar to timing circuitry 3602 in unobtrusive activity-detection system 3508 as described in connection with FIG. 36. In an aspect, timing circuitry 3802 is configured to control timing of operation of at least a portion of the system to perform substantially continuously the operation of receiving the activity data signal 3534 with the at least one receiving device 3536. Receiving activity data signal 3534 substantially continuously includes receiving a signal substantially without interruption, or sampling activity data signal 3534 at a rate that is sufficiently high to capture any meaningful variations in the activity sensed by the sensor, as discussed herein above in connection with timing circuitry 3602. In an aspect, timing circuitry 3802 is configured to control timing of operation of at least a portion of monitoring system 3512 to perform intermittently at least one of receiving the activity data signal 3534 with the at least one receiving device 3536, analyzing the activity data signal 3534 with signal processing circuitry 3550, determining with compliance determination circuitry 3556 at monitoring location 3514 whether the patient has complied with the treatment regimen, and reporting with reporting circuitry 3560 a conclusion 3562 based on the determination of whether the patient has complied with the prescribed treatment regimen.

In another aspect, timing circuitry 3802 is configured to control timing of operation of at least a portion of the system to perform according to a schedule at least one of receiving the activity data signal 3534 with the at least one receiving device 3536, analyzing the activity data signal 3534 with signal processing circuitry 3550, determining with compliance determination circuitry 3556 at the monitoring location 3514 whether the patient has complied with the treatment regimen, and reporting with reporting circuitry 3560 a conclusion 3562 based on the determination of whether the patient has complied with the prescribed treatment regimen. Timing of operation of monitoring system 3512 to form operations intermittently or according to a schedule can be controlled by timing circuitry 3802 configured by hardware and software, using control parameters which may be set or selected by a user, or preset during manufacture of the device, as described above.

In some aspects, non-speech activity pattern 3520 is an activity pattern corresponding to performance of a motor activity, which may include, for example, typing, providing an input via an input device, providing an input via a keyboard, providing an input via a touchscreen, providing an input via a pointing device, controlling a game device or system, controlling an entertainment device or system, controlling a vehicle system, or walking. In some aspects, non-speech activity pattern 3520 is an activity pattern corresponding to performance of an activity of daily life, for example, hygiene, washing, eating, dressing, brushing teeth, brushing hair, combing hair, preparing food, interacting with another person, interacting with an animal, interacting with a machine, interacting with an electronic device, or using an implement.

In various aspects, activity data signal 3534 contains activity data 3528 including data from various types of sensors, as described in connection with FIG. 37, e.g., a pressure sensor, a force sensor, a capacitive sensor, an imaging device, a motion sensor, a motion capture device, an acceleration sensor, an optical sensor, a camera. In various aspects, activity data 3528 represents one or more of a keystroke pattern, an activity performance pattern, an activity performance rate, an activity performance time, an activity performance frequency, an activity performance variability, an activity performance accuracy, or an activity performance error rate.

In an aspect, monitoring system 3512 includes patient identification circuitry 3810, which is configured to determine a presence of the patient from at least one identity signal 3812 received by receiving device 3536 at the monitoring location 3514 from the patient location; in connection therewith signal processing circuitry 3550 is configured to identify patient activity data corresponding to an activity of the patient based at least in part on the determination of the presence of the patient by the patient identification circuitry, as indicated by presence signal 3814 generated by patient identification circuitry 3810. In general, identity signals and determination of the presence of the patient are as described herein above in connection with FIG. 36.

In an aspect, identity signal 3812 includes at least a portion of the activity data 3528 in activity data signal 3534, wherein patient identification circuitry 3810 includes activity analysis circuitry 3816 configured to analyze the activity data 3528 to identify at least a portion of the activity data signal 3534 containing activity data representing an activity pattern that matches a known activity pattern of the patient.

In an aspect, identity signal 3812 includes a voice signal received from an audio sensor at the patient location, patient identification circuitry 3810 includes speech analysis circuitry 3818 for identifying at least a portion of the audio signal that resembles known speech of the patient, and signal processing circuitry 3550 is configured to identify activity data corresponding to an activity of the patient by identifying activity data corresponding to a portion of the audio signal that resembles known speech of the patient.

In an aspect, identity signal 3812 includes an image signal received from an imaging device at the patient location, wherein the patient identification circuitry includes image analysis circuitry 3820 configured to analyze the image signal to determine the presence of the patient, and wherein the signal processing circuitry 3550 is configured to identify activity data corresponding to an activity of the patient by identifying activity data corresponding to an image signal indicative of the presence of the patient. Image analysis circuitry 3820 may include facial recognition circuitry 3822 configured to analyze the image signal to determine the presence of the patient through facial recognition, or gait or posture analysis circuitry 3824 configured to analyze the image signal to determine the presence of the patient through gait or posture recognition.

In another aspect, identity signal 3812 includes a biometric signal from at least one biometric sensor at the patient location, and the patient identification circuitry 3810 includes biometric analysis circuitry 3826 configured to analyze the biometric signal to determine the presence of the patient, and signal processing circuitry 3550 is configured to identify activity data corresponding to an activity of the patient by identifying activity data corresponding to a biometric signal indicative of a presence of the patient.

In another aspect, identity signal 3812 include includes at least one authentication factor (e.g., one or more of a security token, a password, a digital signature, and a cryptographic key), and patient identification circuitry 3810 includes authentication circuitry 3828.

In another aspect, identity signal 3812 includes a device identification code, which identifies unobtrusive activity-detection system 3508, a component thereof, or an associated device. In an aspect, identity signal 3812 includes a cell phone identification code (e.g., an electronic serial number, a mobile identification number, and a system identification code) and patient identification circuitry 3810 includes cell phone identification circuitry 3830. In some aspects, identity signal 3812 includes a device identification code that identifies a computing system or device, a stand-alone microprocessor-based system, or a component thereof. A device identification code can serve to identify a patient (e.g., patient 3502 in FIG. 35 and FIG. 36) providing the device thus identified is consistently used only by the patient. Identifying the patient based on device identification code may be done, for example, if some or all components of unobtrusive activity-detection system 3508 are shared by multiple users but the device or component associated with the device identification code is used consistently by the patient. In an aspect, identity signal 3812 includes an RFID signal, and patient identification circuitry 3810 includes RFID circuitry 3832.

In an aspect, monitoring system 3512 includes input device 3836, which is used, for example, for receiving prescription information 3838 indicative of the treatment regimen prescribed to the patient. In an aspect, input device 3836 includes a user interface device 3840, for receiving information from a user (e.g., medical care provider 3570). In another aspect, input device 3836 includes a data input device 3842, for receiving information from a computing device or other electrical circuitry (e.g., like data input device 3614 described in connection with FIG. 36).

In an aspect, monitoring system 3512 includes at least one data storage device 3850, which may be used, for example, for storing prescription information 3838 indicative of the treatment regimen prescribed to the patient.

In various aspects, receiving device 3536 includes, for example, a wireless receiver 3852, computer network connection 3854, communication port 3856, or computer drive 3858.

In an aspect, compliance determination circuitry 3556 includes an activity analyzer 3650 for analyzing activity data 3528 to determine the non-speech activity pattern 3520, and a comparator 3862 for comparing the non-speech activity pattern 3520 represented by the activity data with the at least one characteristic activity pattern 3552. In some aspects, comparator 3862 is configured to compare the non-speech activity pattern 3520 represented by activity data 3528 with a plurality of characteristic activity patterns 3552, 3884, and 3886 (three are depicted in FIG. 38, but comparison can be made with any number of characteristic activity patterns).

In another aspect, compliance determination circuitry 3556 includes a comparator 3862 for comparing the activity data 3528 with at least one characteristic activity data set 3864 representing at least one characteristic activity pattern 3552. In an aspect, comparator 3862 is configured to compare activity data 3528 with a plurality of characteristic activity data sets 3864, 3880, and 3882, each said characteristic activity data set representing a characteristic activity pattern (three are depicted in FIG. 38, but comparison can be made with any number of characteristic activity data sets). For example, in some aspects compliance determination circuitry 3556 is configured to determine whether the patient has complied with the treatment regimen based upon a determination of whether the received activity data signal 3534 represents at least one of a plurality of characteristic activity patterns 3552.

In an aspect, compliance determination circuitry 3556 is configured to determine that the patient has failed to comply with the treatment regimen. In another aspect, compliance determination circuitry 3556 is configured to determine that the patient has complied with the treatment regimen.

In various aspects, reporting circuitry 3560 includes a display device 3866, email generation circuitry 3868 for generating an email notification, wireless notification circuitry 3870 for transmitting a notification to a wireless device 3872 (which may be, for example, a cell phone used by medical care provider 3570), audio alarm circuitry 3874 for generating an audio alarm, or data storage circuitry 3876 for storing a notification 3878 in data storage device 3850.

In an aspect, the at least one receiving device 3536 is adapted to receive a physiological activity data signal 3782 indicative of at least one physiological signal sensed with at least one physiological sensor operatively connected to the unobtrusive activity-detection system at the patient location. In an aspect, physiological activity data signal 3782 is indicative of whether the patient has complied with the treatment regimen. In various aspects, physiological activity data signal 3782 includes one or more of EEG data (including, for example, an event-related potential, wherein the event-related potential is related to performance of the non-speech activity by the subject), heart rate data, eye position data, or pupil diameter data.

Figure 39:
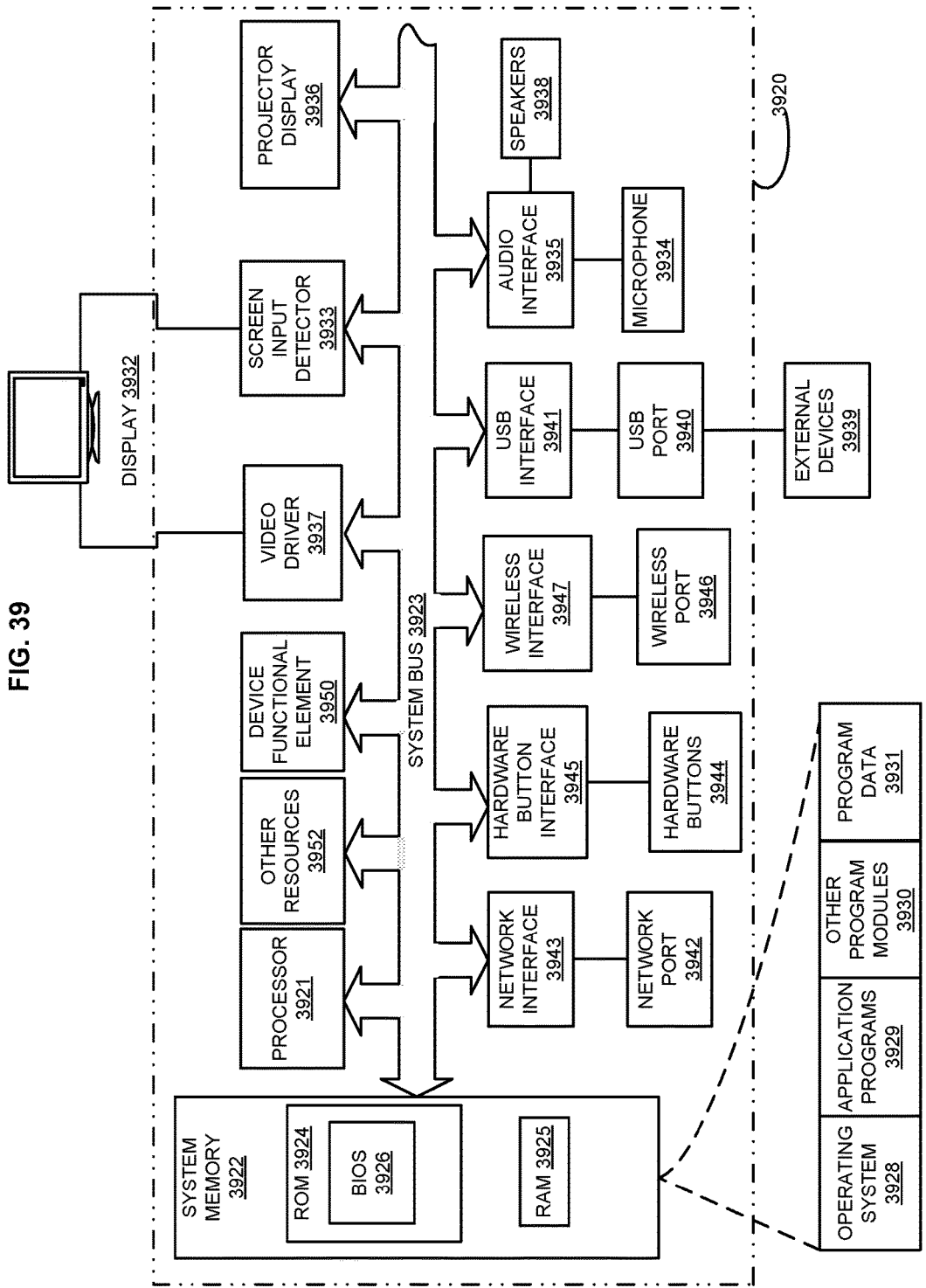
FIG. 39 illustrates an example embodiment of a thin computing device in which embodiments may be implemented.
Figure 40:
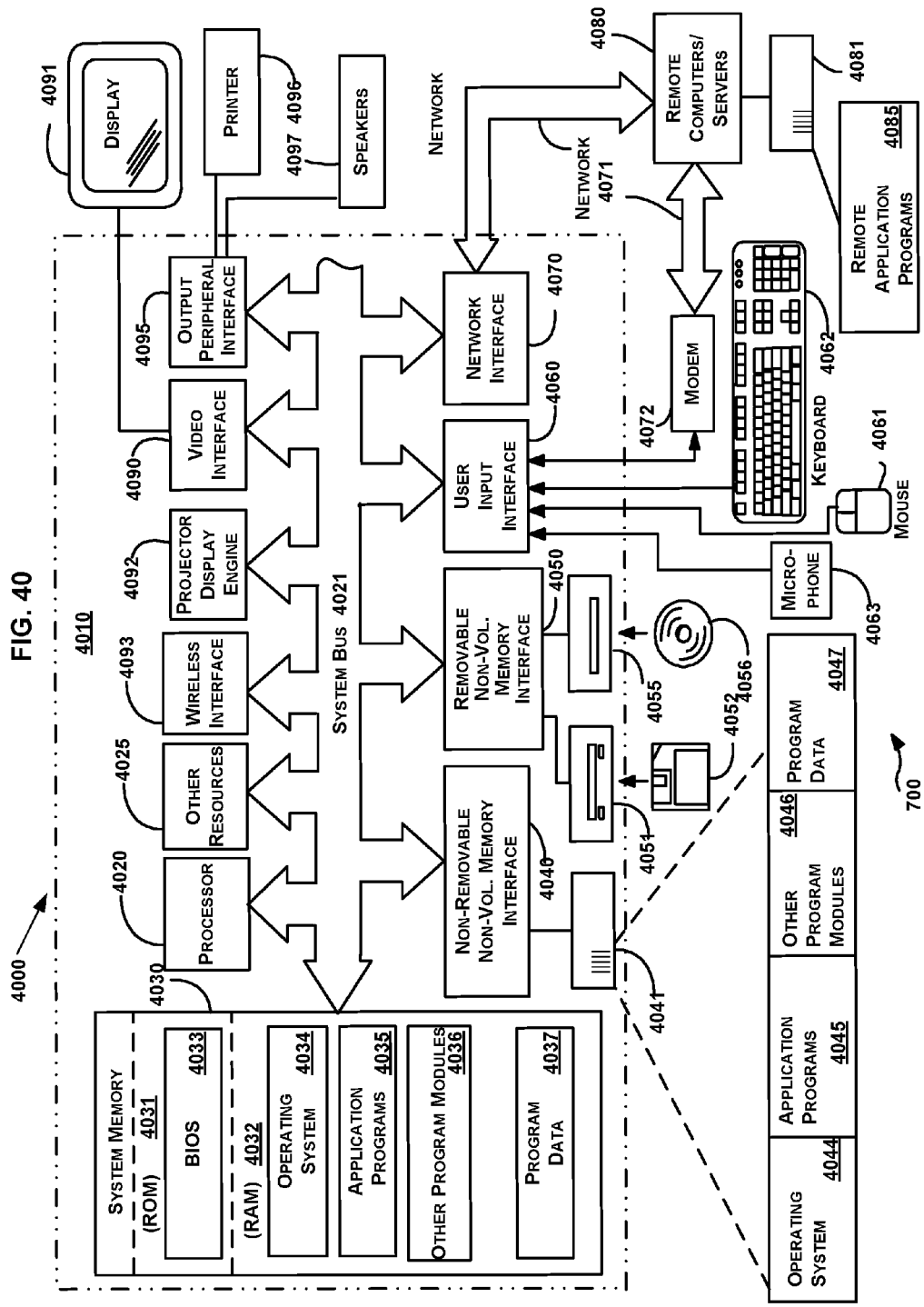
FIG. 40 illustrates an example embodiment of a computing system in which embodiments may be implemented.

FIGS. 39 and 40 provide brief, general depictions of environments in which embodiments may be implemented. FIG. 39 illustrates an example system that includes a thin computing device 3920, which may be included in an electronic device that also includes one or more device functional element 3950. For example, the electronic device may include any item having electrical or electronic components playing a role in a functionality of the item, such as a limited resource computing device, a wireless communication device, a mobile wireless communication device, an electronic pen, a handheld electronic writing device, a digital camera, a scanner, an ultrasound device, an x-ray machine, a non-invasive imaging device, a cell phone, a PDA, a Blackberry® device, a printer, a refrigerator, a car, and an airplane. In another example, the thin computing device may be included in a medical apparatus or device. In a further example, the thin computing device may be operable to communicate with a medical apparatus.

The thin computing device 3920 includes a processor 3921, a system memory 3922, and a system bus 3923 that couples various system components including the system memory 3922 to the processor 3921. The system bus 3923 may be any of several types of bus structures including a memory bus or memory controller, a peripheral bus, and a local bus using any of a variety of bus architectures. In an aspect, the system memory includes read-only memory (ROM) 3924 and random access memory (RAM) 3925. A basic input/output system (BIOS) 3926, containing the basic routines that help to transfer information between sub-components within the thin computing device 3920, such as during start-up, is stored in the ROM 3924. A number of program modules may be stored in the ROM 3924 or RAM 3925, including an operating system 3928, one or more application programs 3929, other program modules 3930 and program data 3931.

A user may enter commands and information into the computing device 3920 through input devices, such as a number of switches and buttons, illustrated as hardware buttons 3944, connected to the system via a suitable hardware button interface 3945. Input devices may further include a touch-sensitive display with suitable input detection circuitry, illustrated as a display 3932 and screen input detector 3933. The output circuitry of the touch-sensitive display 3932 is connected to the system bus 3923 via a video driver 3937. Other input devices may include a microphone 3934 connected through a suitable audio interface 3935, and a physical hardware keyboard (not shown). Output devices may include at least one display 3932 and at least one speaker 3938.

In addition to the display 3932, the computing device 3920 may include other peripheral output devices, such as a projector display 3936. Other external devices 3939 may be connected to the processor 3921 through a USB port 3940 and USB port interface 3941, to the system bus 3923. Alternatively, the other external devices 3939 may be connected by other interfaces, such as a parallel port, game port or other port. External devices 3939 include external input or output devices, e.g., a joystick, game pad, satellite dish, scanner, various types of sensors or actuators. Output signals include device control signals. The computing device 3920 may further include or be capable of connecting to a flash card memory (not shown) through an appropriate connection port (not shown). The computing device 3920 may further include or be capable of connecting with a network through a network port 3942 and network interface 3943, and through wireless port 3946 and corresponding wireless interface 3947 may be provided to facilitate communication with other peripheral devices, including other computers, printers, and so on (not shown). It will be appreciated that the various components and connections shown are examples and other components and means of establishing communication links may be used.

The computing device 3920 may be primarily designed to include a user interface. The user interface may include a character, a key-based, or another user data input via the touch sensitive display 3932. The user interface may include using a stylus (not shown). Moreover, the user interface is not limited to a touch-sensitive panel arranged for directly receiving input, but may alternatively or in addition respond to another input device such as the microphone 3934. For example, spoken words may be received at the microphone 3934 and recognized. Alternatively, the computing device 3920 may be designed to include a user interface having a physical keyboard (not shown).

The device functional elements 3950 are typically application specific and related to a function of the electronic device, and is coupled with the system bus 3923 through an interface (not shown). The functional elements may typically perform a single well-defined activity with little or no user configuration or setup, such as a cell phone connecting with an appropriate tower and transceiving voice or data information, or communicating with an implantable medical apparatus, or a camera capturing and saving an image.

In certain instances, one or more elements of the thin computing device 3920 may be deemed not necessary and omitted. In other instances, one or more other elements (e.g., other resources 3952) may be deemed necessary and added to the thin computing device.

FIG. 40 illustrates an example embodiment of a computing system in which embodiments may be implemented, shown as a computing system environment 4000. Components of the computing system environment 4000 may include, but are not limited to, a computing device 4010 having a processor 4020, a system memory 4030, and a system bus 4021 that couples various system components including the system memory to the processor 4020. The system bus 4021 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The computing system environment 4000 typically includes a variety of computer-readable media products. Computer-readable media may include any media that can be accessed by the computing device 4010 and include both volatile and non-volatile media, removable and non-removable media. By way of example, and not of limitation, computer-readable media may include computer storage media. By way of further example, and not of limitation, computer-readable media may include a communication media.

Computer storage media includes volatile and non-volatile, removable and non-removable media implemented in any method or technology for storage of information such as computer-readable instructions, data structures, program modules, or other data. Computer storage media includes, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by the computing device 4010. In a further embodiment, a computer storage media may include a group of computer storage media devices. In another embodiment, a computer storage media may include an information store. In another embodiment, an information store may include a quantum memory, a photonic quantum memory, or atomic quantum memory. Combinations of any of the above may also be included within the scope of computer-readable media.

Communication media may typically embody computer-readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media include wired media, such as a wired network and a direct-wired connection, and wireless media such as acoustic, RF, optical, and infrared media.

The system memory 4030 includes computer storage media in the form of volatile and non-volatile memory such as ROM 4031 and RAM 4032. A RAM may include at least one of a DRAM, an EDO DRAM, a SDRAM, a RDRAM, a VRAM, or a DDR DRAM. A basic input/output system (BIOS) 4033, containing the basic routines that help to transfer information between elements within the computing device 4010, such as during start-up, is typically stored in ROM 4031. RAM 4032 typically contains data and program modules that are immediately accessible to or presently being operated on by processor 4020. By way of example, and not limitation, FIG. 40 illustrates an operating system 4034, application programs 4035, other program modules 4036, and program data 4037. Often, the operating system 4034 offers services to applications programs 4035 by way of one or more application programming interfaces (APIs) (not shown). Because the operating system 4034 incorporates these services, developers of applications programs 4035 need not redevelop code to use the services. Examples of APIs provided by operating systems such as Microsoft's "WINDOWS" are well known in the art.

The computing device 4010 may also include other removable/non-removable, volatile/non-volatile computer storage media products. By way of example only, FIG. 40 illustrates a non-removable non-volatile memory interface (hard disk interface) 4040 that reads from and writes for example to non-removable, non-volatile magnetic media. FIG. 40 also illustrates a removable non-volatile memory interface 4050 that, for example, is coupled to a magnetic disk drive 4051 that reads from and writes to a removable, non-volatile magnetic disk 4052, or is coupled to an optical disk drive 4055 that reads from and writes to a removable, non-volatile optical disk 4056, such as a CD ROM. Other removable/non-removable, volatile/non-volatile computer storage media that can be used in the example operating environment include, but are not limited to, magnetic tape cassettes, memory cards, flash memory cards, DVDs, digital video tape, solid state RAM, and solid state ROM. The hard disk drive 4041 is typically connected to the system bus 4021 through a non-removable memory interface, such as the interface 4040, and magnetic disk drive 4051 and optical disk drive 4055 are typically connected to the system bus 4021 by a removable non-volatile memory interface, such as interface 4050.

The drives and their associated computer storage media discussed above and illustrated in FIG. 40 provide storage of computer-readable instructions, data structures, program modules, and other data for the computing device 4010. In FIG. 40, for example, hard disk drive 4041 is illustrated as storing an operating system 4044, application programs 4045, other program modules 4046, and program data 4047. Note that these components can either be the same as or different from the operating system 4034, application programs 4035, other program modules 4036, and program data 4037. The operating system 4044, application programs 4045, other program modules 4046, and program data 4047 are given different numbers here to illustrate that, at a minimum, they are different copies.

A user may enter commands and information into the computing device 4010 through input devices such as a microphone 4063, keyboard 4062, and pointing device 4061, commonly referred to as a mouse, trackball, or touch pad. Other input devices (not shown) may include at least one of a touch sensitive display, joystick, game pad, satellite dish, and scanner. These and other input devices are often connected to the processor 4020 through a user interface 4060 that is coupled to the system bus, but may be connected by other interface and bus structures, such as a parallel port, game port, or a universal serial bus (USB). Other devices that can be coupled to the system bus via other interface and bus structures include sensors of various types, for example.

A display 4091, such as a monitor or other type of display device or surface may be connected to the system bus 4021 via an interface, such as a video interface 4090. A projector display engine 4092 that includes a projecting element may be coupled to the system bus. In addition to the display, the computing device 4010 may also include other peripheral output devices such as speakers 4097 and printer 4096, which may be connected through an output peripheral interface 4095. Outputs may be sent to a variety of other types of devices, and are not limited to the example output devices identified here.

The computing system environment 4000 may operate in a networked environment using logical connections to one or more remote computers, such as a remote computer 4080. The remote computer 4080 may be a personal computer, a server, a router, a network PC, a peer device, or other common network node, and typically includes many or all of the elements described above relative to the computing device 4010, although only a memory storage device 4081 has been illustrated in FIG. 40. The network logical connections depicted in FIG. 40 include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing system environment 4000 is connected to the network 4071 through a network interface, such as the network interface 4070, the modem 4072, or the wireless interface 4093. The network may include a LAN network environment, or a WAN network environment, such as the Internet. In a networked environment, program modules depicted relative to the computing device 4010, or portions thereof, may be stored in a remote memory storage device. By way of example, and not limitation, FIG. 40 illustrates remote application programs 4085 as residing on computer medium 4081. It will be appreciated that the network connections shown are examples and other means of establishing a communication link between the computers may be used.

In certain instances, one or more elements of the computing device 4010 may be deemed not necessary and omitted. In other instances, one or more other elements (e.g., other resources 4025) may be deemed necessary and added to the computing device.

FIGS. 39 and 40 illustrate generalized forms of circuitry-based systems, in which systems as depicted in FIGS. 35-38 may be implemented. Although specific embodiments are described herein, those skilled in the art will appreciate that methods and systems as described herein can be implemented in various ways. Reference is made herein to various circuitry systems/subsystems (e.g., patient identification circuitry 3622, activity detection circuitry 3522, notification circuitry 3690 in FIG. 36, and patient identification circuitry 3810, reporting circuitry 3560, and signal processing circuitry 3550 in FIG. 38) which may be considered to be control/processing circuitry, and/or components thereof. In general, control/processing circuitry (e.g., control/processing circuitry 3580 and control/processing circuitry 3590 in FIG. 35) includes any or all of digital and/or analog components, one or more processor (e.g., a microprocessor), and includes memory and additional components as described in connection with FIGS. 39 and 40.

As discussed in connection with FIG. 35, transmitting device 3532 in unobtrusive activity-detection system 3508 and receiving device 3536 in monitoring system 3512 are configured to provide a communication link between the two locations. In various aspects, transmitting device 3532 and receiving device 3536 provide a wireless communication link. A wireless communication link may also be established between monitoring system 3512 and wireless device 3872, as shown in FIG. 38.

FIG. 41 illustrates an embodiment of an unobtrusive activity-detection system 4100 that is based on a cell phone 4102. In this example, activity detection circuitry 3522, activity analysis circuitry 3526, and transmitting device 3532 are components of a cell phone 4102, formed from standard cell phone hardware configured with application software. One or more touchscreen sensors 4104, which are used for receiving instructions for controlling phone 4102 entered by patient 4106, serve as activity sensors. One or more activity signal 4108 from touchscreen sensors 4104 is processed by touchscreen input processing application 4110. Activity signal 4108 represents the motion of the patient's finger on the touchscreen, as sensed by touchscreen sensors 4104. Touchscreen input processing application 4110 determines the timing of entry of instructions by the patient. In an aspect, it is not necessary to determine the specific instructions entered by the patient, but only to determine how often the patient is using the phone, and/or how quickly the patient is entering instructions into the phone. However, in other aspects, the specific instructions can be detected, e.g., to determine whether the patient is choosing to listen to music, play a game, send or read email, receive a phone call, or place a phone call. An EEG (electroencephalogram) sensor 4112 serves as a physiological sensor for providing further information relating to the brain-related functioning of patient 4106. EEG sensor 4112 includes electrodes built into earbuds (which are used by the patient 4106 for listening to phone calls, music, or other audio outputs provided by cell phone 4102). Sensed EEG signal 4114 is processed by EEG processing application 4122. Sensing of EEG signals with sensors that fit into the ear canal is described, for example, in U.S. Patent Publication 2003/0195588 to Fischell et al., and U.S. Patent Publication 2006/0094974 to Cain, both of which are incorporated herein by reference. See also Bleichner, et al., "Exploring Miniaturized EEG Electrodes for Brain-Computer Interfaces. An EEG You Do Not See?" Physiological Reports 2015, Vol. 3, Iss. 4,e12362, doi: 10.14814/phy2.12363, which is incorporated herein by reference. In an aspect, EEG sensor 4112 is used for detecting event-related potentials (ERPs) associated with a detectable event associated with operation of cell phone 4102. In an aspect, the detectable event is an event that can be detected by control/processing circuitry 3580 in cell phone 4102. For example, in various aspects, the detectable event includes providing notification of the arrival of an incoming call to patient 4106 (e.g., by ringing or vibration of cell phone 4102), providing notification of the arrival of an email message or impending calendared event with an audible tone or a pop-up message. As used herein, a "detectable" event is an event that results in a detectable change in control/processing circuitry 3580 of cell phone 4102. In principle, the "detectable" event is also expected to be detectable by patient 4106, at least at a sub-conscious level, with such detection of the event by the patient resulting in generation of an event-related potential that can be sensed with EEG sensor 4112. Because changes in amplitude, latency, and/or topography of event-related potentials have been observed in subjects with various brain-related disorders (Hansenne, "Event-Related Brain Potentials in Psychopathology: Clinical and Cognitive Perspectives," Psychologica Belgica 2006, vol. 46, iss. 1-2, pp. 5-36, which is incorporated herein by reference), changes in event-related potential production in response to a detectable event, or absence of an event-related potential in response to a detectable event provide information regarding the mental function of the patient, and hence whether the patient has complied with a prescribed treatment regimen. Motion sensor 4114 in wristband 4116 generates second activity signal 4118 representing motion of patient 4106. Second activity signal 4118 is processed by motion processing application 4120. Activity detection circuitry 3522 receives signals 4124, 4126, and 4128 from touchscreen input processing application 4110, motion processing application 4120, and EEG processing application 4122, respectively, which are received by activity detection circuitry 3522 and processed to generate activity data signal 3534. Signal 4124 from touchscreen input processing application 4110 supplies to activity detection circuitry information regarding how often the patient 4106 uses phone 4102 (summarizing the patient's entry of instructions by category, e.g., by providing the number of times the person placed a phone call, the number of times the patient looked at email, and the number of hours per day spent listening to music). Signal 4126 from motion processing application 4120 provides information regarding the patient's activity level (sensed by motion sensor 4114 in wristband 4116), and signal 4128 from EEG processing application 4122 provides information regarding how attentive the patient is to a the detectable event (e.g., percent of the time that an ERP was produced in response to a notification regarding the arrival of an email). ERP information and activity patterns relating to patient motion and touchscreen activity are processed in combination to determine compliance of patient 4106 with a prescribed treatment regimen.

Figure 42:
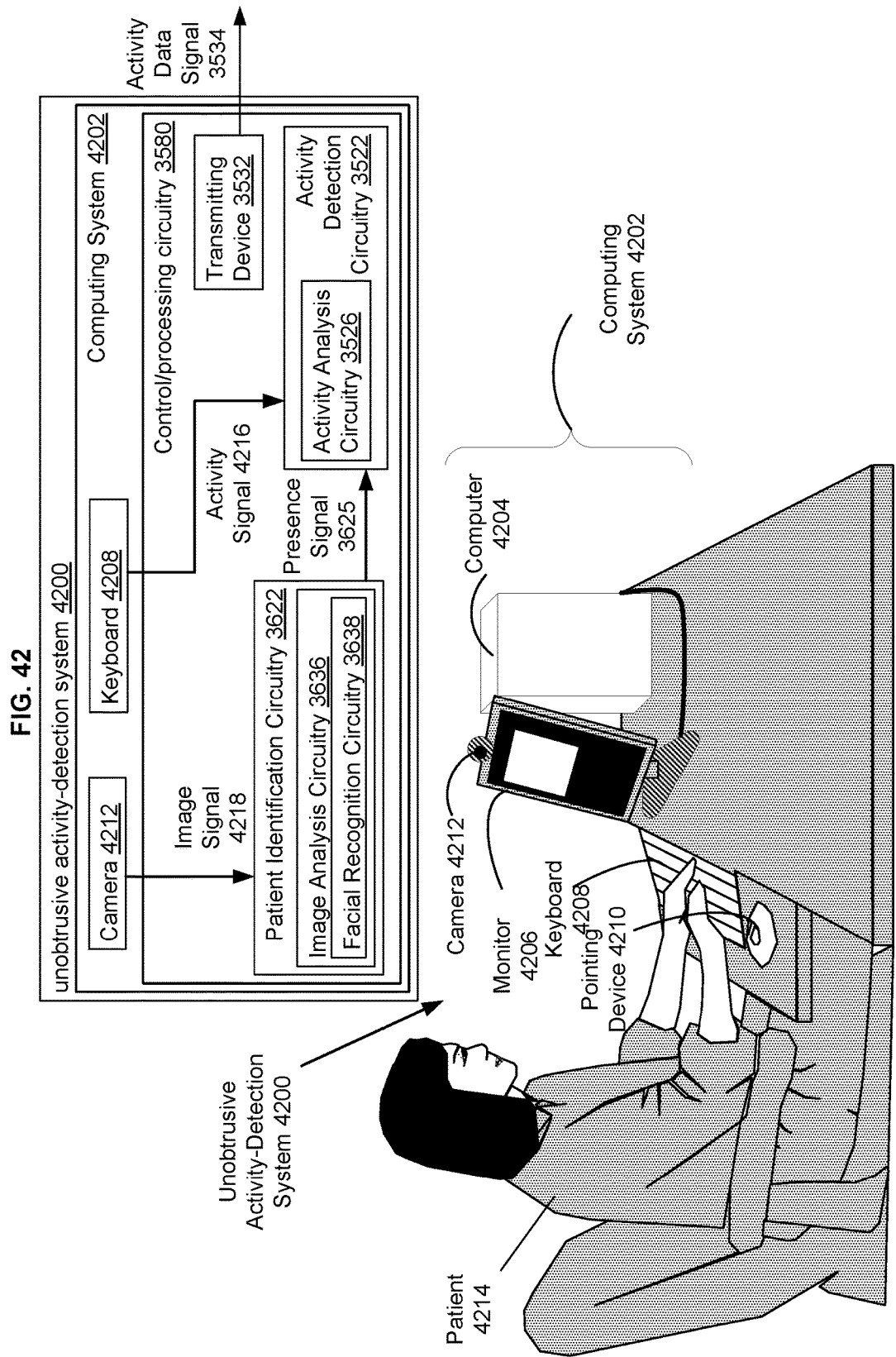
FIG. 42 is an illustration of an unobtrusive activity detection system implemented in a computing system.
Figure 43:
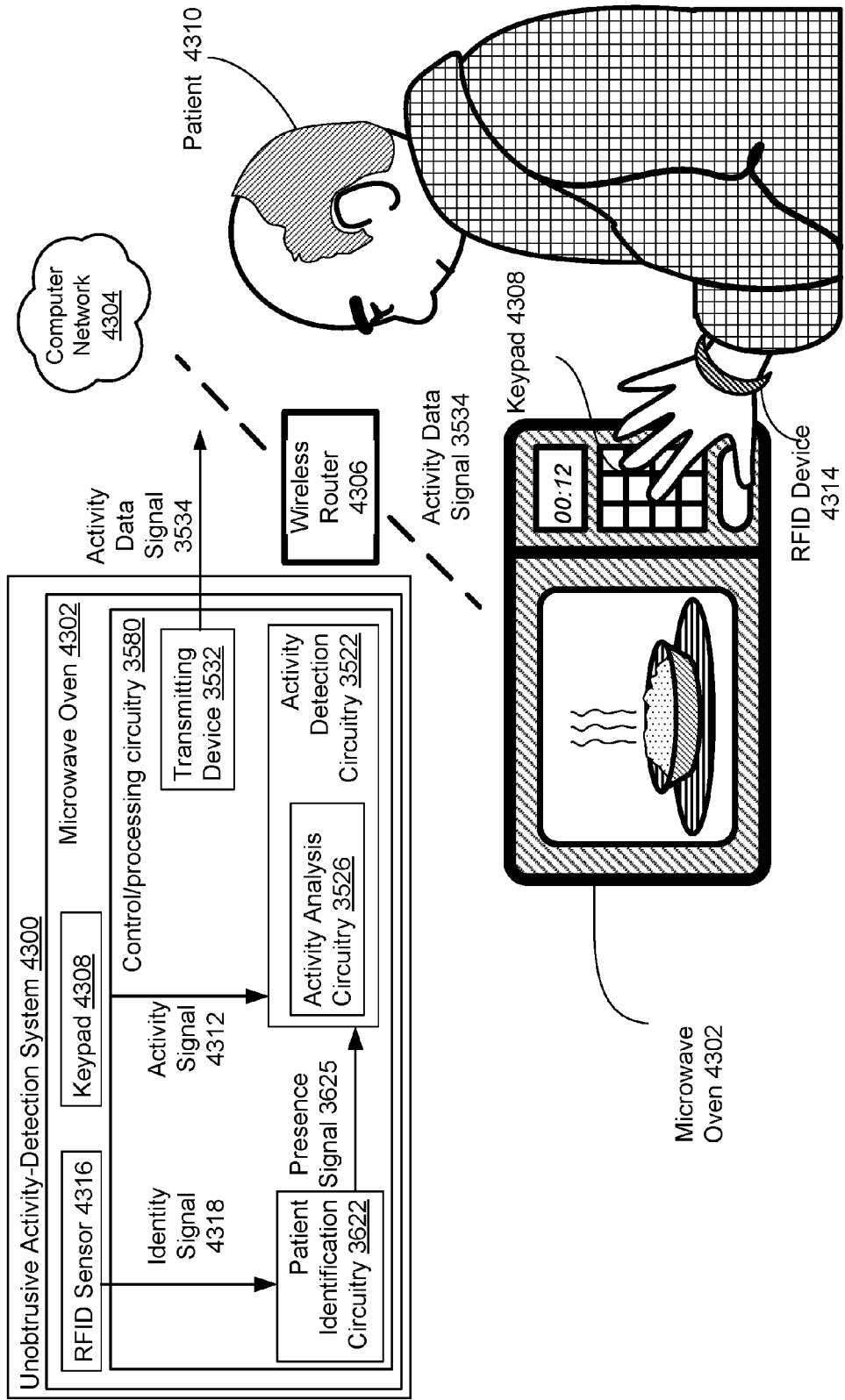
FIG. 43 is an illustration of an unobtrusive activity detection system implemented in a microwave oven.

FIG. 42 depicts an embodiment of an unobtrusive activity-detection system 4200, implemented in a computing system 4202. Computing system 4202 includes computer 4204, monitor 4206, keyboard 4208, pointing device 4210, and camera 4212, which is built into monitor 4206 in the present example. Computing system 4202 is used by patient 4214 to perform personal or work-related activities, such as (for example, and without limitation) creating and editing documents using word-processing software. In this example, keyboard 4208 serves as an activity sensor, providing activity signal 4216 to activity detection circuitry 3522. Other components of unobtrusive activity-detection monitoring system 4200 (e.g., activity analysis circuitry 3526, and transmitting device 3532) are components of a computing system 4202. In addition, camera 4212 provides an identify signal (image signal 4218) to patient identification circuitry 3622, where it is processed by facial recognition circuitry 3638 in image analysis circuitry 3636 to determine the identity/presence of patient 4214 to generate presence signal 3625. It will be appreciated that it may also be possible to determine the identity/presence of patient 4214 by utilizing login/password information provided when patient 4214 logs onto computer 4204 (or logs into a specific piece of program or online accounts) for authentication. Activity signal 4216 contains information regarding the patient's typing pattern, which is analyzed by activity analysis circuitry 3526, to generate activity data signal 3534, which is transmitted to a monitoring location by transmitting device 3532. Activity analysis circuitry 3526 may analyze typing patterns using, for example, techniques as described in U.S. Pat. No. 6,231,344 to Merzenich et al., U.S. Published Patent Application 2005/0084832 to Janssen et al., each of which is incorporated herein by reference FIG. 43 depicts an embodiment of an unobtrusive activity-detection system 4300 that is implemented in connection with a microwave oven 4302. Microwave oven 4302 is a "smart" oven that includes a circuitry that allows it to send data to and receive data from a computing network, for example, as described in, e.g., U.S. Pat. No. 8,631,063 to Helal et al., U.S. Pat. No. 9,113,795 to Hong et al., U.S. Pat. No. 8,667,112 to Roth et al., each of which is incorporated herein by reference. Microwave oven 4302 includes control/processing circuitry 3580 and communication circuitry (including transmitting device 3532), allowing it to connect to the computer network 4304 via a wireless router 4306 or other wireless communication device (e.g., a cell phone or laptop computer). Activity detection circuitry 3522, activity analysis circuitry 3526, and transmitting device 3532 are components of microwave oven 4302. Keypad 4308 of microwave oven 4302 is used as an activity sensor, providing an activity signal 4312 to activity detection circuitry 3522. When patient 4310 uses keypad 4308 to operate microwave oven 4302, activity signal 4312 is sent to activity detection circuitry 3522. In an aspect, the pattern of use of microwave oven, as indicated by activation of keypad 4308 (e.g., time of day that it is used, frequency of use during the day) may be indicative of the brain-related functioning of the patient. For example, a depressed patient may be less likely to make the effort to prepare food, and will use the microwave oven less than usual. In other cases the patient may use the microwave more often than is typical for that patient, or at unusual times of the day or night. A patient that is showing symptoms of dementia may have difficulty pressing the keys on the keypad in the appropriate sequence in order to heat food. Accordingly, accuracy of operation of the microwave oven (e.g., whether the patient presses keys in the proper sequence to select cooking time and temperature and turns on the oven, and how many attempts it takes to operate the oven properly) may be indicative of the patient's alertness or coordination. Identity of patient 4310 is determined by sensing an RFID signal from RFID device 4314, using RFID sensor 4316. Identity signal 4318 from RFID sensor 4316 is provided to patient identity circuitry 3622, which generates presence signal 3625, as discussed herein above. It is contemplated that RFID device 4314 is a passive RFID device, but in other embodiments an active RFID could be used. RFID device 4314 is depicted as taking the form of a wristband worn by patient 4310, but it could be embodied in a necklace, a key fob, an implant, clothing, or other form. As an alternative, patient 4310 could be identified by sensing an identification signal from a cell phone or smart watch carried by patient 4310.

FIG. 44 depicts an example of an unobtrusive activity-detection system 4400 that is incorporated into a game system 4402. Game system 4402 includes a game console 4404, game controller 4406 for providing control signals to game console 4404, and display 4408 driven by video output from game console 4404. Game controller 4406 functions as an activity sensor; as patient 4410 plays the game, signals from game controller 4406 are used as activity signal 4412, which is processed by activity detection circuitry 3522 and activity analysis circuitry 3526 in game console 4404. Sensing and processing of game controller signals, e.g., to determine reaction times, may be substantially as described in U.S. Pat. No. 5,913,310 to Brown, or U.S. Pat. No. 6,186,145 to Brown, both of which are incorporated herein by reference. It will be appreciated that while Brown describes a video game designed primarily for health care-related teaching purposes, the video game may be for entertainment purposes, and need not include an educational or medical component. Activity detection circuitry 3522 and activity analysis circuitry 3526 include special-purpose hardware and/or software incorporated into game console 4404 (in the form of an add-on card or software). Username/password information entered into game controller 4406 by patient 4410 is used as an authentication signal 4414 processed by authentication circuitry 3646 in patient identification circuitry 3622 to generate presence signal 3625 that indicates presence of the patient. Game console 4404 also includes transmitting device 3532, which is used for communicating with network 4420, including transmitting activity data signal 3534 to a monitoring location for processing as described elsewhere herein.

FIG. 45 depicts an example of an unobtrusive activity-detection system 4500 that is incorporated into a vehicle system 4502. Vehicle system 4502 includes one or more components of vehicle 4504, which are built into vehicle 4504 during manufacture or subsequently installed in vehicle 4504. Vehicle system components include vehicle controls 4506 (including, but not limited to ignition 4508, brakes 4510, steering 4512, lights 4514, accelerator 4516, or door locks 4518) and auxiliary systems 4520 (including, but not limited to, location sensing 4522, dashboard camera 4524, event recorder or "black box" 4526 used for tracking vehicle acceleration, deceleration, etc., entertainment system 4528, or communication system 4530). Communication system 4530 may include, for example, a telephone or radio system. The presence and/or identity of patient 4540 in vehicle 4504 is sensed by RFID sensor 4542, which detects RFID 4544 in key fob 4546 carried by patient 4540. Activity of patient 4540 is sensed by one or more vehicle system sensor 4550, including one or more sensors associated with vehicle controls 4506 or auxiliary systems 4520. A wide variety of types of patient activity can be sensed by vehicle system sensor 4550 to provide information regarding the patient's brain-related function. For example, in various aspects patient activity sensed by vehicle system sensor 4550 includes, but is not limited to acceleration, deceleration or steering of vehicle 4504, choice of music, activation/deactivation of lights or door locks, coordination (determined through analysis of video from dashboard cam), choice of location as assessed by location sensing (e.g., GPS) system, etc. In various aspects, rate, frequency, and consistency of sensor activation provide information regarding the patient's mental state. Activity signal 4552 from vehicle system sensor 4550 is provided to activity detection circuitry 3522 and activity analysis circuitry 3526, which are components of vehicle system 4502, and activity data signal 3534 from activity detection circuitry 3522 is transmitted by transmitting device 3532, which is also a component of a vehicle system 4502.

Figure 46:
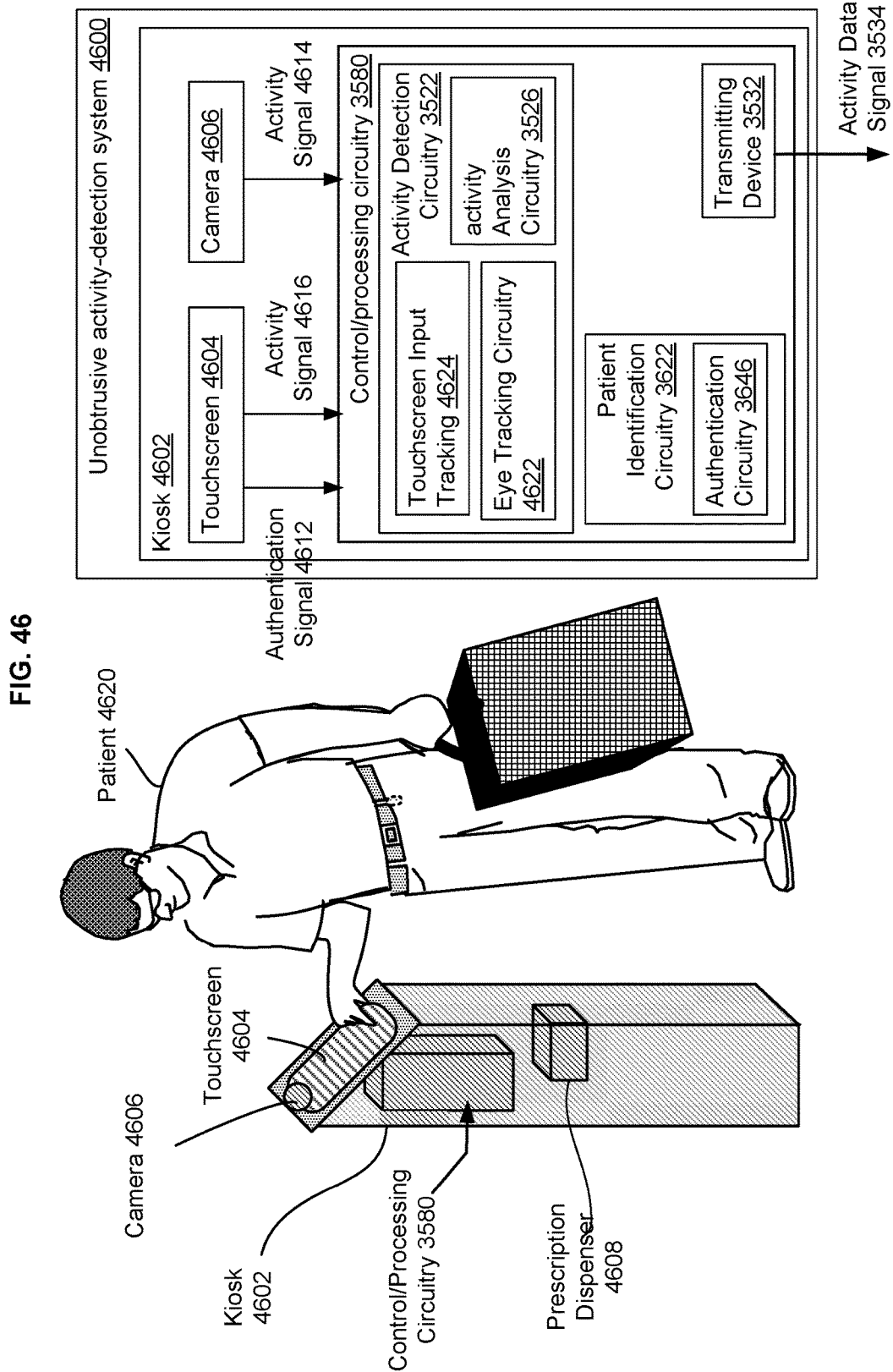
FIG. 46 is an illustration of an unobtrusive activity detection system implemented in a kiosk.

FIG. 46 depicts an example of an unobtrusive activity-detection system 4600 in which activity detection circuitry 3522, activity analysis circuitry 3526, and transmitting device 3532 for transmitting activity data signal 3534 to a monitoring location are components of a kiosk 4602 (e.g., as described generally in U.S. Pat. No. 9,135,403 to Tolmosoff, and U.S. Pat. No. 8,996,392 to Cashman et al., both of which are incorporated herein by reference). Kiosk 4602 is a medical kiosk used to provide health-related information, perform medical monitoring (e.g., take a blood pressure reading), dispense medication, and the like. Kiosk 4602 includes a touchscreen 4604, camera 4606, and prescription dispenser 4608. Operation of kiosk 4602 is controlled by control/processing circuitry 3580. Patient 4620 signs in to a personal healthcare account via kiosk 4602 by entering a login name and password via touchscreen 4604, by scanning an identification card, or by some other authentication method. Inputs from touchscreen 4604 are processed by touchscreen input tracking 4624. Authentication signal 4612 from touchscreen 4604 (or alternatively, from a card scanner) is provided to authentication circuitry 3646 in patient identification circuitry 3622. After signing into a personal healthcare account via kiosk 4602, patient 4620 is able to pick up a prescription via prescription dispenser 4608, or perform other healthcare-related activities. While patient 4620 interacts with kiosk 4602 via touchscreen 4604, camera 4606 captures an image of the patient's face, which is provided to control/processing circuitry 3580 as a first activity signal 4614. Eye movement has been shown to be indicative of brain-related state, and eye tracking circuitry 4622 is used to track the patient's eye position/direction of gaze and determine the patient's eye movement pattern to assess brain-related state, for example using an approach as described in U.S. Pat. No. 8,808,195 to Tseng et al., which is incorporated herein by reference.

In an aspect, camera 4606 is a smart camera which captures images of the eyes of patient 4602. Image data may include results of visual spectrum imaging, infrared imaging, ultrasound imaging. Smart cameras are commercially available (e.g., Hamamatsu's Intelligent Vision System; http://jp.hamamatsu.com/en/product_info/index.html). Such image capture systems may include dedicated processing elements for each pixel image sensor. Other possible camera systems may include, for example, a pair of infrared charge coupled device cameras to continuously monitor pupil diameter and position. This can be done as the eye follows a moving visual target, and can provide real-time data relating to pupil accommodation relative to objects on a display (e.g., http://jp.hamamatsu.com/en/rd/publication/scientific_american/common/pdf/scientific_0608.pdf.

Eye movement and/or pupil movement may also be measured by video-based eye tracking circuitry. In these systems, a camera 4606 built into kiosk 4602 focuses on one or both eyes and records eye movement as the viewer looks at a stimulus. Contrast may be used to locate the center of the pupil, and infrared and near-infrared non-collimated light may be used to create a corneal reflection. The vector between these two features can be used to compute gaze intersection with a surface after a calibration for a subject.

Two types of eye tracking techniques include bright pupil eye tracking and dark pupil eye tracking. Their difference is based on the location of the illumination source with respect to the optical system. If the illumination is coaxial with the optical path, then the eye acts as a retroreflector as the light reflects off the retina, creating a bright pupil effect similar to red eye. If the illumination source is offset from the optical path, then the pupil appears dark. Thus, in some embodiments, the gaze tracking stimulus source and the gaze response signal sensor are co-aligned. Alternatively, the gaze tracking stimulus source and the gaze response signal sensor may be separately aligned and located.

Bright Pupil tracking creates greater iris/pupil contrast allowing for more robust eye tracking that is less dependent upon iris pigmentation and greatly reduces interference caused by eyelashes and other obscuring features. It also allows for tracking in lighting conditions ranging from total darkness to very bright light. However, bright pupil techniques are not recommended for tracking outdoors as extraneous infrared (IR) sources may interfere with monitoring.

Most eye tracking systems use a sampling rate of at least 30 Hz. Although 50/60 Hz is most common, many video-based eye tracking systems run at 240, 350 or even 1000/1250 Hz, which is recommended in order to capture the detail of the very rapid eye movements during reading, for example.

Eye movements are typically divided into fixations, when the eye gaze pauses in a certain position, and saccades, when the eye gaze moves to another position. A series of fixations and saccades is called a scanpath. Most information from the eye is made available during a fixation, not during a saccade. The central one or two degrees of the visual angle (the fovea) provide the bulk of visual information; input from larger eccentricities (the periphery) generally is less informative. Therefore the locations of fixations along a scanpath indicate what information loci on the stimulus were processed during an eye tracking session. On average, fixations last for around 200 milliseconds during the reading of linguistic text, and 350 milliseconds during the viewing of a scene. Preparing a saccade towards a new goal takes around 200 milliseconds. Scanpaths are useful for analyzing cognitive intent, interest, and salience. Other biological factors (some as simple as gender) may affect the scanpath as well. Eye tracking in human-computer interaction typically investigates the scanpath for usability purposes, or as a method of input in gaze-contingent displays, also known as gaze-based interfaces.

Commercial eye tracking software packages can analyze eye tracking and show the relative probability of eye fixation at particular locations. This allows for a broad analysis of which locations received attention and which ones were ignored. Other behaviors such as blinks, saccades, and cognitive engagement can be reported by commercial software packages. A gaze tracking system for monitoring eye position is available from Seeing Machines Inc., Tucson, Ariz. (see e.g., the Specification Sheet: "faceLAB™ 5 Specifications" which is incorporated herein by reference). Eye position, eye rotation, eye gaze position against screen, pupil diameter and eye vergence distance may be monitored. Eye rotation measurements of up to +/−45 degrees around the y-axis and +/−22 degrees around the x-axis are possible. Typical static accuracy of gaze direction measurement is 0.5-1 degree rotational error.

In addition, in some aspects an image obtained with camera 4606 can be used to determine movement or coordination of the patient. In an aspect, control/processing circuitry 3580 includes image processing hardware and/or software used to determine an activity or posture of the subject from an image obtained from camera 4606. Such image processing hardware and/or software may, for example, include or generate a model of the background of the image, segment the image, identify the subject in the image, and analyze the image to determine activity or posture of the subject, e.g., based on parameters such as the angle of the torso relative to the hips, or angle of the shoulders relative to the hips. Processing of an image to determine position or posture-related information may be, for example, as described in U.S. Pat. No. 7,616,779 issued Nov. 10, 2009 to Liau et al., U.S. Pat. No. 8,396,283, issued Mar. 12, 2013 to Iihoshi et al., U.S. Pat. No. 7,330,566, issued Feb. 12, 2008 to Cutler, or U.S. Pat. No. 7,728,839 issued Jun. 1, 2010 to Yang et al., each of which is incorporated herein by reference. In addition, the signal from touchscreen 4604, representing entry of data and instructions via touchscreen 4604 by patient 4620 is used as a second activity signal 4616. Rate, timing, type, and consistency of data entry as assessed through analysis of second activity signal 4616 also provide information regarding the patient's brain-related state. Activity Analysis circuitry 3526 combines information from activity signal 4614 and activity signal 4616 to determine compliance of patient 4620 with a prescribed treatment regimen.

Figure 47:
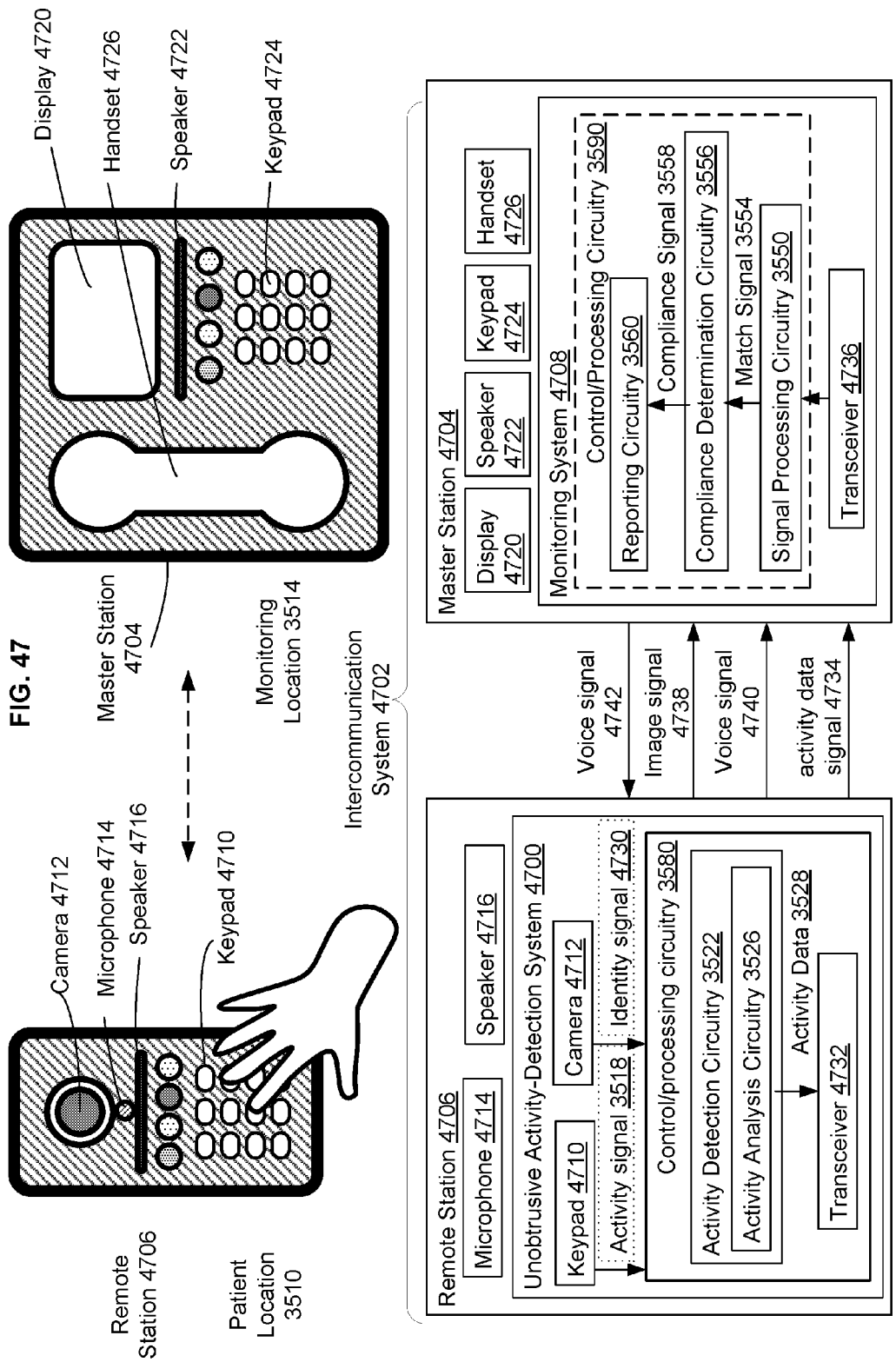
FIG. 47 is an illustration of an unobtrusive activity detection system implemented in an intercommunication system.

FIG. 47 depicts an example of an unobtrusive activity-detection system 4700 that is incorporated into an intercommunication ("intercom") system 4702, for example, of the type used with an access control system to control entry of individuals to an apartment building or office building. In an aspect, intercommunication system 4702 includes master station 4704 and at least one remote station 4706. In an aspect, remote station 4706 is an example of a system 3508 depicted in FIG. 36, and master station 4704 is an example of a system 3512, as depicted in FIG. 38. Master station 4704 is used, for example, at a monitoring location 3514 such as the reception desk of the building, where it is monitored by a member of the building staff, for example. Remote station 4706 is used at an entrance to a building to grant access to regular occupants or visitors to the building. This location is considered to be patient location 3510 in the situation that remote station 4706 is used to control access of the patient to the building. Remote station 4706 includes keypad 4710, camera 4712, microphone 4714, and speaker 4716. In order to request access to the building, the patient typically presses one or more buttons on keypad 4710. An image of the patient is detected with camera 4712; the patient's voice is sensed with microphone 4714 and speaker 4716 provides for delivery of recorded messages, other notification sounds, or verbal instructions from a building staff person at master station 4704. Master station 4704 includes display 4720 for displaying an image of the patient, speaker 4722 for presenting a voice signal detected with microphone 4714, keypad 4724, and handset 4726 which includes a microphone for sensing a voice signal from the building staff person at master station 4704 to deliver to the patient via speaker 4716. The pattern of entry of an access code, detected via keypad 4710, serves as activity signal 3518. Camera 4712 detects an image of the iris of the patient, which serves as identity signal 4730 (i.e., camera 4712 serves as a biometric sensor). Detection of patient presence/identity through biometric analysis can be performed by any of the various approaches described herein above. Activity signal 3518 and identity signal 4730 are processed by control/processing circuitry 3580, activity detection circuitry 3522, activity analysis circuitry 3526 to generate activity data 3528. Transceiver 4732 transmits activity data signal 4734 to transceiver 4736 in monitoring system 4708. In addition, transceiver 4732 transmits image signal 4738 from camera 4712 and voice signal 4740 from microphone 4714, and receives voice signal 4742, sensed via handset 4726, from master station 4704. Activity data signal 4734 is processed by control/processing circuitry 3590, and signal processing circuitry 3550, compliance determination circuitry 3556 and reporting circuitry 3560 as described in connection with FIGS. 35 and 36. Additional data signals and instructions relating to operation of intercommunication system 4702 are sent between remote station 4706 and master station 4704 via transceivers 4732 and 4736, respectively, but are not depicted in FIG. 47.

FIG. 48 depicts an example of an unobtrusive activity-detection system 4800 that includes a motion sensor 4802 built into (or, alternatively, attached to) a hair brush 4804 used by patient 4806. In an aspect, motion sensor 4802 is a tri-axial accelerometer. Motion associated with the use of hair brush 4804 is sensed with motion sensor 4802, and an activity signal 4808 is transmitted to personal computing device 4810. (Here, personal computing device 4810 is a tablet computer, but it could alternatively be a cell phone, laptop computer, desktop computer, for example.) Personal computing device 4810 includes control/processing circuitry 3580, including activity detection circuitry 3522, activity analysis circuitry 3526, and transmitting device 3532. Application software 4812 configures hardware of personal computing device 4810 to perform functions of activity detection circuitry 3522 and activity analysis circuitry 3526. Transmitting device 3532 transmits activity data signal 3534 to monitoring system 4814 via network 4816. In an aspect, activity data signal 3534 includes information regarding the time of day at which hair brush 4804 was used and how long it was used for. In many cases, this will provide sufficient information regarding use of hair brush 4804 by patient 4806. However, information relating to the nature of movement sensed—e.g., was the movement weak or vigorous, erratic or regular, was any tremor detected, etc. may also be sensed and may provide additional information regarding the brain-related functioning of patient 4806. In another aspect, motion sensor 4802 or other activity sensor, activity detection circuitry 3522, activity analysis circuitry 3526, and transmitting device 3532 are all components of a personal item such as hair brush 4804.

Figure 49:
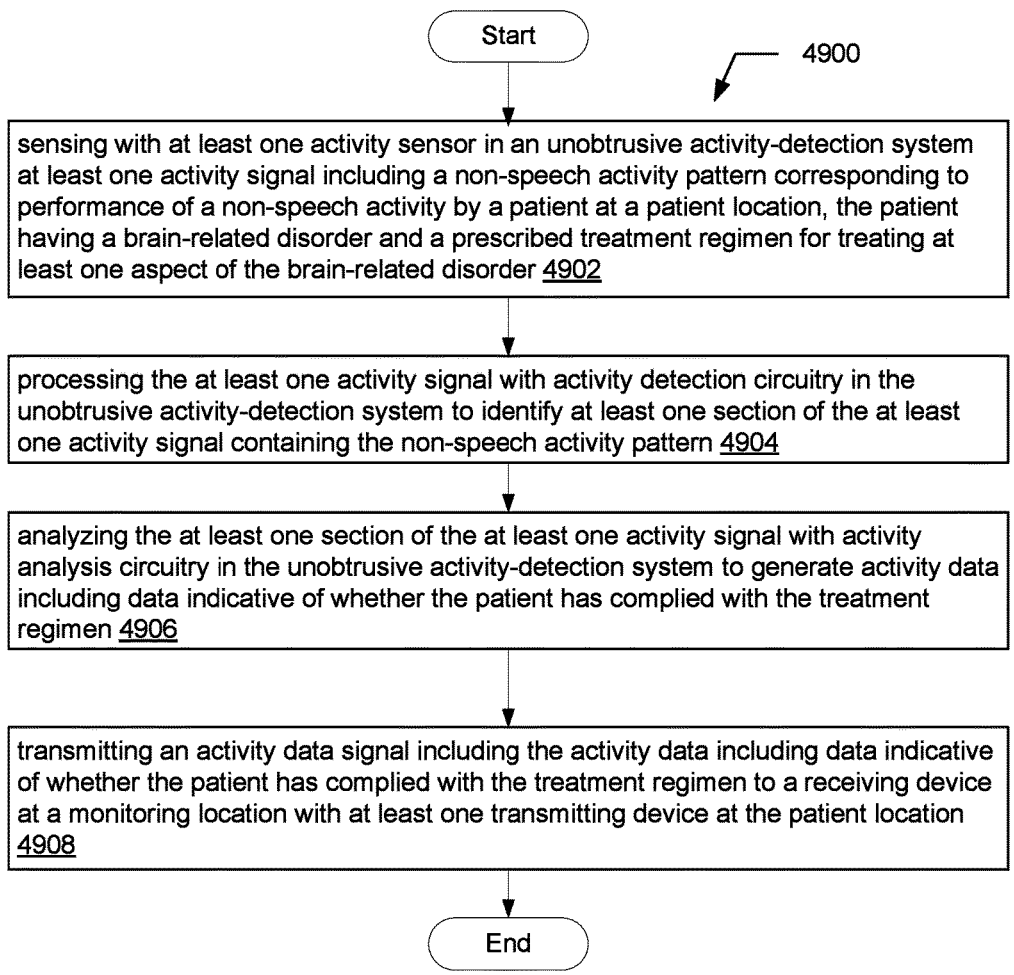
FIG. 49 is a flow diagram of a method relating to monitoring compliance of a patient with a prescribed treatment regimen.

FIG. 49 is a flow diagram of a method 4900 relating to monitoring compliance of a patient with a prescribed treatment regimen. Method 4900 includes sensing with at least one activity sensor in an unobtrusive activity-detection system at least one activity signal including a non-speech activity pattern corresponding to performance of a non-speech activity by a patient at a patient location, the patient having a brain-related disorder and a prescribed treatment regimen for treating at least one aspect of the brain-related disorder, as indicated at 4902; processing the at least one activity signal with activity detection circuitry in the unobtrusive activity-detection system to identify at least one section of the at least one activity signal containing the non-speech activity pattern, as indicated at 4904; analyzing the at least one section of the at least one activity signal with activity analysis circuitry in the unobtrusive activity-detection system to generate activity data including data indicative of whether the patient has complied with the treatment regimen, as indicated at 4906; and transmitting an activity data signal including the activity data including data indicative of whether the patient has complied with the treatment regimen to a receiving device at a monitoring location with at least one transmitting device at the patient location, as indicated at 4908. In various aspects, method 4900 is carried out with unobtrusive activity detection system 3508 as depicted in FIGS. 35, 36 and 37, for example.

Figure 50:
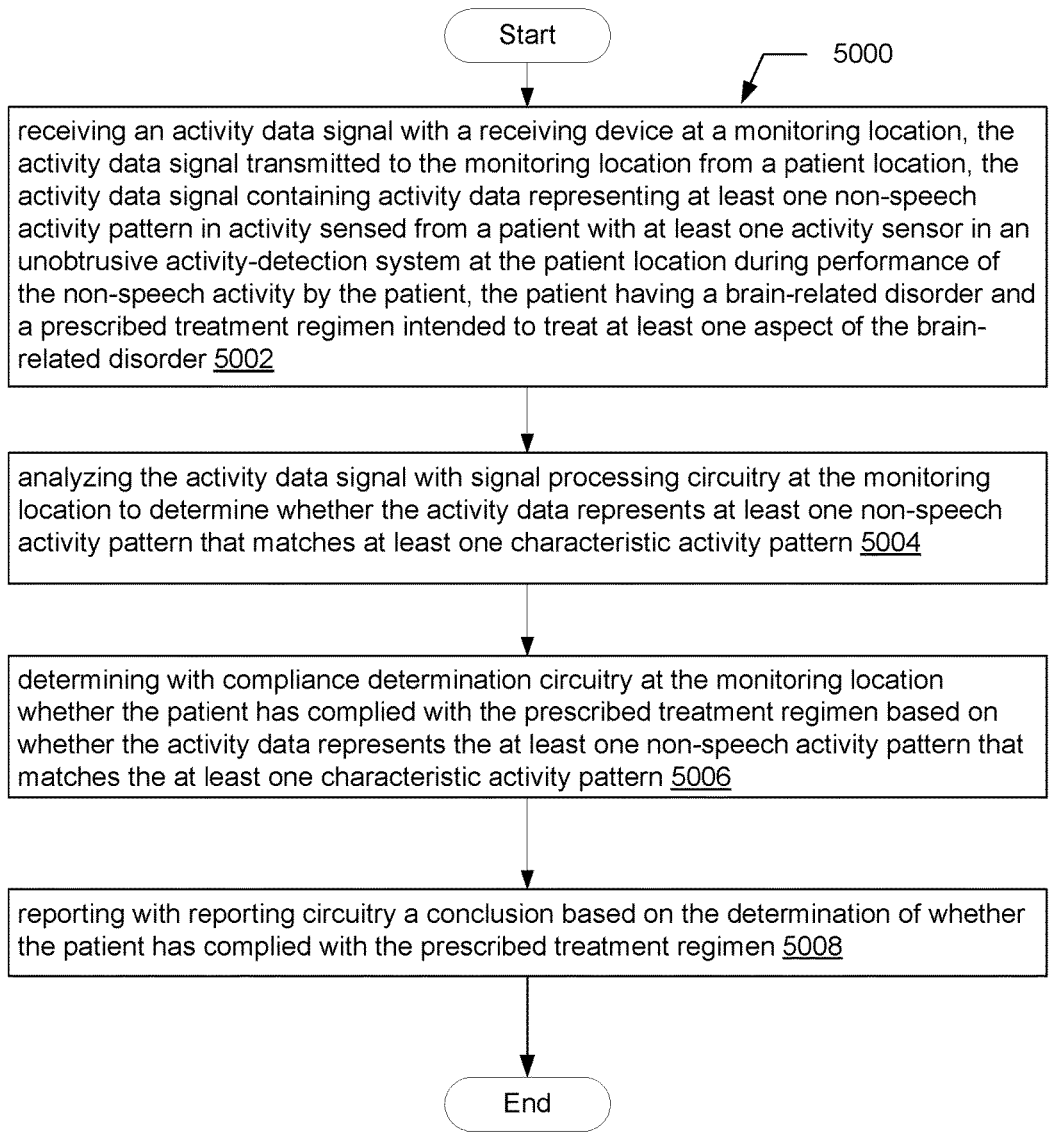
FIG. 50 is a flow diagram of a method of monitoring compliance of a patient with a prescribed treatment regimen.

FIG. 50 is a flow diagram of a method 5000 relating to monitoring compliance of a patient with a prescribed treatment regimen. Method 5000 includes receiving an activity data signal with a receiving device at a monitoring location, the activity data signal transmitted to the monitoring location from a patient location, the activity data signal containing activity data representing at least one non-speech activity pattern in activity sensed from a patient with at least one activity sensor in an unobtrusive activity-detection system at the patient location during performance of the non-speech activity by the patient, the patient having a brain-related disorder and a prescribed treatment regimen intended to treat at least one aspect of the brain-related disorder, as indicated at 5002; analyzing the activity data signal with signal processing circuitry at the monitoring location to determine whether the activity data represents at least one non-speech activity pattern that matches at least one characteristic activity pattern, as indicated at 5004; determining with compliance determination circuitry at the monitoring location whether the patient has complied with the prescribed treatment regimen based on whether the activity data represents the at least one non-speech activity pattern that matches the at least one characteristic activity pattern, as indicated at 5006; and reporting with reporting circuitry a conclusion based on the determination of whether the patient has complied with the prescribed treatment regimen, as indicated at 5008. In various aspects, method 5000 is carried out with monitoring system 118 as depicted in FIGS. 35 and 38, for example.

Figure 51:
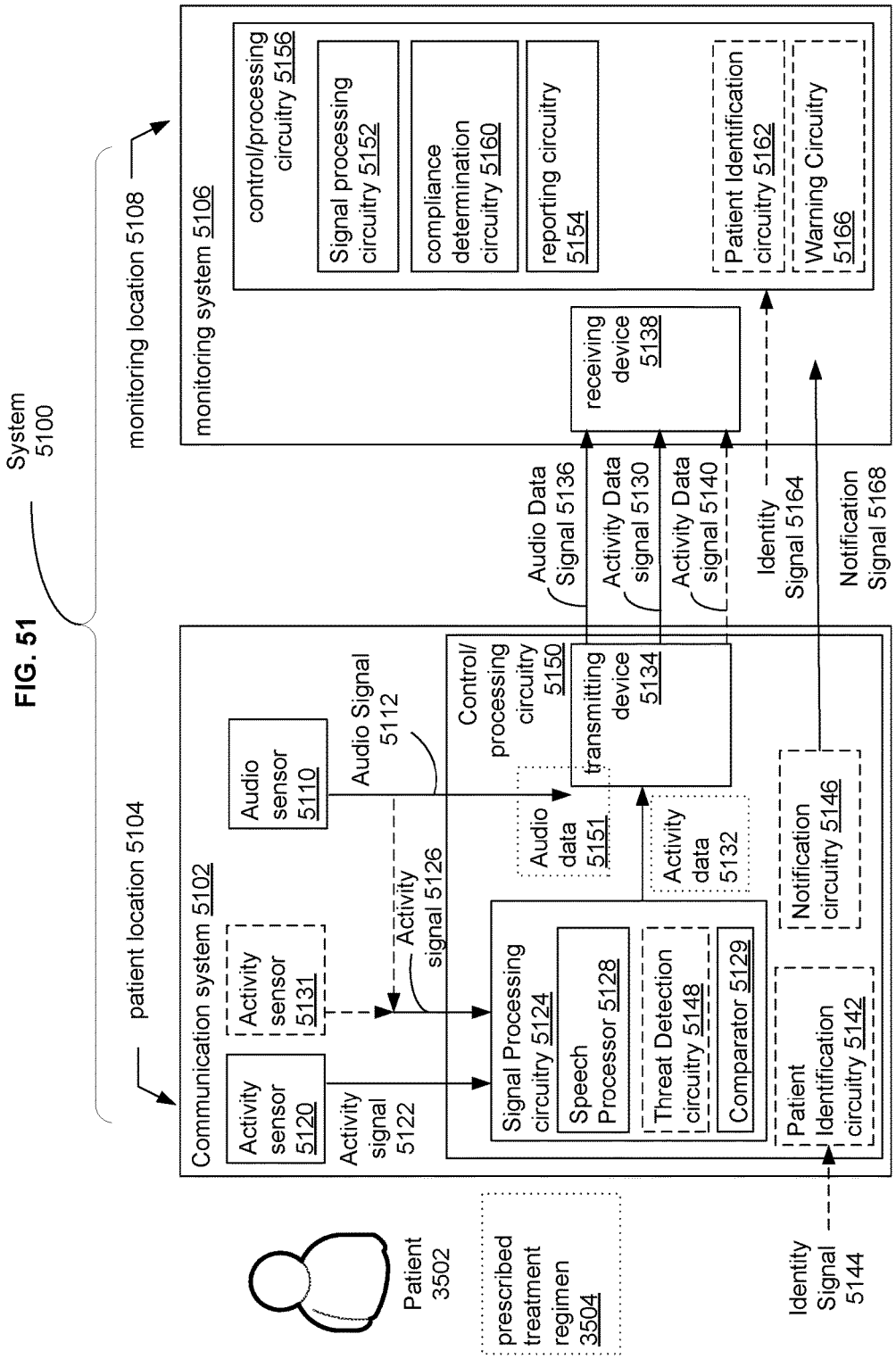
FIG. 51 is a block diagram of a system for monitoring compliance of a patient with a treatment regimen.

FIG. 51 is a block diagram of a system 5100 for monitoring compliance of a patient with a treatment regimen based upon two or more sensed signals. System 5100 includes communication system 5102 at patient location 5104 and monitoring system 5106 at monitoring location 5108. In general, communication system 5102 includes components shown in unobtrusive activity detection system 3508 in FIG. 36, as well as any additional components required for perform communication system functions.

Communication system 5102 includes at least one audio sensor 5110 for sensing at least one audio signal 5112, which includes patient speech from patient 3502 at a patient location 5104 during use of communication system 5102. In an aspect, communication system 5102 includes a telephone (e.g., as depicted in FIG. 41), an intercommunication system (e.g., as depicted in FIG. 47), or a radio communication system, and audio sensor is a microphone or other audio sensing device as known by those of ordinary skill in the art. Patient 3502 has a brain-related disorder and a prescribed treatment regimen 3504 for treating at least one aspect of the brain-related disorder. Communication system 5102 includes at least one first activity sensor 5120 for sensing at least one first activity signal 5122 indicative of a first activity of the patient. Communication system 5102 includes signal processing circuitry 5124, which is configured to process the at least one first activity signal 5122 and at least one second activity signal 5126, which indicative of a second activity of the patient, to generate at least one activity data signal 5130, the activity data signal 5130 containing activity data 5132 indicative of whether the patient has complied with the treatment regimen. Communication system 5102 also includes at least one transmitting device 5134 at the patient location for transmitting the at least one activity data signal 5130 and at least one audio data signal 5136 based on the at least one audio signal 5112 to a receiving device 5138 at monitoring location 5108. In an aspect, activity signal 5126 includes audio signal 5112 from audio sensor 5110, which can supply information regarding speech or vocal activity of patient 3502. In an aspect, signal processing circuitry 5124 includes speech processor 5128. In an aspect, speech processor 5128 is configured to process the at least one audio signal 5112 to identify at least one portion of the at least one audio signal 5112 containing spontaneous speech of the patient. In an aspect, speech processor 5128 is configured to process at least one audio signal 5112 to exclude at least one portion of at least one audio signal 5112 that does not contain spontaneous speech of the patient. In an aspect, activity data 5132 includes the at least one section of the at least one audio signal 5112 containing spontaneous speech of the patient.

In an aspect, speech processor 5128 is configured to process at least one audio signal 5112 to determine at least one speech pattern of the patient. In an aspect, activity data 5132 includes the at least one speech pattern.

For example, the at least one speech pattern may be represented in activity data 5132 in numerical or categorical form. For example, a speech pattern represented in numerical form may include one or more numerical values representing one or more speech parameters. Particular speech parameters represented in a speech pattern may be selected for the purpose of evaluating/monitoring particular brain-related disorders. For example, in an aspect a speech pattern for evaluating/monitoring depression includes values representing the following parameters: speech volume, frequency of word production, frequency of pauses, and frequency of negative value words. In another aspect, a speech pattern for evaluating/monitoring schizophrenia includes values representing frequency of word production, frequency of pauses, frequency of disfluencies, type:token ratio, and speech volume. A speech parameter or pattern may be represented in activity data 5132 in categorical form; for example, frequency of word production may be categorized as low, medium, or high rather than represented by a specific numerical value.

In an aspect, signal processing circuitry 5124 includes a comparator 5129 for comparing speech patterns or parameters of patient 3502 with characteristic speech patterns or parameters, in an approach similar to that described above in connection with comparator 3654 in FIG. 36, to determine whether the patient has complied with the prescribed treatment regimen. In an aspect, comparator 5129 is configured to compare at least one speech pattern of the patient with a plurality of characteristic speech patterns. In an aspect, the result of such a comparison is either "patient has complied" or "patient has not complied." In an aspect, signal processing circuitry 5124 is configured to determine that patient 3502 has failed to comply with the prescribed treatment regimen. In an aspect, signal processing circuitry 5124 is configured to determine that patient 3502 has complied with prescribed treatment regimen 3504. Determination of compliance may be accomplished by a thresholding, windowing, or distance computation of one or multiple parameters relative to characteristic threshold or range values for the parameter, and combining results for the multiple parameters. For example, for a given parameter (relating to activity sensed with one or more activity sensor or audio sensor), a patient parameter value higher than a characteristic threshold value may indicate compliance of the patient with the prescribed treatment regimen, while a patient parameter value equal to or lower than the threshold value may indicate non-compliance. As another example, a patient parameter value that lies within a range of characteristic values for the parameter may indicate compliance, while a patient parameter value outside the range of characteristic values indicates non-compliance. Comparator 5129 may utilize various types of distance computations to determine whether patient parameter values are within a threshold distance or distance range from characteristic values. Distance computations based on one or more parameters or data values are known (including, but not limited to, least-squares calculations). Different activity parameters or audio signal parameters may be given different weights depending on how strongly indicative the parameter is of the patient compliance. In an aspect, signal processing circuitry 5124 is configured to determine whether the patient has complied with the prescribed treatment regimen based upon a determination of whether the speech corresponds to at least one of a plurality of characteristic speech patterns. For example, the plurality of characteristic speech patterns can include multiple characteristic speech patterns, each corresponding to a patient speech pattern obtained at a different treatment regimen, for example, different doses of a drug. By identifying which characteristic speech pattern the patient speech pattern matches or is closest to, the drug dose taken by the patient can be determined. For example, the patient may have taken the drug, but at a lesser dose or less often than was prescribed. Accordingly, the patient's speech pattern matches the characteristic speech pattern associated with the lesser dose of drug, indicating partial, but not full, compliance of the patient with the prescribed treatment regimen.

In an aspect, speech processor 5128 is configured to process at least one audio signal 5112 to determine at least one speech parameter indicative of whether the patient has complied with the prescribed treatment regimen. Speech parameters include, but are not limited to, measures of prosody, rhythm, stress, intonation, variance, intensity/volume, pitch, length of phonemic syllabic segments, and length of rising segments, for example. In an aspect, audio data includes at least one speech parameter, which may include, for example, one or more of prosody, rhythm, stress, intonation, variance, intensity/volume, pitch, length of phonemic syllabic segments, and length of rising segments. In an aspect, signal processing circuitry 5124 includes comparator 5129 for comparing at least one speech parameter of the patient with at least one characteristic speech parameter to determine whether the patient has complied with the prescribed treatment regimen. In an aspect, comparator 5129 is configured to compare at least one speech parameter of the patient with a plurality of characteristic speech parameters to determine whether the patient has complied with the prescribed treatment regimen. For example, in an aspect, the result of such a comparison is either "patient has complied" or "patient has not complied." In an aspect, comparator 5129 determines a level of compliance of the patient with the prescribed treatment regimen. Determination of compliance, non-compliance, or level of compliance may be performed with comparator 5129 using thresholding, windowing, or distance measurements, for example, as described herein above. Similarly, determination of compliance or non-compliance of patient 3502 with a prescribed treatment regimen may be accomplished with the use of comparator 5129 using approaches as described herein above.

In an aspect, activity signal 5126 includes a signal from one or more additional activity sensor(s) 5131. In various aspects, first activity sensor 5120 and any additional activity sensor(s) 5131 include any of the various types of activity sensor 3516 described herein above, e.g., as in connection with FIG. 37. In an aspect, signal processing circuitry 5124 processes at least one first activity signal 5122 and at least one second activity signal 5126 using signal processing approaches as described herein above (e.g., as described in connection with activity detection circuitry 3522/activity analysis circuitry 3526 in FIG. 35), to generate activity data 5132, which is included in activity data signal 5130. In some aspects, more than one activity data signal is generated (e.g., activity data signal 5130 and activity signal 5140). In some aspects, activity data from different activity sensors is transmitted in separate activity data signals. In other aspects, activity data from multiple activity sensors is transmitted in a single activity data signal. In an aspect, audio data signal 5136 is a radio frequency signal containing telecommunication data. In some aspects, audio data signal 5136 is combined with activity data signal 5130. In some aspects, communication system 5102 includes patient identification circuitry 5142, which is used to determine the presence of patient 3502 based on identity signal 5144, using an approach as described herein above, e.g., in connection with patient identification circuitry 3622 in FIG. 36. In some aspects, communication system 5102 includes notification circuitry 5146, which functions in the same manner as notification circuitry 3690 in FIG. 36. In an aspect, communication system 5102 includes threat detection circuitry 5148 in signal processing circuitry 5124. Threat detection circuitry 5148 is used for determining, based upon at least one of the at least one first activity signal and the at least one second activity signal, whether the patient poses a threat. Threat can be determined using approaches as described, for example, in U.S. Patent Application 2006/0190419 dated Aug. 24, 2016 to Bunn et al., and U.S. Patent Application 2006/00208556 dated Feb. 9, 2006 to Bunn et al., both of which are incorporated herein by reference. If it is determined that that patient poses a threat, a notification indicative of the threat is generated with notification circuitry 5146, and the notification is delivered to the threatened party via warning circuitry 5166 in monitoring system 5106. Alternatively, or in addition, warning circuitry may be located separately from monitoring system 5106. Signal processing circuitry 5124, patient identification circuitry 5142, notification circuitry 5146, threat detection circuitry 5148, and transmitting device 5134 are components of control/processing circuitry 5150.

Monitoring system 5106 includes at least one receiving device 5138 for use at a monitoring location 5108 for receiving at least one activity data signal 5130 and at least one audio data signal 5136 (and, optionally one or more additional activity data signal 5140) from communication system 5102 and is similar to receiving device 3536 in FIGS. 35 and 38. Audio data signal 5136 includes audio data 5151 representing speech from patient 3502 sensed with at least one audio sensor 5110 at the patient location 5104 during use of communication system 5102, and transmitted to the monitoring location 5108. Activity data signal 5130 includes activity data 5132 indicative of whether patient 3502 has complied with the prescribed treatment regimen 3504. Activity data 5132 represents at least one first activity of the patient. Monitoring system 5106 includes signal processing circuitry 5152, which is configured to process the at least one activity data signal 5130 to determine, based upon the at least one first activity of the patient and at least one second activity of the patient, whether the patient has complied with the prescribed treatment regimen, and reporting circuitry 5154 configured to report a conclusion based on the determination of whether the patient has complied with the prescribed treatment regimen. Signal processing circuitry 5152 is substantially similar to signal processing circuitry 3550 as discussed in connection with FIGS. 35 and 38. Reporting circuitry 5154 is substantially the same as reporting circuitry 3560 as discussed in connection with FIGS. 35 and 38. Signal processing circuitry 5152 and reporting circuitry 5154 are components of control/processing circuitry 5156 in monitoring system 5106. In an aspect, control/processing circuitry 5156 includes compliance determination circuitry 5160, which functions in the same manner as compliance determination circuitry 156 in FIGS. 35 and 38, as discussed herein above. In an aspect control/processing circuitry 5156 includes patient identification circuitry 5162, which determines a presence of patient 3502 at patient location 5104 based on identity signal 5164, in the same manner as patient identification circuitry 410 depicted in FIG. 38 and described herein above. In an aspect, control/processing circuitry 5156 includes warning circuitry 5166, which delivers a warning to a threatened party in response to a notification. The notification is received from the patient location, e.g., in the form of notification signal 5168 from transmitting device 5134, as described herein above. Delivering a warning to a threatened party may include, for example, displaying a warning message, playing a recorded warning message, or generating an audible alarm tone. The warning may be delivered in the same general manner as conclusion 3562 is reported by reporting circuitry 3560, as described herein above, in connection with FIG. 38.

Figure 52:
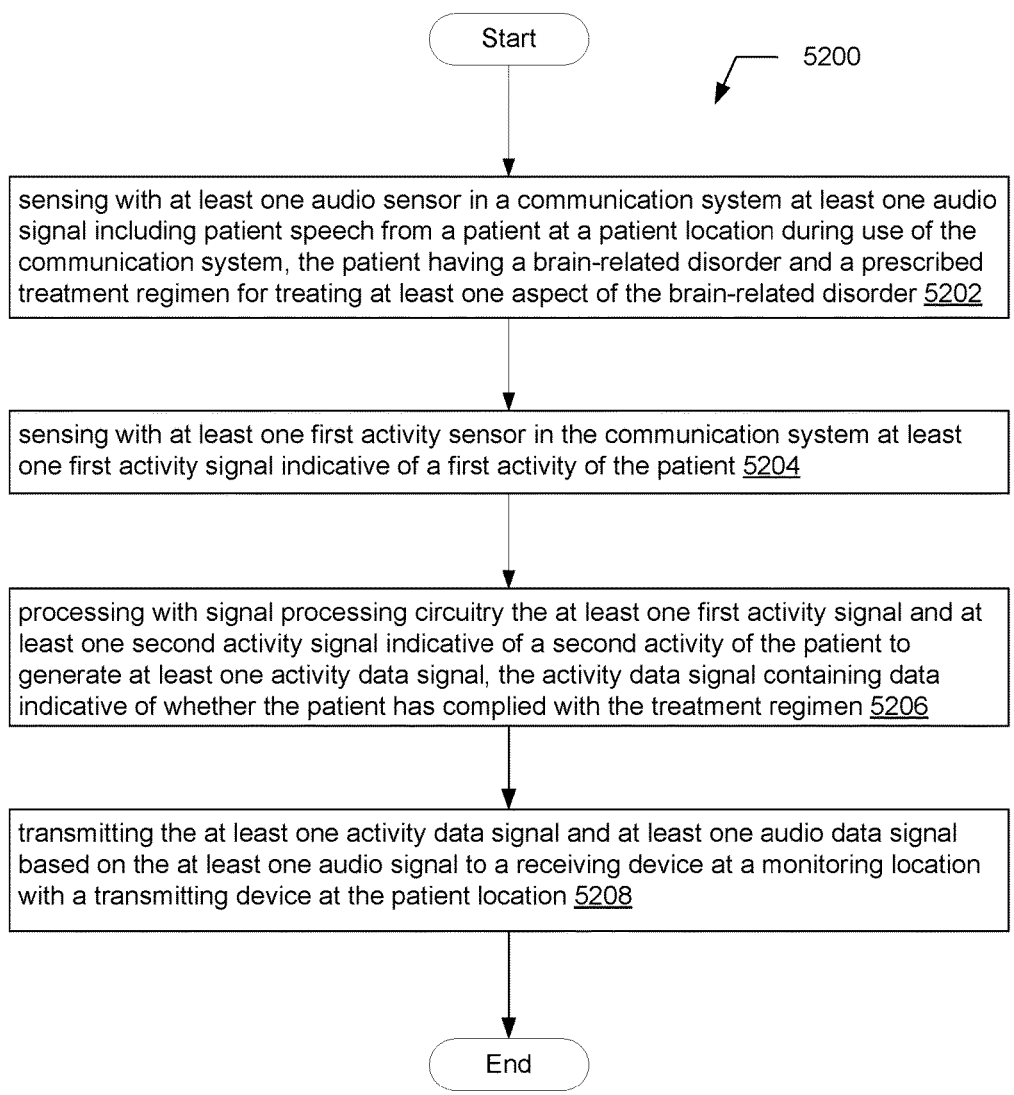
FIG. 52 is a flow diagram of a method is a flow diagram of a method of monitoring compliance of a patient with a prescribed treatment regimen.

FIG. 52 is a flow diagram of a method 5200 relating to monitoring compliance of a patient with a prescribed treatment regimen using a system such as system 5102 in FIG. 51 according to principles as described herein above. Method 5200 includes sensing with at least one audio sensor in a communication system at least one audio signal including patient speech from a patient at a patient location during use of the communication system, the patient having a brain-related disorder and a prescribed treatment regimen for treating at least one aspect of the brain-related disorder, as indicated at 5202; sensing with at least one first activity sensor in the communication system at least one first activity signal indicative of a first activity of the patient, as indicated at 5204; processing with signal processing circuitry the at least one first activity signal and at least one second activity signal indicative of a second activity of the patient to generate at least one activity data signal, the activity data signal containing data indicative of whether the patient has complied with the treatment regimen, as indicated at 5206; and transmitting the at least one activity data signal and at least one audio data signal based on the at least one audio signal to a receiving device at a monitoring location with a transmitting device at the patient location, as indicated at 5208.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g., "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
  at least one audio sensor in a communication system for sensing at least one audio signal including patient speech from a patient at a patient location during use of the communication system, the patient having a brain-related disorder and a prescribed treatment regimen for treating at least one aspect of the brain-related disorder;
  at least one first activity sensor for sensing at least one first activity signal indicative of a first activity of the patient;

signal processing circuitry configured to process the at least one first activity signal and at least one second activity signal indicative of a second activity of the patient to generate at least one activity data signal, the activity data signal containing activity data indicative of whether the patient has complied with the treatment regimen; and at least one transmitting device at the patient location for transmitting the at least one activity data signal and at least one audio data signal based on the at least one audio signal to a receiving device at a monitoring location.

2. The system of claim 1, including at least one second activity sensor for sensing the at least one second activity signal indicative of the second activity of the patient.

3. The system of claim 2, wherein the at least one second activity sensor includes at least one physiological sensor, eye position sensor, EEG sensor, EEG sensor configured to detect an event-related potential, heart rate sensor, pupil diameter sensor, imaging device, remote controller for an entertainment device or system, game controller, input device, pointing device, touchscreen, RFID sensor, user-activated sensor in a vehicle system, wearable sensor, environmental sensor, pressure sensor, force sensor, capacitive sensor, optical sensor, motion sensor, motion capture device, or acceleration sensor.

4. The system of claim 1, wherein the at least one first activity sensor is configured to transduce an activity signal associated with performance of a non-speech activity.

5. The system of claim 1, including
patient identification circuitry configured to determine a presence of the patient from at least one identity signal sensed at the patient location;
wherein the signal processing circuitry is configured to detect an activity of the patient based at least in part on the determination of the presence of the patient by the patient identification circuitry.

6. The system of claim 5, wherein the identity signal includes at least one of a portion of the at least one first activity signal, a portion of the at least one second activity signal, an audio signal from the audio sensor at the patient location, an image signal from an imaging device at the patient location, a biometric signal from at least one biometric sensor at the patient location, at least one authentication factor, a security token, a password, a digital signature, and a cryptographic key, a cell phone identification code, an electronic serial number, a mobile identification number, a system identification code, or an RFID signal.

7. The system of claim 1, wherein the signal processing circuitry includes activity analysis circuitry for processing the at least one first activity signal and the at least one second activity signal to determine at least one activity pattern of the patient.

8. The system of claim 7, wherein the activity analysis circuitry includes at least one of an activity analyzer for assessing the at least one activity pattern to determine at least one activity parameter indicative of whether the patient has complied with the treatment regimen, wherein the activity data signal includes the at least one activity parameter; or a comparator for comparing the at least one activity pattern with at least one characteristic activity pattern to determine whether the patient has complied with the treatment regimen.

9. The system of claim 1, including notification circuitry for generating a notification indicative of whether the patient has complied with the treatment regimen.

10. The system of claim 9, including
threat detection circuitry for determining based upon at least one of the at least one first activity signal and the at least one second activity signal that the patient poses a threat;
wherein the notification circuitry is configured to generate a notification indicative of the threat.

11. The system of claim 9, wherein the notification circuitry includes at least one of circuitry for generating an email notification, circuitry for generating a notification to be transmitted to a wireless device, circuitry for storing a notification in a data storage device, or circuitry for generating an audio notification.

12. The system of claim 1, wherein the at least one first activity sensor includes at least one of an imaging device, a remote controller for an entertainment device, a remote controller for an entertainment, a game controller, an input device, a pointing device; a touchscreen; an RFID sensor; a user-activated sensor in a vehicle system; a wearable sensor; an environmental sensor; a pressure sensor; a force sensor; a capacitive sensor; an optical sensor; a motion sensor; a motion capture device.

13. A method comprising:
sensing with at least one audio sensor in a communication system at least one audio signal including patient speech from a patient at a patient location during use of the communication system, the patient having a brain-related disorder and a prescribed treatment regimen for treating at least one aspect of the brain-related disorder;
sensing with at least one first activity sensor in the communication system at least one first activity signal indicative of a first activity of the patient;
processing with signal processing circuitry the at least one first activity signal and at least one second activity signal indicative of a second activity of the patient to generate at least one activity data signal, the activity data signal containing data indicative of whether the patient has complied with the treatment regimen; and
transmitting the at least one activity data signal and at least one audio data signal based on the at least one audio signal to a receiving device at a monitoring location with a transmitting device at the patient location.

14. A system comprising:
a computing device; and
instructions that when executed on the computing device cause the computing device to:
control sensing with at least one audio sensor of at least one audio signal including patient speech from a patient at a patient location, the patient having a brain-related disorder and a prescribed treatment regimen for treating at least one aspect of the brain-related disorder;
control sensing with at least one first activity sensor in an unobtrusive activity-detection system of at least one first activity signal indicative of a first activity of the patient;
process with signal processing circuitry the at least one first activity signal and at least one second activity signal indicative of a second activity of the patient to generate at least one activity data signal, the activity data signal containing data indicative of whether the patient has complied with the treatment regimen; and
control transmitting with a transmitting device at the patient location of the at least one activity data signal and at least one audio data signal based on the at least one audio signal to a receiving device at a monitoring location.

* * * * *